US008569071B2

(12) United States Patent
Nimkar et al.

(10) Patent No.: US 8,569,071 B2
(45) Date of Patent: Oct. 29, 2013

(54) AMINE-CONTAINING COMPOUND ANALYSIS METHODS

(75) Inventors: Subodh B. Nimkar, Foster City, CA (US); Subhasish Purkayastha, Acton, MA (US); Darryl Pappin, Boxborough, MA (US); Scott Daniels, Bolton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 552 days.

(21) Appl. No.: 12/555,319

(22) Filed: Sep. 8, 2009

(65) Prior Publication Data

US 2010/0093011 A1 Apr. 15, 2010

Related U.S. Application Data

(63) Continuation of application No. 11/350,147, filed on Feb. 8, 2006, now abandoned.

(60) Provisional application No. 60/651,734, filed on Feb. 9, 2005.

(30) Foreign Application Priority Data

Feb. 9, 2005 (EP) ..................................... 06720540
Feb. 9, 2005 (JP) ............................... 2007-0555212
Feb. 9, 2005 (WO) ................... PCT/US2006/04548

(51) Int. Cl.
*G01N 24/00* (2006.01)

(52) U.S. Cl.
USPC .............. 436/173; 436/86; 436/111; 435/6.1; 435/18; 435/23; 435/25; 544/358; 544/392; 544/398; 544/399

(58) Field of Classification Search
None
See application file for complete search history.

(56) References Cited

U.S. PATENT DOCUMENTS 5,075,547 A 12/1991 Johnson et al.
5,705,610 A 1/1998 Zuckermann et al.
(Continued)

FOREIGN PATENT DOCUMENTS

EP 0945893 9/1999
EP 0781145 7/2003
(Continued)

OTHER PUBLICATIONS

Ross, Philip L., et al. Multiplexed protein quantitation in Saacharomyces cerevisiae using amine-reactive isobaric tagging reagents, 2004, Molecular & Cellular Proteomics, vol. 3, pp. 1154-1169.*

(Continued)

*Primary Examiner* — Robert Xu

(57) ABSTRACT

The present teachings provide methods for analyzing one or more amine-containing compounds in one or more samples using isobaric labels and parent-daughter ion transition monitoring (PDITM). In various embodiments, the methods comprise the steps of: (a) labeling one or more amine-containing compounds with different isobaric tags from a set of isobaric tags, each isobaric tag comprising a reporter ion portion; (b) combining at least a portion of each of the isobarically labeled amine-containing compounds to produce a combined sample; (c) subjecting at least a portion of the combined sample to PDITM; (d) measuring the ion signal of one or more of the transmitted reporter ions; and (e) determining the concentration of one or more of the isobarically labeled amine-containing compounds based at least on a comparison of the measured ion signal of the corresponding reporter ion to one or more measured ion signals of a standard compound.

30 Claims, 69 Drawing Sheets

(56) References Cited

U.S. PATENT DOCUMENTS

| | | | |
|---|---|---|---|
| 5,800,992 | A | 9/1998 | Fodor et al. |
| 5,916,537 | A | 6/1999 | Kajiwara et al. |
| 6,011,259 | A | 1/2000 | Whitehouse et al. |
| 6,027,890 | A | 2/2000 | Van Ness et al. |
| 6,190,316 | B1 | 2/2001 | Hirabayashi et al. |
| 6,270,976 | B1 | 8/2001 | Schmidt et al. |
| 6,287,780 | B1 | 9/2001 | Schmidt et al. |
| 6,358,996 | B1 | 3/2002 | Alexander et al. |
| 6,432,639 | B1 | 8/2002 | Lichter et al. |
| 6,475,807 | B1 | 11/2002 | Geysen et al. |
| 6,670,194 | B1 | 12/2003 | Aebersold et al. |
| 2002/0030159 | A1 | 3/2002 | Chernushevich et al. |
| 2002/0076739 | A1 | 6/2002 | Aebersold et al. |
| 2002/0192720 | A1 | 12/2002 | Parker et al. |
| 2003/0194717 | A1 | 10/2003 | Schmidt et al. |
| 2003/0211622 | A1 | 11/2003 | Roberts |
| 2003/0213901 | A1 | 11/2003 | Covey et al. |
| 2004/0026612 | A1 | 2/2004 | Bateman et al. |
| 2004/0033625 | A1 | 2/2004 | Aebersold |
| 2004/0219686 | A1 | 11/2004 | Pappin et al. |
| 2004/0220412 | A1 | 11/2004 | Pappin et al. |
| 2005/0147982 | A1 | 7/2005 | Pappin et al. |
| 2005/0147985 | A1 | 7/2005 | Pappin et al. |
| 2005/0148087 | A1 | 7/2005 | Pappin et al. |
| 2005/0148771 | A1 | 7/2005 | Dey et al. |
| 2005/0148773 | A1 | 7/2005 | Pappin et al. |
| 2005/0148774 | A1 | 7/2005 | Dey et al. |
| 2005/0208550 | A1 | 9/2005 | Pappin et al. |

FOREIGN PATENT DOCUMENTS

| | | |
|---|---|---|
| JP | 9-257791 | 10/1997 |
| JP | 11-271277 | 10/1999 |
| JP | 2002-523058 | 7/2002 |
| WO | WO9705906 | 2/1997 |
| WO | 9727331 | 7/1997 |
| WO | 9826095 | 6/1998 |
| WO | 9831830 A | 7/1998 |
| WO | 0011208 | 3/2000 |
| WO | 0229003 | 4/2002 |
| WO | 0248717 | 6/2002 |
| WO | 03025576 | 3/2003 |
| WO | 03056299 | 7/2003 |
| WO | 03069328 | 8/2003 |
| WO | 2004019000 A | 3/2004 |
| WO | 2004070352 A | 8/2004 |
| WO | WO2004081555 | 9/2004 |
| WO | 2004086050 | 10/2004 |
| WO | 2004090553 | 10/2004 |
| WO | WO2004100207 | 11/2004 |
| WO | 2005012247 | 2/2005 |
| WO | 2005068446 A | 7/2005 |
| WO | 2005114700 | 12/2005 |
| WO | 2006017208 | 2/2006 |

OTHER PUBLICATIONS

Bottari P et al., "Design and Synthesis of Visable Isotope-Coded Affinity Tags for the Absolute Quantification of Specific Proteins in Complex Mixtures," Bioconjugate CHEMISTRYm ACS, Washington, D.C., vol. 15, No. 2, Feb. 21, 2004, pp. 380-388.

Dunayevskiy, Yuriy M., "Application of Capillary Electrophoresis-Electrospray Ionization Mass Spectrometry in the Determination of Molecular Diversity," PNAS 1996, Proc. Natl. Acad. Sci. USA 93, Boston, MA, Jan. 30, 1996, pp. 6152-6157.

Gygi S P et al., "Quantitative Analysis of Complex Protein Mixtures Using Isotope-Coded Affinity Tags," Nature Biotechnology, Nature Publishing Group, New York, NY, vol. 17, No. 10, Oct. 1, 1999, pp. 994-999.

Stering, Kenneth et al., "Molecular Structure of Thyroxide in Relation to its Binding by Human Serum Albumin," 1964, Journal of Clinical Investigation, vol. 43(9), pp. 1721-1729.

Unwin et al., "Multiple Reaction Monitering to Identify Sites of Protein Phosphorylation with High Sensitivity," Mol Cell Proteomics, 4: 1134-44, 2005.

Adkins et al., "Toward a Human Blood Surm Proteome," Molecular & Cellular Proteomics, 1: 947-55, 2002.

Agrawal et al., "Constitution and Inducible Hepatic Cytochrome P450 Isoforms in Senescent Male and Female Rats and Response to Low-Dose Phenobarbital," Drug Metabolism and Disposition, 31(5): 612-9, 2003.

Anderson et al., "The Human Plasma Proteome," Molecular & Cellular Proteomics, 1: 845-67, 2002.

Anderson et al., "Candidate-based Proteomics in the Search for Biomarkers of Cardiovascular Disease," J. Physiol, 563(1): 23-60, 2005.

Anderson et al., "Mass Spectrometric Quantification of Peptides and Proteins Using Stable Isotope Standards and Capture by Anti-Peptide Antibodies (SISCAPA)," J. Proteome Res., 3(3): 235-44, 2004.

Bakhtiar, R. et al., "Mass Spectrometry of the Proteome," Mol Pharmacol., 60: 405-415, 2001.

Barnidge. David R. et al., "Absolute Quantification of the G Protein-Coupled Receptor Rhodopsin by LC/MS/MS Using Proteolysis Product Peptides and Synthetic Peptide Standards," Anal. Chem., 75:445-451, 2003.

Craig et al., "Open Source System for Analyzing, Validating, and Sorting Protein Identification Data," J. Proteome Res., 3(6): 1234-1242, 2004.

Feasley et al., "Affinity Selection of Glycopeptides in Canine Immune-Mediated Arthritis," 52nd Conference of the American Society for Mass Spectrometry, May 24-27, 2004, Nashville, Tennessee.

Gartner et al., "Use of a Non-Cleavable Isotope-Labeled Biotin Reagent for the Determination of Relative Protein Expression Levels," 52nd Conference of the American Society for Mass Spectrometry, May 24-27, 2004, Nashville, Tennessee.

Gerber et al., "Absolute Quantification of Proteins and Phosphoproteins from Cell Lysates by Tandem MS," PNAS, 100(12): 6940-6945, 2003.

Grote et al., "Double-Detecion Technology for Bioaffinity Studies," 52nd Conference of the American Society for Mass Spectrometry, May 24-27, 2004, Nashville, Tennessee.

Hahner, S. et al., "Label-Free Quantitative Protein Analysis be LC-MALDI-TOF/TOF," 52nd Conference of the American Society for Mass Spectrometry, May 24-27, 2004, Nashville, Tennessee.

Haley, J. D. et al., "A Novel Fragment Ion Tag Approach to the Measurement of Tyrosine Kinase Signaling Pathways," 52nd Conference of the American Society for Mass Spectrometry, May 24-27, 2004, Nashville, Tennessee.

Hopp et al., "Predictions of Protein Antigenic Determinants from Amino Acid Sequences," Proc. Natl. Acad. Sci. USA, 70(6): 3824-3828, 1981.

Hunter et al., "Using Stable Isotope Tags and a Hybrid Quadrupole-Linear Ion Trap Mass Spectrometer for Quantifying Proteins," http://docs.appliedbiosystems.com/pebiodocs/00113936.pdf, 2004.

Hwang, S. et al., "Quantitative Proteomic Analysis of Nuclear Proteins During Apoptosis Using Stable Isotope Labeling," 52nd Conference of the American Society for Mass Spectrometry, May 24-27, 2004, Nashville, Tennessee.

Jedrzejewski, P. T. et al., "De Novo Sequencing of Protease Inhibitors from Libraries Following Affinity Selection Mass Spectrometry," 52nd Conference of the American Society for Mass Spectrometry, May 24-27, 2004, Nashville, Tennessee.

Julka et al., "Quantification in Proteomics Through Stable Isotope Coding: A Review," Journal of Proteome Research, 3: 350-363, 2004.

Krokhin et al., "An Improved Model for Prediction of Retention Times of Tryptic Peptides in Ion Pair Reversed-Phase HPLC," Molecular & Cellular Proteomics, 3: 908-919, 2004.

Kuhn et al., "Quantification of C-Reactive Protein in the Serum of Patients with Rheumatoid Arthritis Using Multiple Reaction Monitoring Mass Spectrometry and 13C-Labeled Peptide Standards," Proteomics, 4:1-12, 2004.

Lisek et al., "Quantitation of Endogenous Substance P by On-Line Microcolumn Liquid Chromatography/Continuous-Flow Fast-Atom Bambardment Mass Spectrometry," Rapid Communications in Mass Spectrometry, 3(2): 43-46, 1989.

(56) References Cited

OTHER PUBLICATIONS

Liu et al., "High Throughput Quantitative Proteome Analysis Using Trysin Catalyzed 18O Labeling, Thiol-Specific Enrichment, and Accurate Mass and Time Tags," 52nd Conference of the American Society for Mass Spectrometry, May 24-27, 2004, Nashville, Tennessee.

Lubeck et al., "Differential Proteomics Based on LC MS(n) Data Without Labeling," 52nd Conference of the American Society for Mass Spectrometry, May 24-27, 2004, Nashville, Tennessee.

Lucas, D. A. et al., "Quantitative Proteomic Analysis of Inorganic Phosphate-Induced MC3T3 El Osteoblast Cells," 52nd Conference of the American Society for Mass Spectrometry, May 24-27, 2004, Nashville, Tennessee.

Nisar, S. et al., "Nanoelectrospray Ionization Tandem Mass Spectrometric Identification of Cytochrome P450s in Human Liver and Colorectal Metastases," 52nd Conference of the American Society for Mass Spectrometry, May 24-27, 2004, Nashville, Tennessee.

Qu, J. et al., "Determination of MPL Induced Tyrosine Aminotransferase Level Changes in Rat Liver Using Liquid Chromatography Tandem Mass Spectrometry and ICAT," 52nd Conference of the American Society for Mass Spectrometry, May 24-27, 2004, Nashville, Tennessee.

Ross, P. et al., "Relative and Absolute Quantitation in Yeast Proteomics Using Multiplexed Isobaric Peptide Tags," 52nd Conference of the American Society for Mass Spectrometry, May 24-27, 2004, Nashville, Tennessee.

Schaefer, J. et al., "An Elegant, Gel-Free Strategy for Quantitative Protein Profiling Using Isotope Labeled PST Tags (qPST)," 52nd Conference of the American Society for Mass Spectrometry, May 24-27, 2004, Nashville, Tennessee.

Scrivener et al., "Peptidomics: A New Approach to Affinity Protein Microarrays," Proteomics, 3:122-128, 2003.

Stemmann, et al., "Dual Inhibition of Sister Chromatid Separation at Metaphase," Cell, 107: 715-726, 2001.

Wang, G. et al., "Relative Quantification of Highly Complex Proteomes Using Liquid Chromatography and Nano-Spray Tandem Mass Spectrometry," 52nd Conference of the American Society for Mass Spectrometry, May 24-27, 2004, Nashville, Tennessee.

Whitelegge et al., "Can Isotope Ratio Be Reliably Measured from Peptide Isotope Distributions for Stable-Isotope Coding in Proteomics," 52nd Conference of the American Society for Mass Spectrometry, May 24-27, 2004, Nashville, Tennessee.

Wu et al., "An Automated MALDI Mass Spectrometry Approach for Optimizing Cyclosporin Extraction and Quantitation," Analytical Chemistry, 69(18): 3767-3771, 1997.

Zhang et al., "Quantitation of Human Glutathione S-Transferases in Complex Matrices by Liquid Chromatography/Tandem Mass Spectrometry with Signature Peptides," Rapid Communications in Mass Spectrometry, 18:491-498, 2004.

LaBaer, "So, You Want to Look for Biomarkers (Introducation to the Special Biomarkers Issue)," Journal of Proteome Research, 4: 1053-1059, 2005.

Applied Biosystems iTRAQ Reagents, Amine-Modifying Labeling Reagents for Multiplexed Relative and Absolute Protein Quantification, Chemistry Reference Guide, May 2004.

Ross et al., "Multiplexed Protein Quantification in *Saccharymyces cerevisiae* Using Amine-Reactive Isobaric Tagging Reagents," Molecular & Cellular, 3: 1154-1169, 2004.

International Search Report for Application No. PCT/US2006/004548, date of mailing Dec. 6, 2008.

Written Opinion of International Searching Authority, PCT/US2006/004548, date of mailing Dec. 6, 2008.

Unwin et al., "Multiple Reaction Monitoring to Identify Sites of Protein Phosphorylation with High Sensitivity," Mol Cell Proteomics, 4: 1134-44, 2005.

Office Action from U.S. Appl. No. 11/501,675, now abandoned, date of mailing Dec. 9, 2008.

Office Action from U.S. Appl. No. 11/501,675, now abandoned, date of mailing Mar. 20, 2009.

Office Action from U.S. Appl. No. 11/350,147, now abandoned, date of mailing Dec. 15, 2008.

Office Action from U.S. Appl. No. 11/350,147, now abandoned, date of mailing Apr. 7, 2009.

Cong et al., "Simultaneous Proteomic Profiling of Four Different Growth States of Human Fibroblasts, using amine-reactive isobaric tagging reagents and tandem mass spectrometry" Mechanisms of Ageing and Development, Elsevier Sequioa, Lausanne, Ch. vol. 127 Apr. 4, 2006, pp. 332-343.

Cong et al., "Simultaneous Proteomic Profiling of Four Different Growth States of Human Fibroblasts, using amine reactive isobaric tagging reagents and tandem mass spectrometry" Mechanisms of Ageing and Develpment, Elsevier Sequioa, Lausanne, 127:332-343 (2006).

Effkemann et al., "Triple-quadrupole LC-MS-MS for quantitative determination of nitrofuran metabolites in complex food matrixes," Anal Bioanal Chem, 378:842-844 (2004).

Leitner et al., "Determination of the metabolites of nitrofuran antibiotics in animal tissue by high-performance liquid chromatography-tandem mass spectrometry," J. Chromatogr A., 939:49-58 (2001).

Various Authors, "Abstracts Presented at the 50th Annual Meeting of the Canadian Society of Clinical Chemists" Chemical Biochemistry vol. 39, Jun. 6, 2006, p. 1092.

* cited by examiner

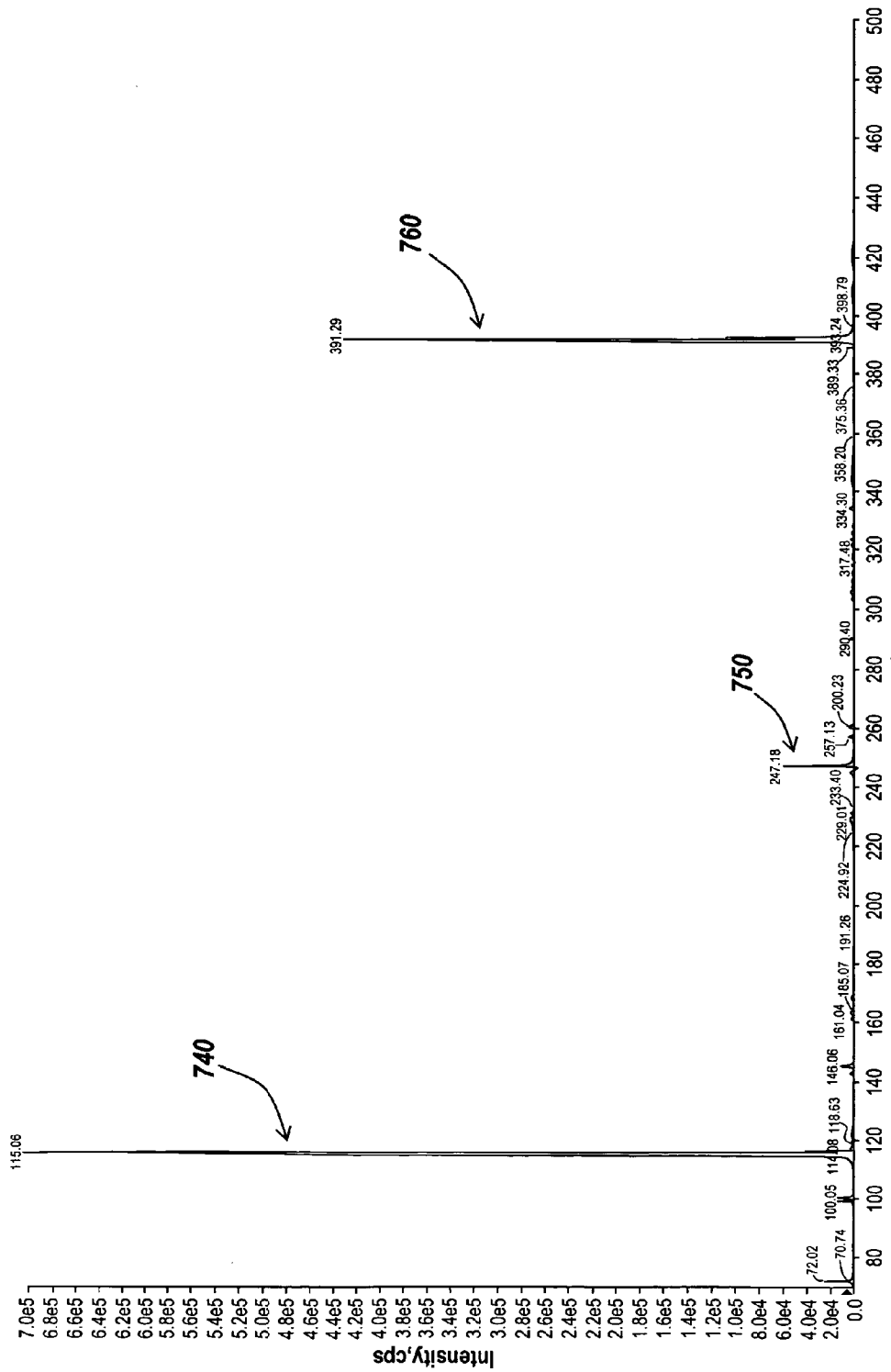

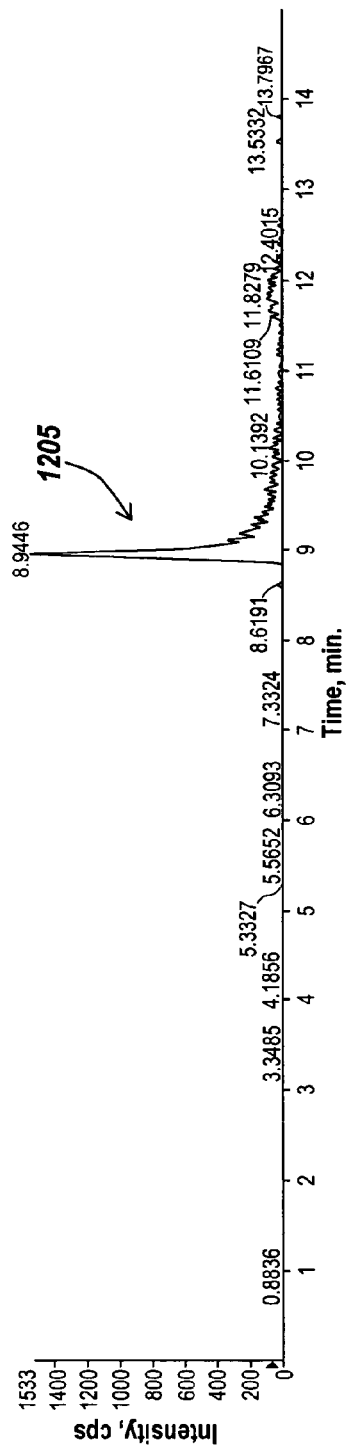
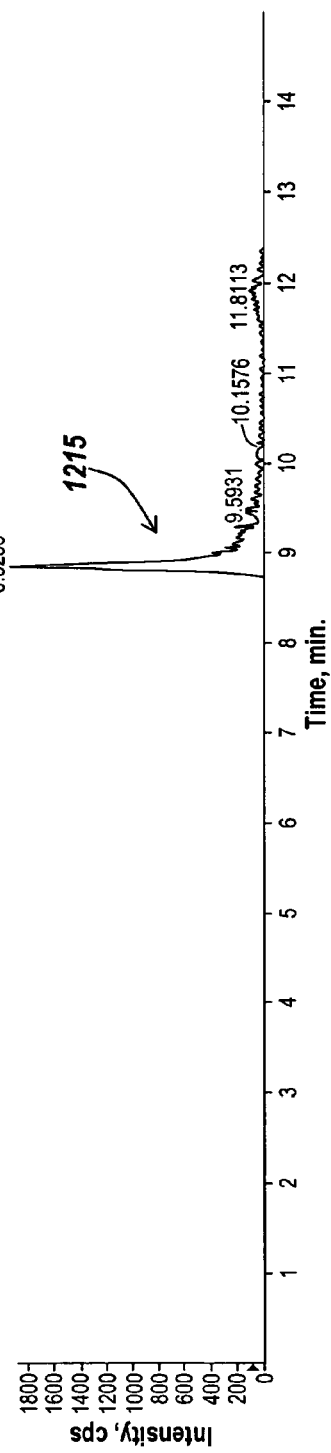
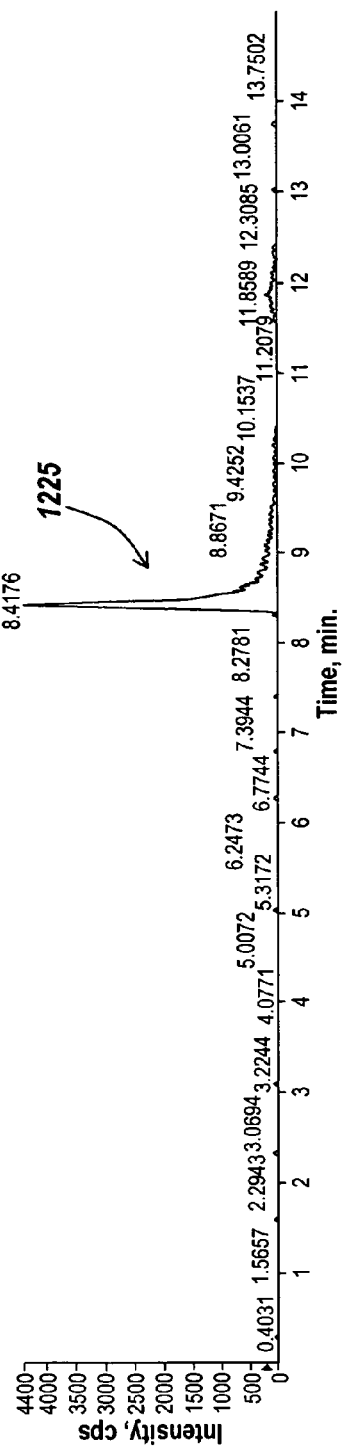
Fig. 12A
Fig. 12B
Fig. 12C

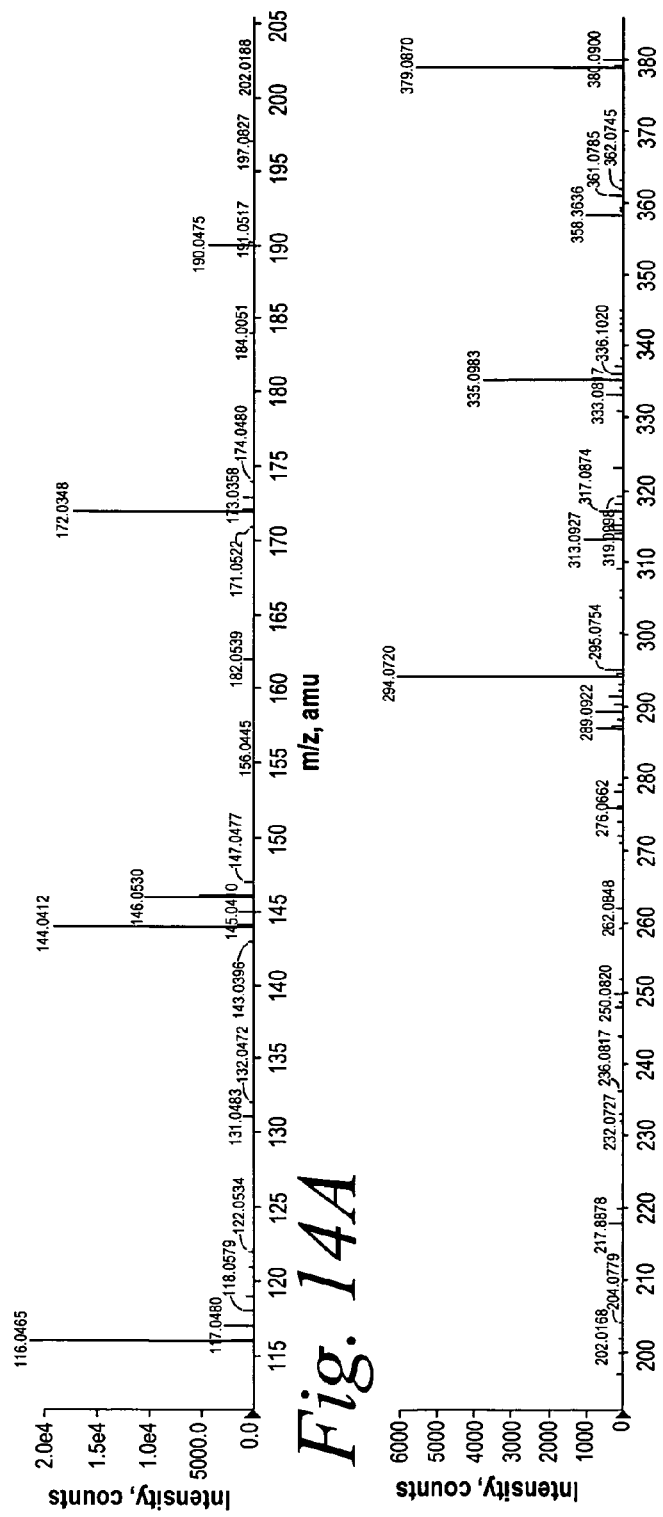
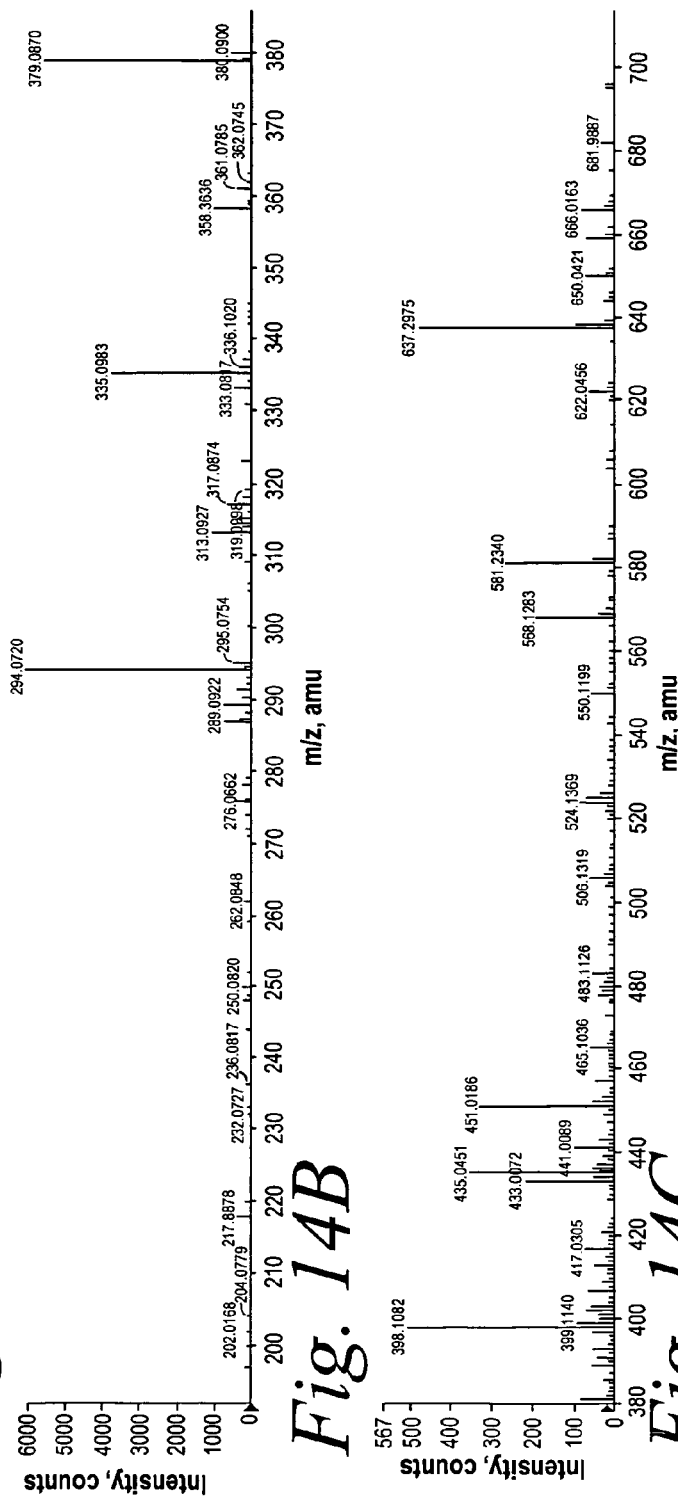
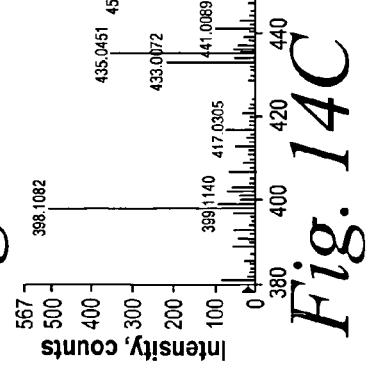
Fig. 14A
Fig. 14B
Fig. 14C

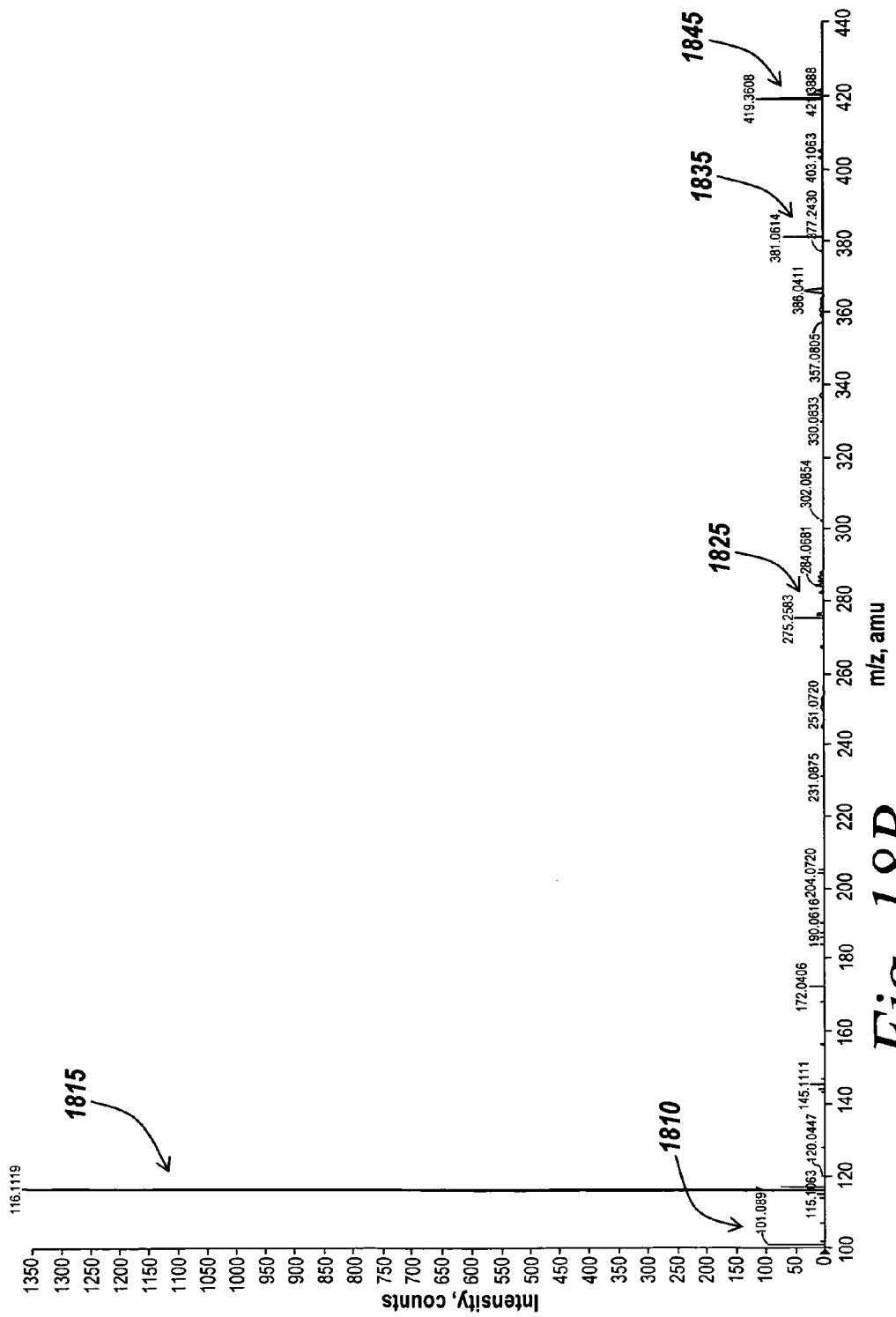

AMINE-CONTAINING COMPOUND ANALYSIS METHODS

CROSS-REFERENCE TO RELATED APPLICATIONS

The present application is a continuation and claims the right of priority under 35 U.S.C. §120 to U.S. application Ser. No. 11/350,147, entitled "Amine-containing Compound Analysis Methods" filed Feb. 8, 2006, which claims priority under 35 U.S.C. §119(e) to U.S. Provisional Application No. 60/651,734, entitled "Amine-containing Compound Analysis Methods", filed Feb. 9, 2005, both of which are commonly owned with the instant application and both of which are hereby expressly incorporated by reference in their entirety as though fully set forth herein.

INTRODUCTION

Amine-containing compounds represent important biological and medicinal chemicals. Examples of amine-containing compounds include proteins, peptides, polyamines, amino acids, catecholamines and nitrofuran metabolites. Current methods for the quantitation of amine-containing compounds include high performance liquid chromatography (HPLC) with ultra-violet (UV) fluorescent, or electrochemical detection, liquid chromatography in conjunction with mass spectrometry (LC/MS) and tandem mass spectrometry (MS/MS).

Absolute quantitation of amine-containing compounds by the above-mentioned methods can be problematic. For example, in order to analyze many amine-containing compounds by HPLC, a difficult and time-consuming derivatization step must be performed before analysis occurs. In addition, HPLC has the drawbacks of long analysis times, high run-to-run deviations, a lack of multiplexing capability and non-specificity.

The more recent use of LC/MS and MS/MS for the detection and quanititation of amine-containing compounds offers the advantage of increased sensitivity and specificity and the ability to rapidly measure multiple amine-containing compounds in one sample; however, these techniques also lack a multiplexing capability. In order to perform absolute quantitation, expensive isotopically enriched compounds are used as internal standards, which are incompatible with some tandem mass spectrometry methods.

SUMMARY

The present teachings provide methods for the analysis of one or more of amine-containing compounds in one or more samples using isobaric labels and parent-daughter ion transition monitoring (PDITM). In various aspects, the present teachings provide methods for determining the relative concentration, absolute concentration, or both, of one or more amine-containing compounds in one or more samples. In various embodiments, the present teachings provide methods whereby the relative concentration, absolute concentration, or both, of multiple amine-containing compounds in a sample, one or more amine-containing compounds in multiple samples, or combinations thereof, can be determined in a multiplex fashion.

The amine-containing compounds, to which various embodiments of the present teachings can be applied, can come from a wide variety of sources such as, for example, physiological fluid samples, cell or tissue lysate samples, protein samples, cell culture samples, fermentation broth media samples, agricultural product samples, animal product samples, animal feed samples, samples of food or beverage for human consumption, and combinations thereof. The present teachings, in various embodiments, can be applied to a wide variety of primary amine-containing compounds, including, but not limited to, amino acids, catecholamines, nitrofuran metabolites, polyamines, peptides, proteins, polypeptides, and combinations thereof.

The phrases "set of isobaric labels", "set of isobaric tags" are used interchangeably and refer to, for example, a set of reagents or chemical moieties where the members of the set (i.e., an individual "isobaric label" or "isobaric tag") have substantially the same mass but where each member of the set can produce a different daughter ion signal upon being subjected to ion fragmentation (e.g., by collision induced dissociation (CID), photoinduced dissociation (PID), etc.). A daughter ion of a isobaric tag or label that can be used to distinguish between members of the set can be referred to as a reporter ion of the isobaric tag or label. In various embodiments, a set of isobaric tags comprises amine-derivatized amine-containing compounds that are substantially chromatographically indistinguishable and substantially indistinguishable mass spectrometrically in the absence of fragmentation, but which produce strong low-mass MS/MS signature ions following CID.

The term "parent-daughter ion transition monitoring" or "PDITM" refers to, for example, a measurement using mass spectrometry whereby the transmitted mass-to-charge (m/z) range of a first mass separator (often referred to as the first dimension of mass spectrometry) is selected to transmit a molecular ion (often referred to as "the parent ion" or "the precursor ion") to an ion fragmentor (e.g. a collision cell, photodissociation region, etc.) to produce fragment ions (often referred to as "daughter ions") and the transmitted m/z range of a second mass separator (often referred to as the second dimension of mass spectrometry) is selected to transmit one or more daughter ions to a detector which measures the daughter ion signal. The combination of parent ion and daughter ion masses monitored can be referred to as the "parent-daughter ion transition" monitored. The daughter ion signal at the detector for a given parent ion-daughter ion combination monitored can be referred to as the "parent-daughter ion transition signal". In various embodiments of the present teachings, the parent ion is a amine-containing compound labeled with an isobaric tag and the daughter ion is a reporter ion of the isobaric tag; accordingly, the ion signal of a reporter ion that is measured at a detector for a given isobarically labeled amine-containing compound parent ion can be referred to as a "amine-containing compound-reporter ion transition signal". Similarly, the ion signal of a reporter ion that is measured at a detector for a given isobarically labeled standard compound can be referred to as a "standard compound-reporter ion transition signal".

For example, one embodiment of parent-daughter ion transition monitoring is multiple reaction monitoring (MRM) (also referred to as selective reaction monitoring). In various embodiments of MRM, the monitoring of a given parent-daughter ion transition comprises using as the first mass separator (e.g., a first quadrupole parked on the parent ion m/z of interest) to transmit the parent ion of interest and using the second mass separator (e.g., a second quadrupole parked on the daughter ion m/z of interest) to transmit one or more daughter ions of interest. In various embodiments, a PDITM can be performed by using the first mass separator (e.g., a quadrupole parked on a parent ion m/z of interest) to transmit parent ions and scanning the second mass separator over a m/z range including the m/z value of the one or more daughter ions of interest.

For example, a tandem mass spectrometer (MS/MS) instrument or, more generally, a multidimensional mass spectrometer (MS$^n$) instrument, can be used to perform PDITM, e.g., MRM. Examples of suitable mass analyzer systems include, but are not limited to, those that comprise one or more of a triple quadrupole, a quadrupole-linear ion trap, a quadrupole TOF, and a TOF-TOF In various aspects, the present teachings provide methods for analyzing one or more amine-containing compounds in one or more samples using isobaric labels and parent-daughter ion transition monitoring (PDITM). In various embodiments, a method comprises the steps of: (a) labeling one or more amine-containing compounds each with a different isobaric tag from a set of isobaric tags, each isobaric tag from the set of isobaric tags comprising a reporter ion portion; (b) combining at least a portion of each of the isobarically labeled amine-containing compounds to produce a combined sample; (c) subjecting at least a portion of the combined sample to parent-daughter ion transition monitoring; (d) measuring the ion signal of one or more of the transmitted reporter ions; and (e) determining the concentration of one or more of the isobarically labeled amine-containing compounds based at least on a comparison of the measured ion signal of the corresponding reporter ion to one or more measured ion signals of a standard compound. Accordingly, in various embodiments, the concentration of multiple amine-containing compounds can be determined in a multiplex fashion, for example, by combining two or more isobarically labeled amine-containing compounds to produce a combined sample and subjecting the combined sample to PDITM, where reporter ions of two or more of isobarically labeled amine-containing compounds are monitored.

In various aspects, provided are methods for analyzing one or more amine-containing compounds in one or more samples comprising the steps of: (a) providing a standard compound; (b) labeling the standard compound with an isobaric tag from a set of isobaric tags; (c) labeling one or more amine-containing compounds each with a different isobaric tag from the set of isobaric tags; (d) combining at least a portion of the isobarically labeled standard compound with at least a portion of each of the isobarically labeled amine-containing compounds to produce a combined sample; (e) loading at least a portion of the combined sample on a chromatographic column; (f) subjecting at least a portion of the eluent from the chromatographic column to parent-daughter ion transition monitoring; (g) measuring the ion signal of one or more of the transmitted reporter ions; and; (h) determining the concentration of one or more of the amine-containing compounds of interest based at least on a comparison of the measured ion signal of the corresponding reporter ion to the measured ion signal of a reporter ion corresponding to the isobarically labeled standard compound.

In various aspects, provided are the methods for analyzing one or more amine-containing compounds in one or more samples comprising the steps of (a) labeling one or more amine-containing compounds each with a different isobaric tag from a set of isobaric tags; (b) combining at least a portion of each of the isobarically labeled amine-containing compounds to produce a combined sample; (c) loading at least a portion of the combined sample on a chromatographic column; (d) subjecting at least a portion of the eluent from the chromatographic column to parent-daughter ion transition monitoring; (e) measuring the ion signal of one or more of the transmitted reporter ions; and (f) determining the concentration of one or more of the isobarically labeled amine-containing compounds based at least on a comparison of the measured ion signal of the corresponding reporter ion to a concentration curve of a standard compound.

In various aspects, provided are a method for analyzing one or more amine-containing compounds in one or more samples comprising the steps of: (a) labeling one or more amine-containing compounds each with a different isobaric tag from a set of isobaric tags; (b) combining at least a portion of each of the isobarically labeled amine-containing compounds to produce a combined sample; (c) subjecting at least a portion of the combined sample to parent-daughter ion transition monitoring using matrix assisted laser desorption ionization; (d) measuring the ion signal of one or more of the transmitted reporter ions; and (e) determining the concentration of one or more of the isobarically labeled amine-containing compounds based at least on a comparison of the measured ion signal of the corresponding reporter ion to the measured ion signal of a standard compound.

In various embodiments, a concentration curve of a standard compound can be generated by: (a) providing a standard compound having a first concentration; (b) labeling the standard compound with an isobaric tag from a set of isobaric tags; (c) loading at least a portion of the isobarically labeled standard compound on a chromatographic column; (d) subjecting at least a portion of the eluent from the chromatographic column to parent-daughter ion transition monitoring; (e) measuring the ion signal of the transmitted reporter ions; (f) repeating steps (a)-(e) for one or more different standard compound concentrations; and (g) generating a concentration curve for the standard compound based at least on the measured ion signal of the transmitted reporter ions at two or more standard compound concentrations.

In various embodiments, the step of determining the concentration of one or more isobarically labeled amine-containing compounds comprises determining the absolute concentration of one or more of the isobarically labeled amine-containing compounds.

Although, e.g., isotopically enriched amino acids can be used as internal standards for absolute quantitation of amino acid concentrations, one drawback of using stable isotope analogs of amino acids in MALDI mass spectrometry is that in some cases matrix related signals can interfere in the m/z region of interest of the amino acid. For example cyano-4-hydroxy cinnamic acid (CHCA) related signal at about m/z=147 can interfere with lysine and its stable isotope analog, similarily dihydroxybenzoic acid (DHB) related signal at about m/z=175 can interfere with arginine and its stable isotope analog. In various embodiments, the present teaching provide methods using isobaric tags and PDITM that facilitates reducing interference of matrix related signals with those from an internal standard or amine-containing compound of interest.

In various embodiments, the one or more amine-containing compounds of interest comprises one or more of lysine, an isomer of lysine and a post-translationally modified lysine, and the matrix comprises a cyano-4-hydroxy cinnamic acid (CHCA). In various embodiments, the one or more amine-containing compounds of interest comprises one or more of arginine, an isomer or arginine, a post-translationally modified arginine and combinations thereof, and the matrix comprises a dihydroxybenzoic acid (DHB).

In various aspects, provided are assays designed to determine the presence of an amine-containing compound of interest in one or more samples. The assay can be, for example, a biomarker validation assay, used to aid in the discovery of various biochemical pathways, for drug discovery or a diagnostic assay. The assay can, for example, be diagnostic of a disease or condition, prognostic of a disease or condition, or both.

In various aspects, the present teachings provide articles of manufacture where the functionality of a method of the present teachings is embedded as computer-readable instructions on a computer-readable medium, such as, but not limited to, a floppy disk, a hard disk, an optical disk, a magnetic tape, a PROM, an EPROM, CD-ROM, or DVD-ROM.

The forgoing and other aspects, embodiments, and features of the teachings can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the teachings.

BRIEF DESCRIPTIONS OF THE DRAWINGS

FIG. 1 is a schematic diagram of various embodiments of methods of analyzing one or more amine-containing compound in one or more samples.

FIG. 2 schematically illustrates various embodiments of an isobaric tag.

Figure 6A:
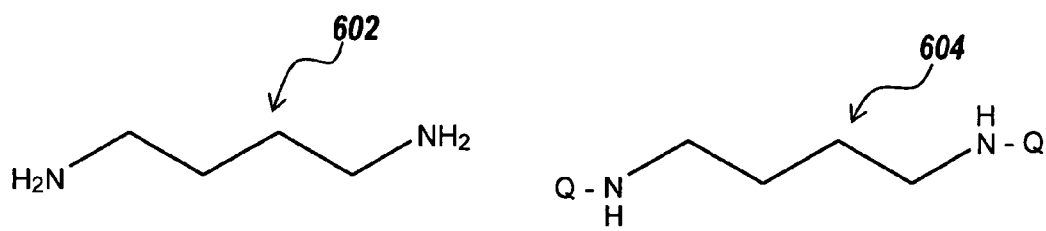
Figure 6B:
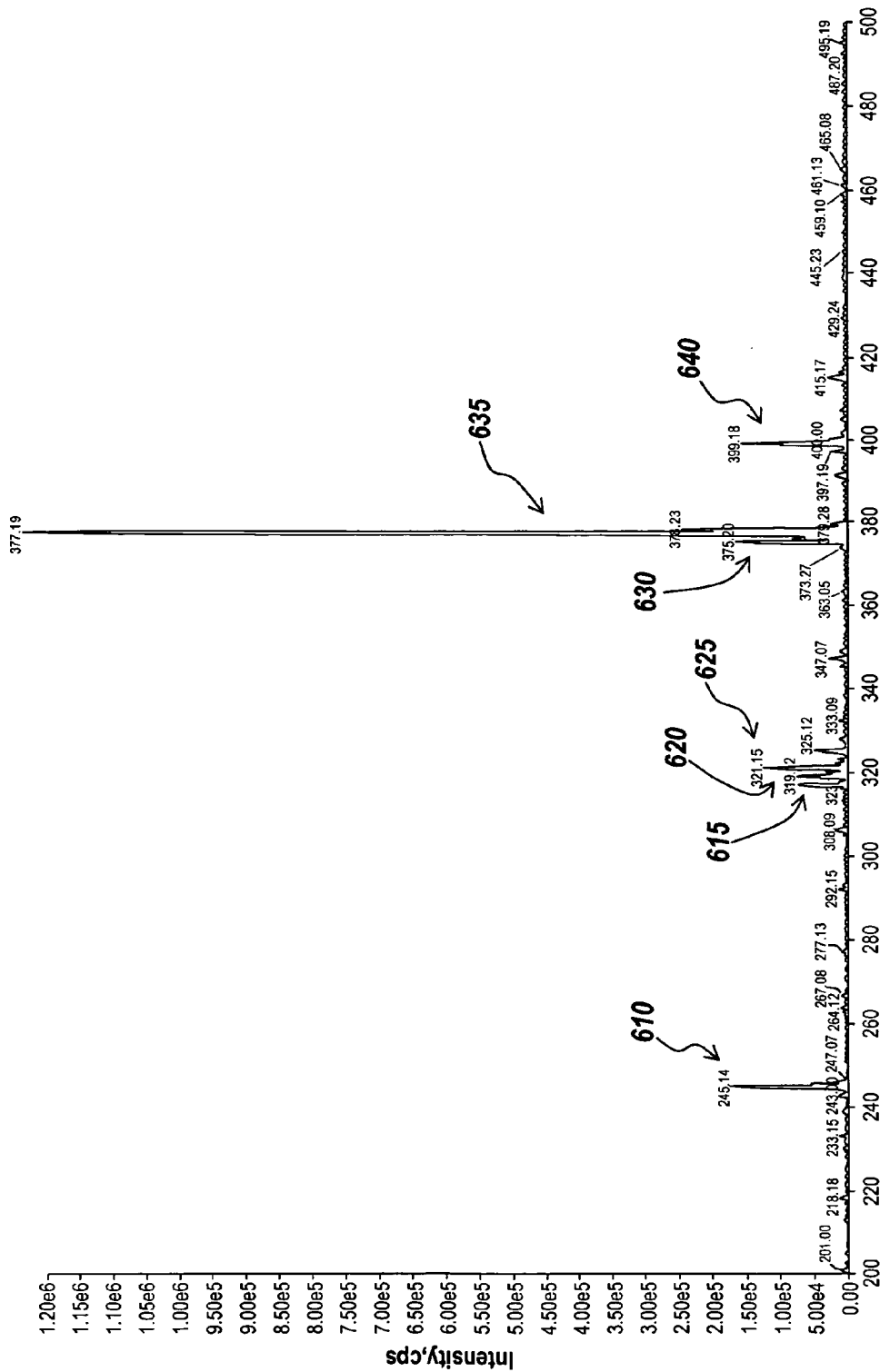
Figure 6C:
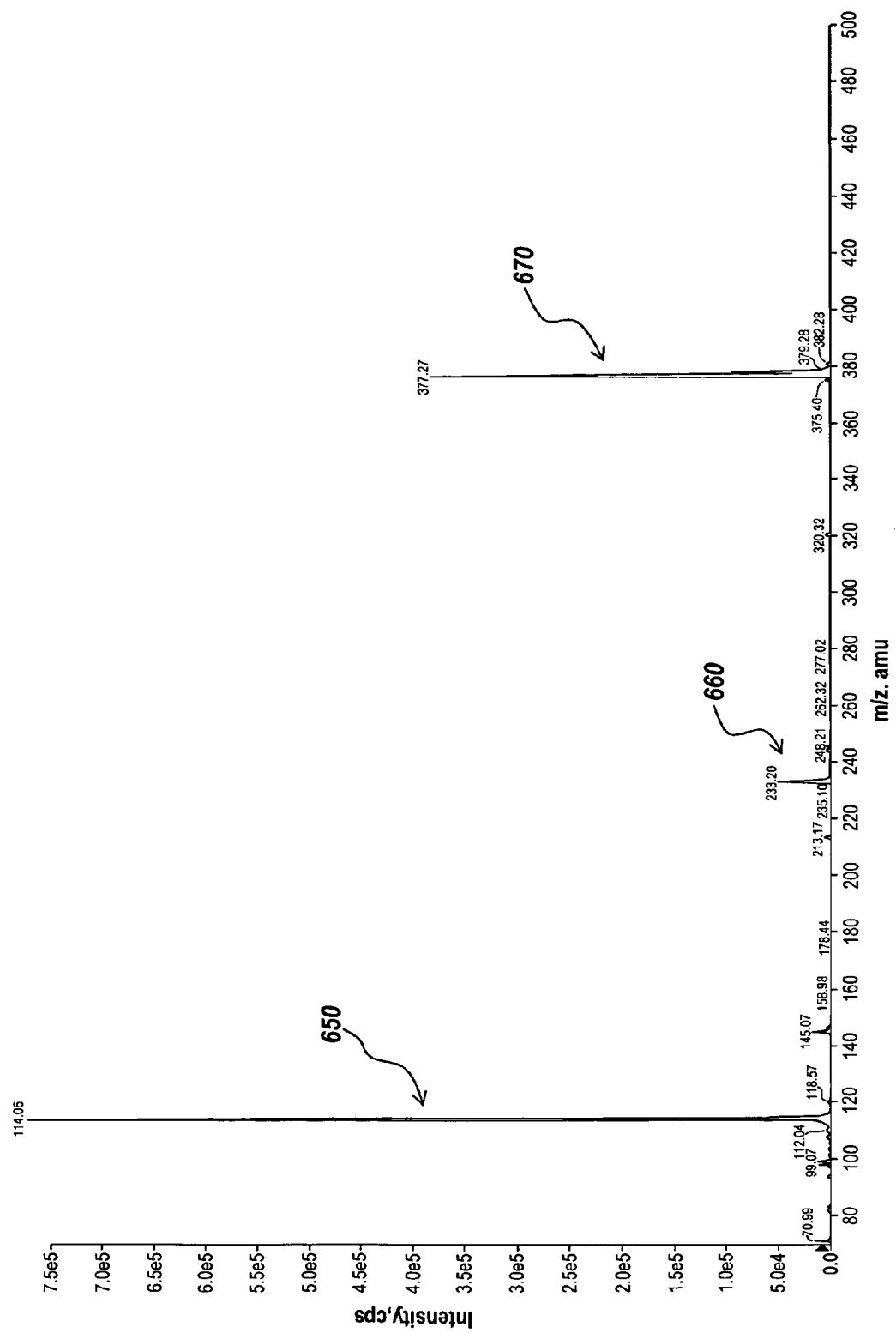

FIG. 6A schematically depicts the structure of unlabeled putrescine and putrescine labeled with an iTRAQ™ brand reagent, and FIGS. 6B and 6C depict mass spectra of isobarically labeled putrescine before and after PDITM.

Figure 7A:
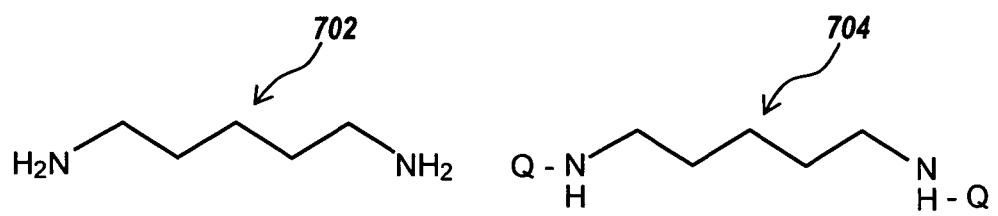
Figure 7B:
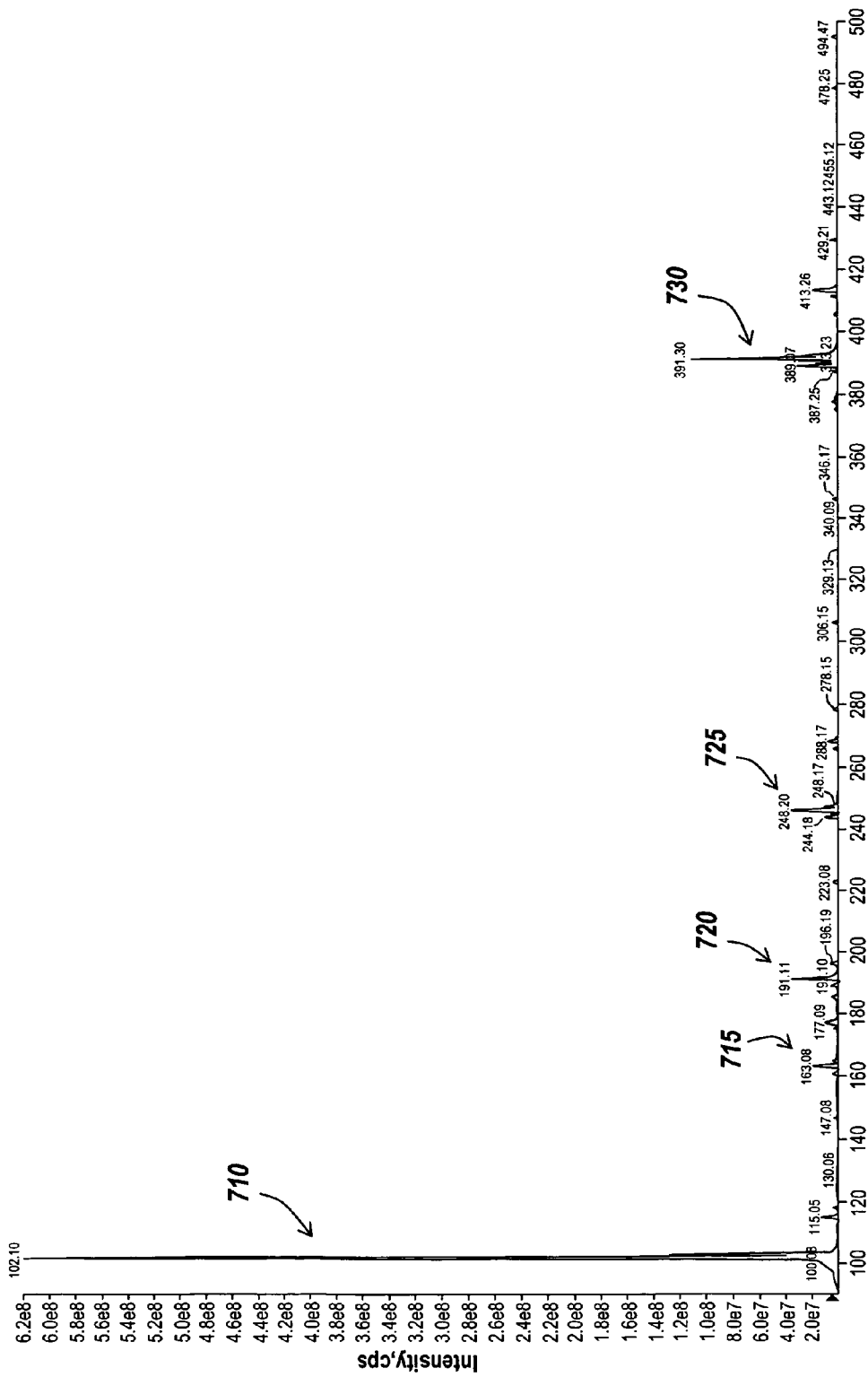

FIG. 7A schematically depicts the structure of unlabeled cadaverine and cadaverine labeled with an iTRAQ™ brand reagent, and FIGS. 7B and 7C depict mass spectra of isobarically labeled cadaverine before and after PDITM.

Figure 8A:
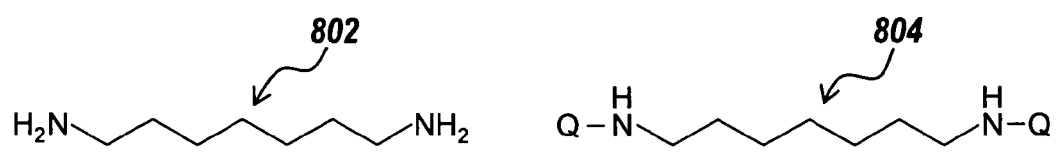
Figure 8B:
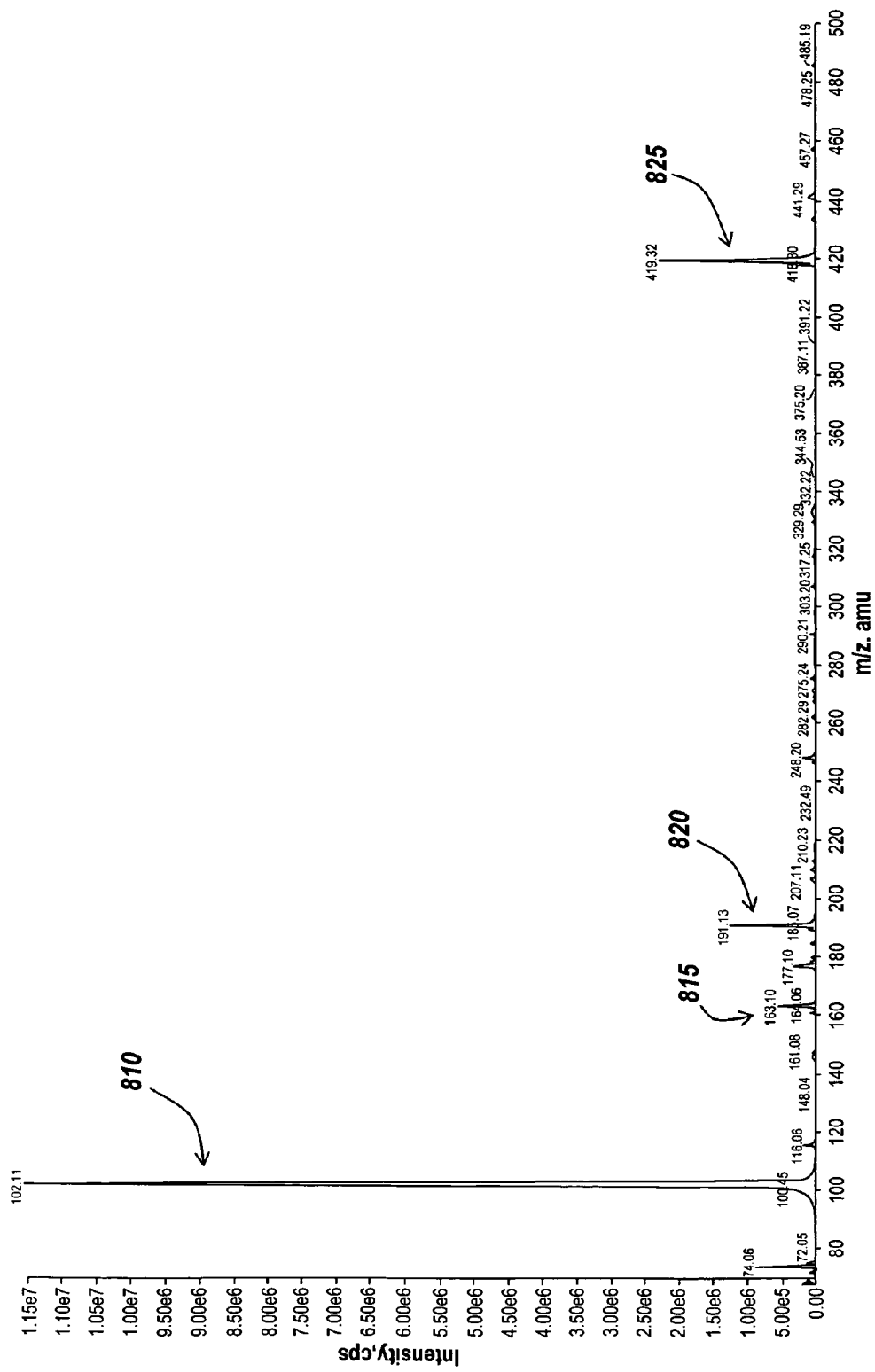
Figure 8C:
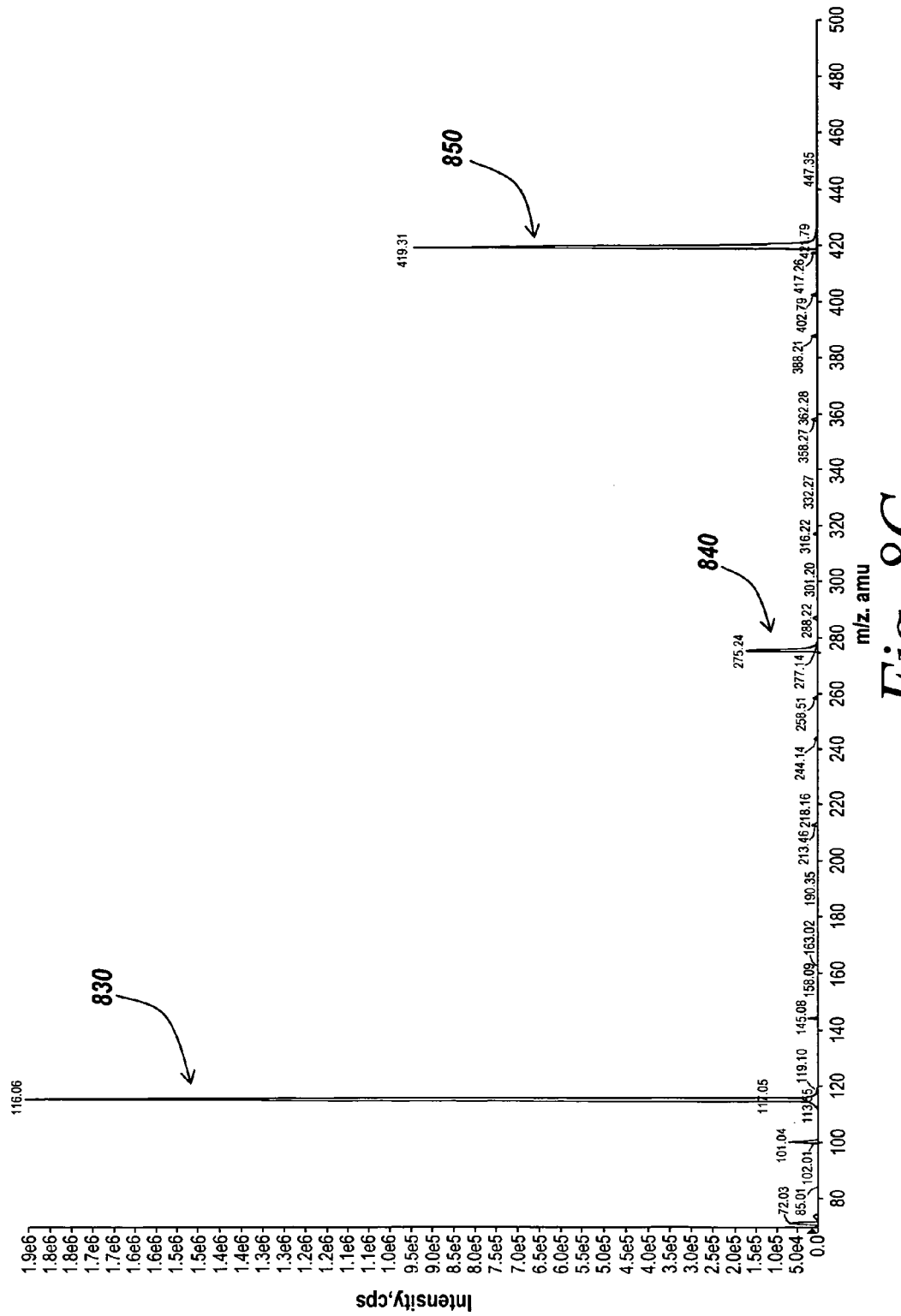

FIG. 8A schematically depicts the structure of unlabeled 1,7-diaminoheptane and 1,7-diaminoheptane labeled with an iTRAQ™ brand reagent, and FIGS. 8B and 8C depict mass spectra of isobarically labeled 1,7-diaminoheptane before and after PDITM.

Figure 9A:
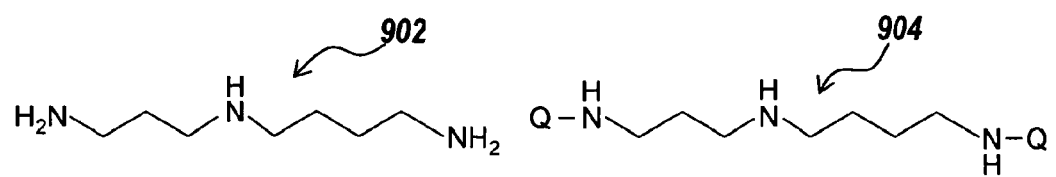
Figure 9B:
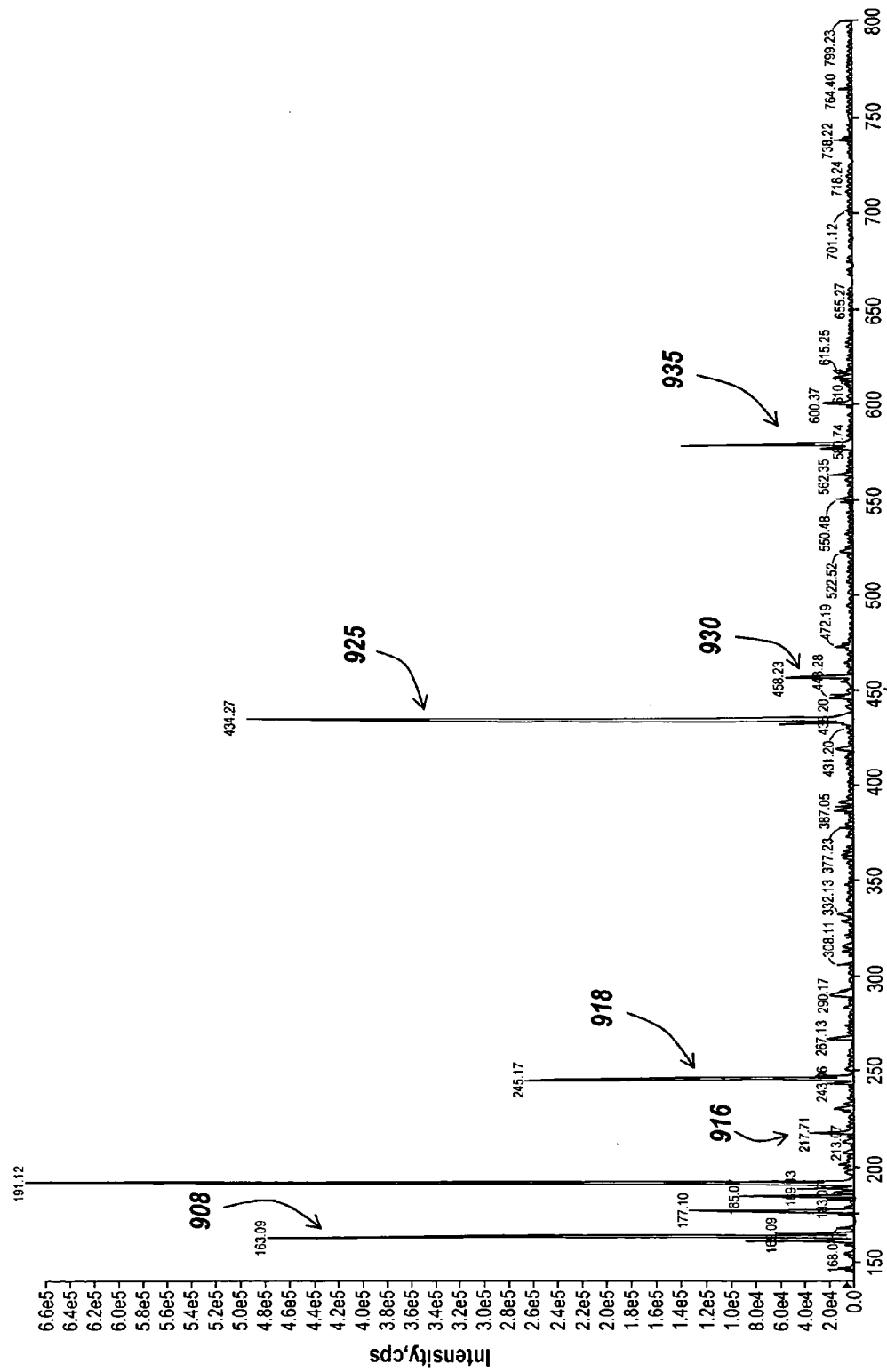
Figure 9C:
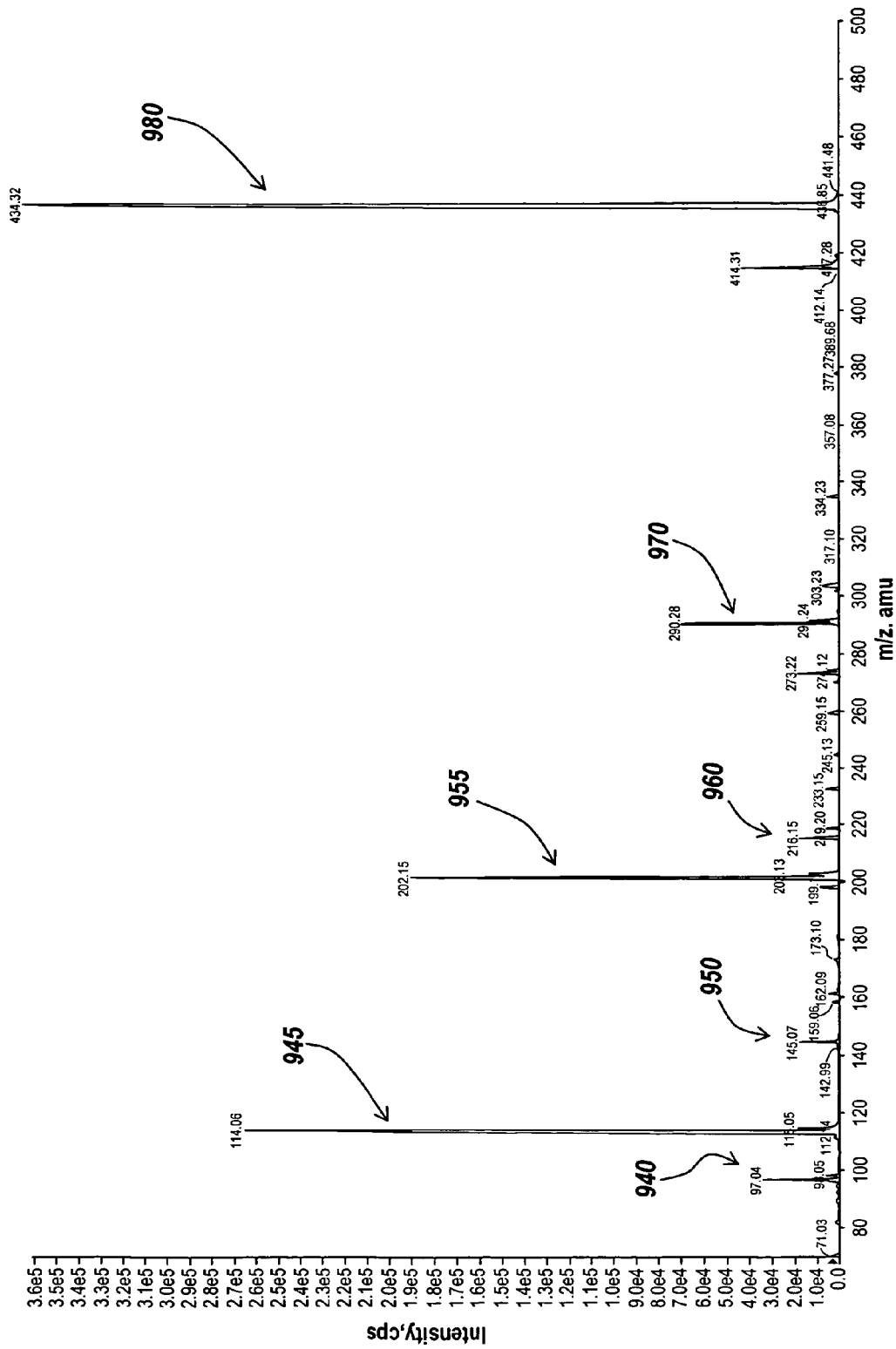
Figure 9D:
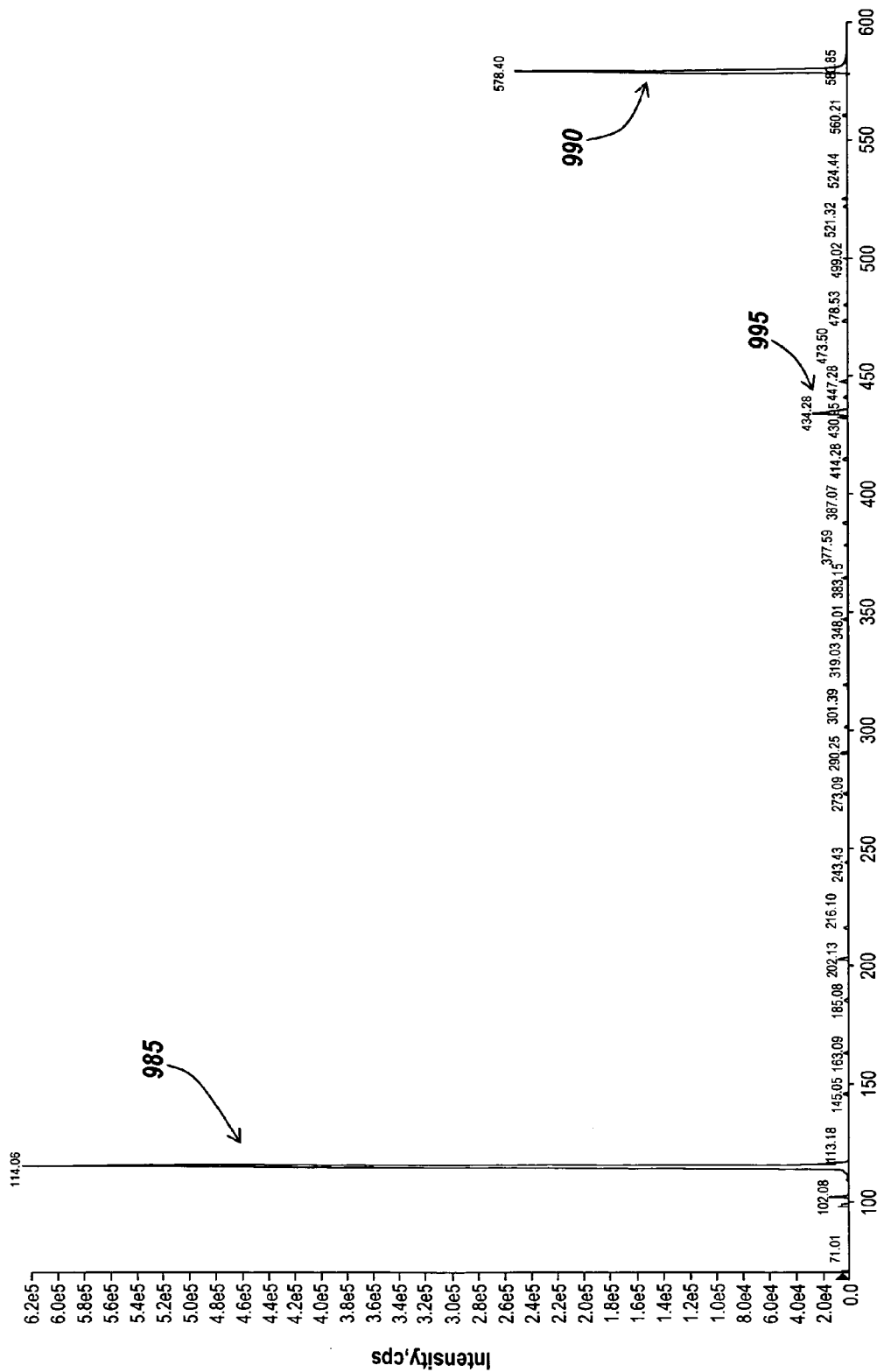

FIG. 9A schematically depicts the structure of unlabeled spermidine and spermidine labeled with an iTRAQ™ brand reagent, and FIGS. 9B, 9C and 9D depict mass spectra of isobarically labeled spermidine before and after PDITM.

Figure 10A:
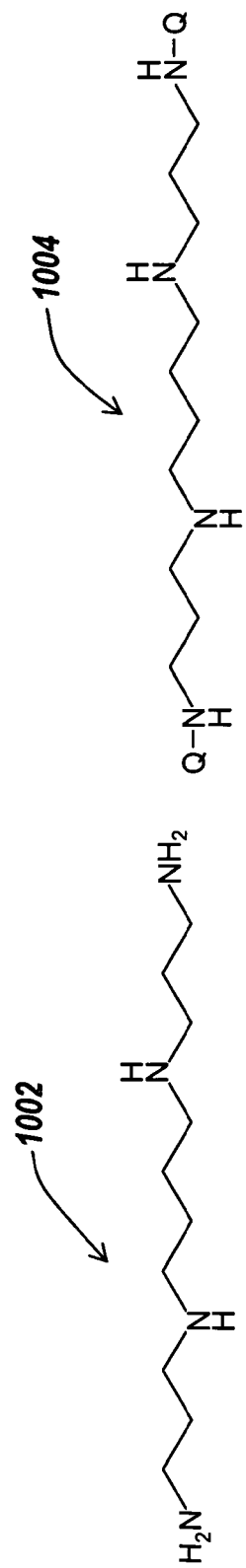
Figure 10B:
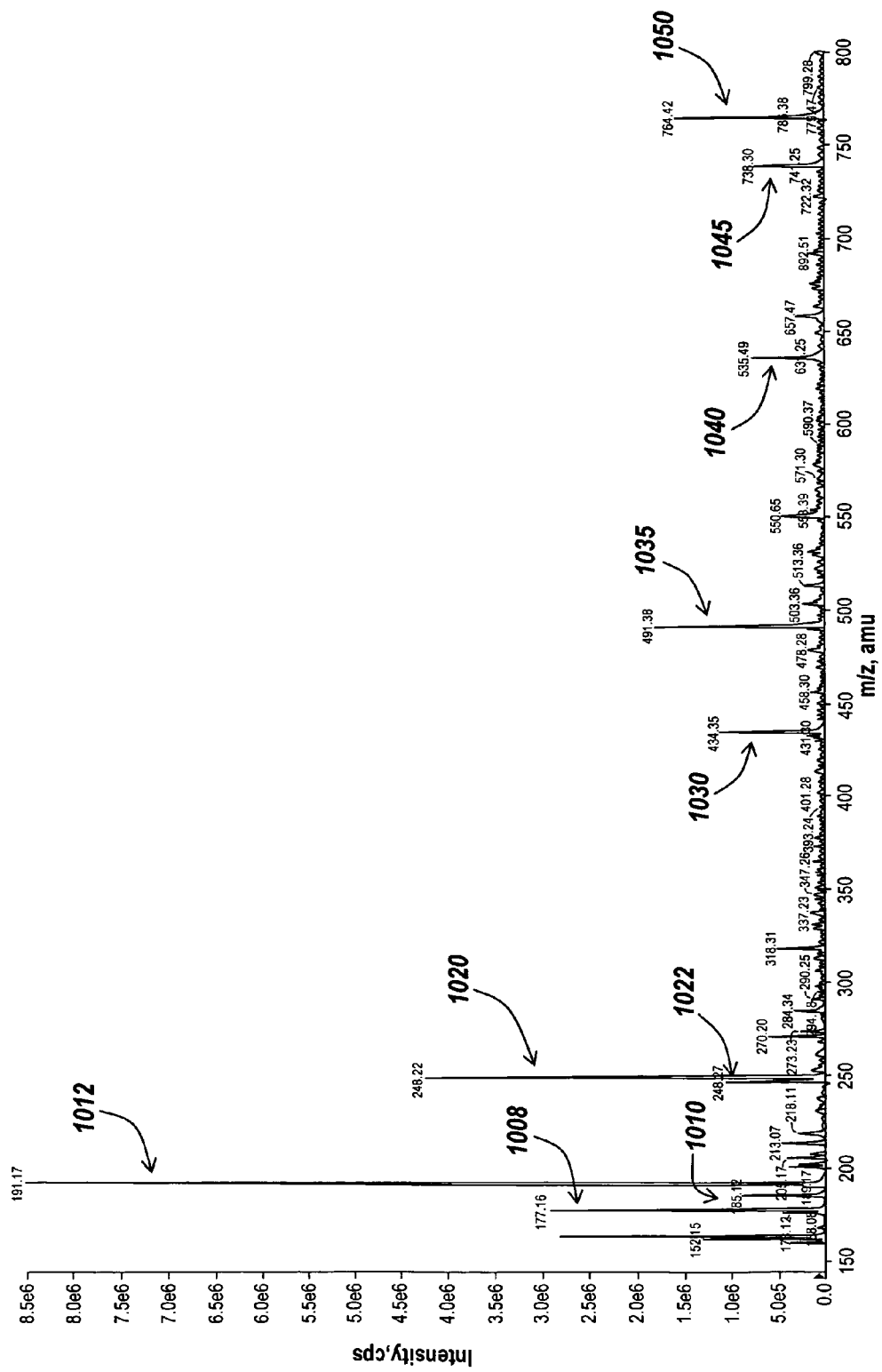
Figure 10C:
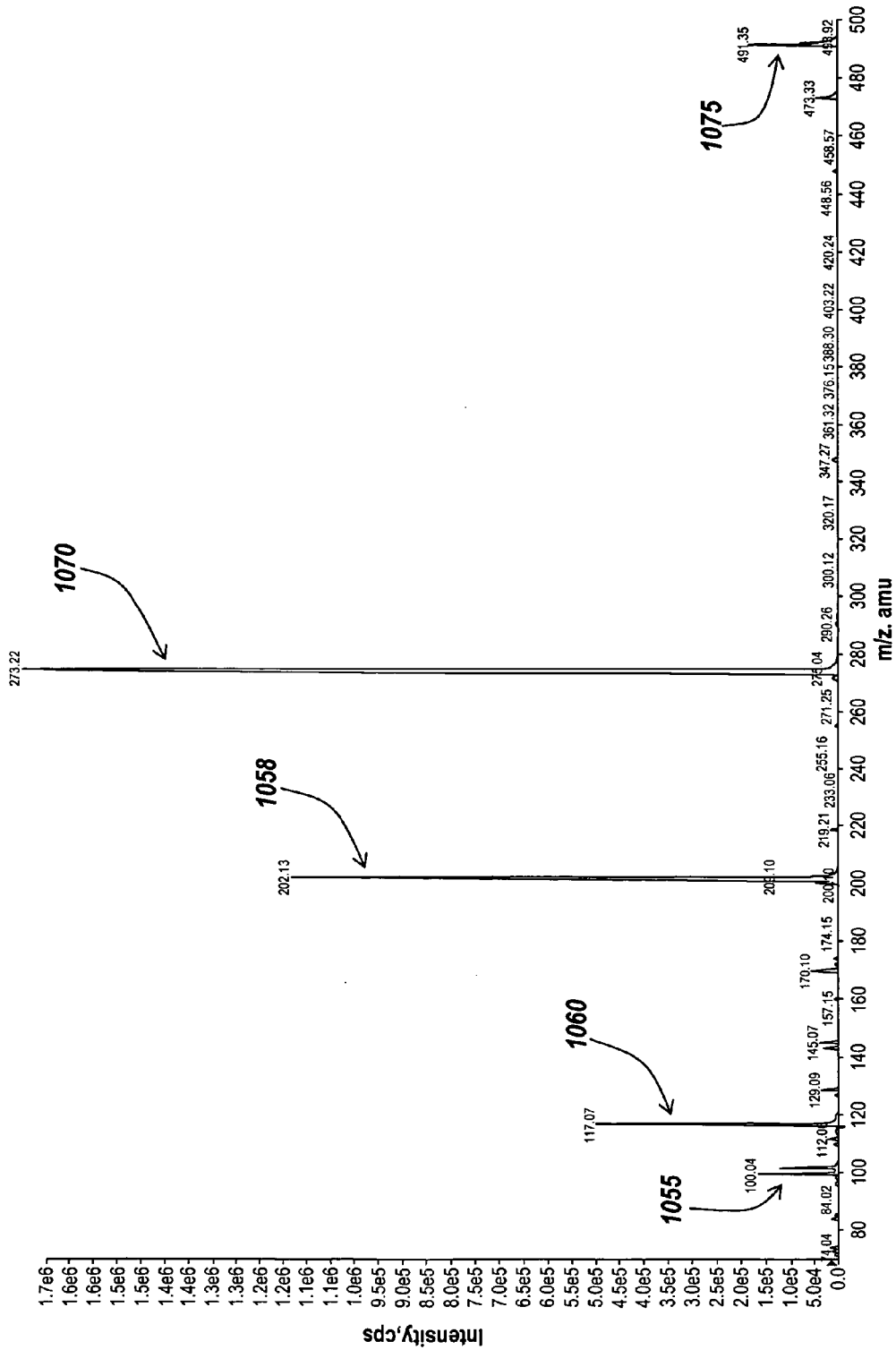
Figure 10D:
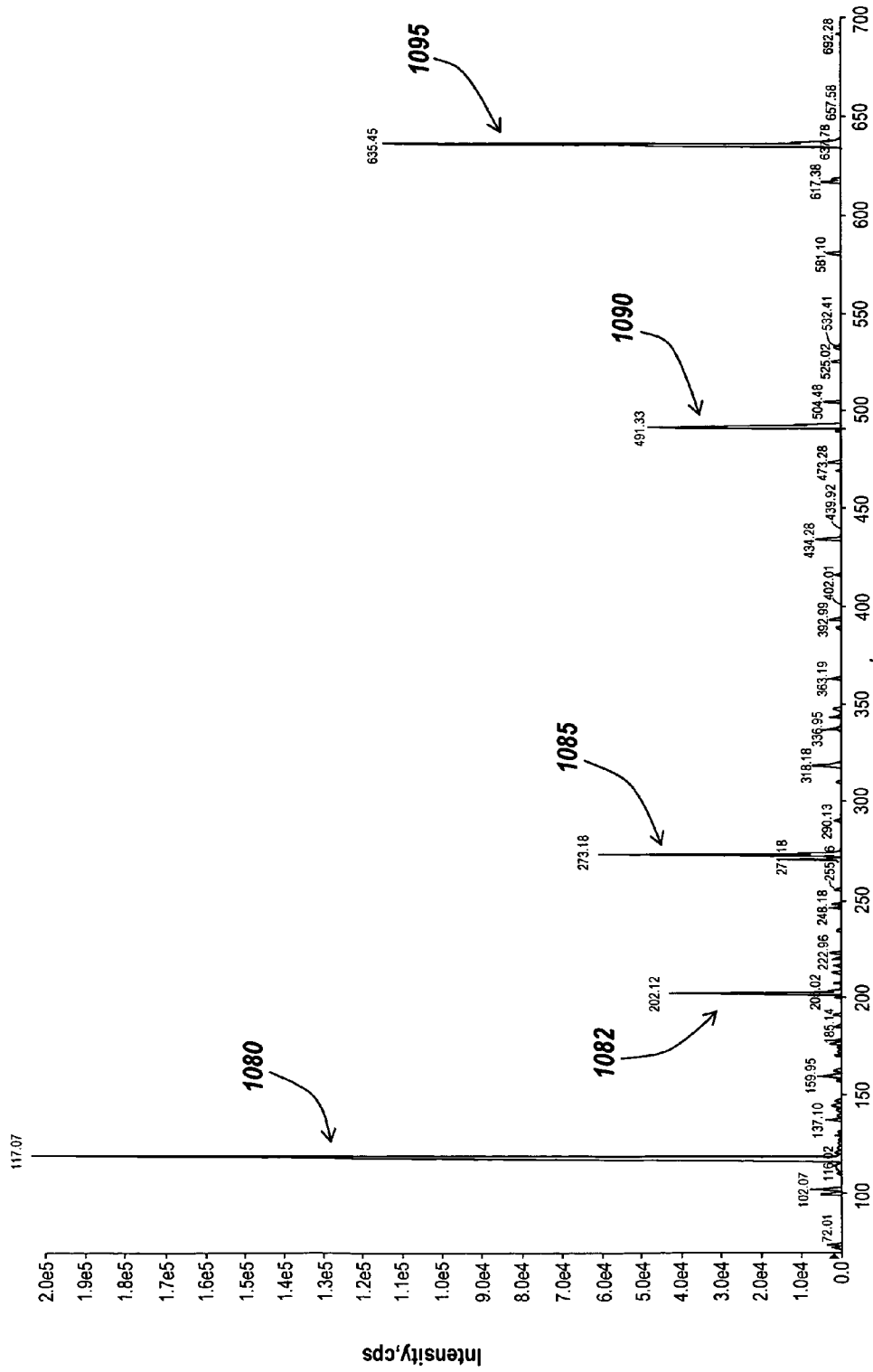

FIG. 10A schematically depicts the structure of unlabeled spermine and spermine labeled with an iTRAQ™ brand reagent, and FIGS. 10B, 10C and 10D depict mass spectra of isobarically labeled spermine before and after PDITM.

Figure 11:
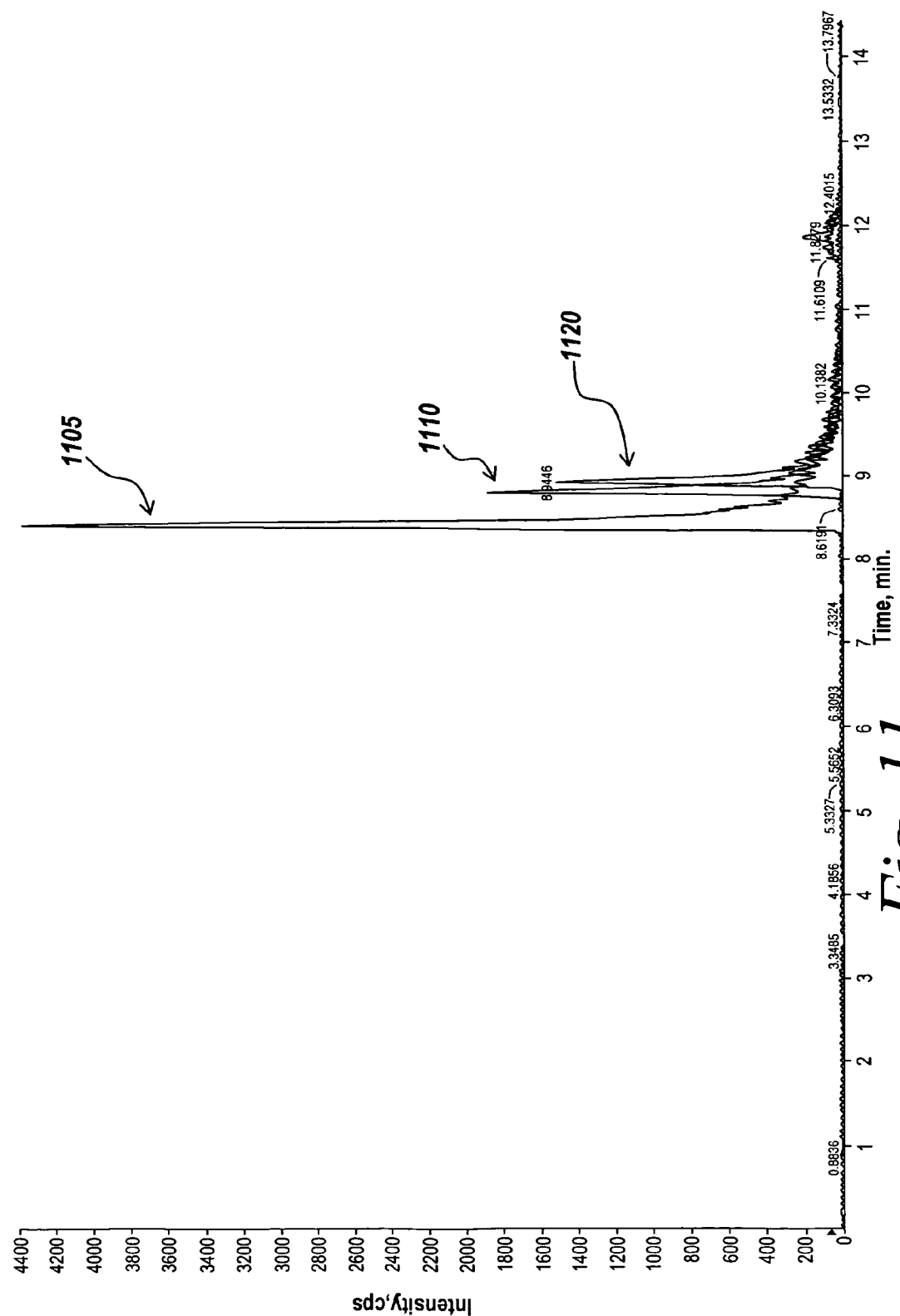

FIG. 11 schematically depicts the liquid chromatograph of a mixture of polyamines each labeled with a different isobaric tag from a set of isobaric tags.

FIG. 12A schematically depicts a chromatogram of putrescene labeled with an iTRAQ™ brand reagent. FIG. 12B schematically depicts a chromatogram of cadaverine labeled with an iTRAQ™ brand reagent. FIG. 12C schematically depicts a chromatogram of 1,7-diaminoheptane labeled with an iTRAQ™ brand reagent.

Figure 13:
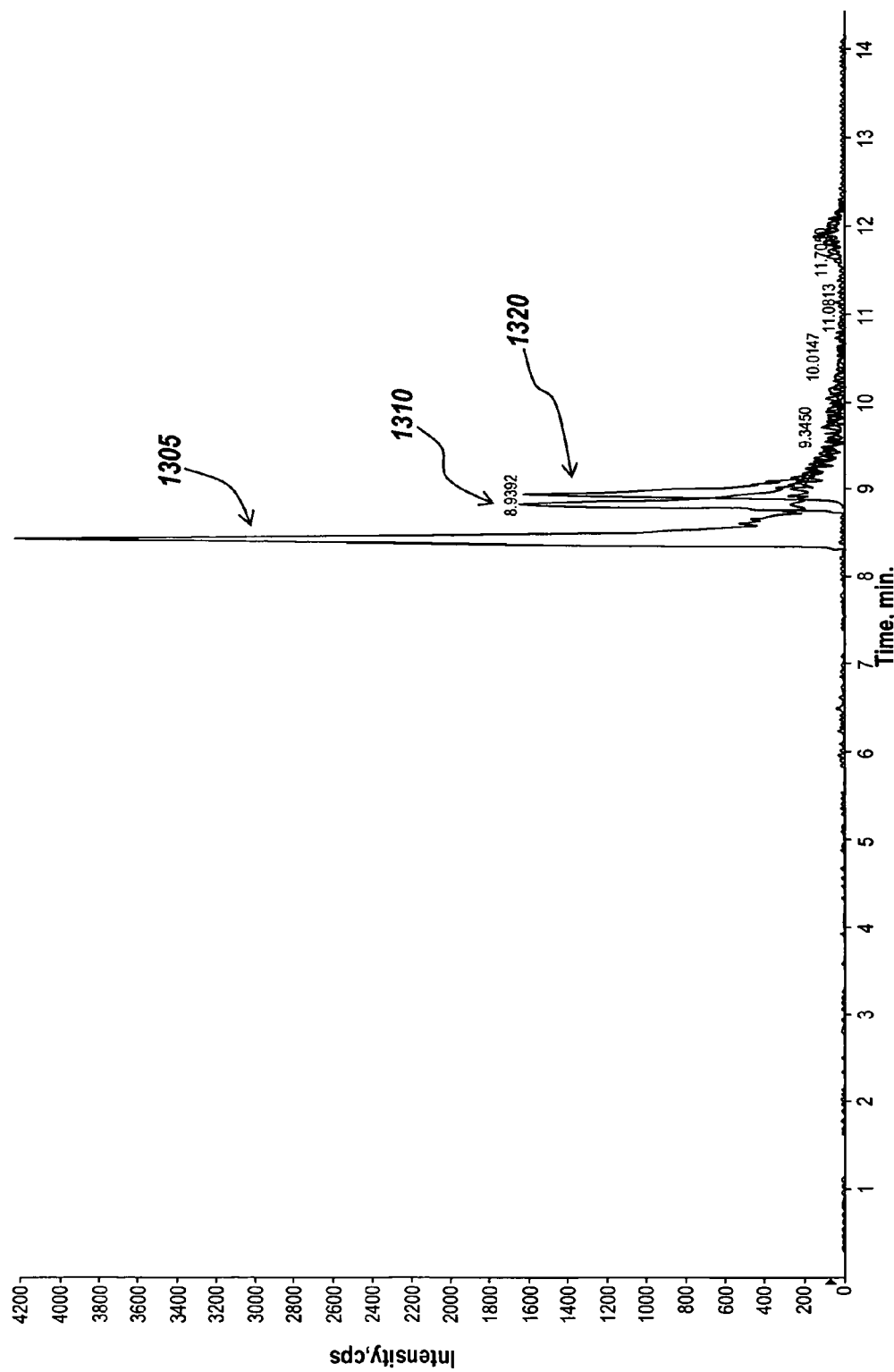

FIG. 13 schematically depicts a chromatogram of a mixture of polyamines each labeled with a different isobaric tag from a set of isobaric tags.

FIGS. 14A, 14B, 14C depict orthogonal-MALDI (O-MALDI) background mass spectra of a sample of a matrix comprising ACN and HCCA.

Figure 15:
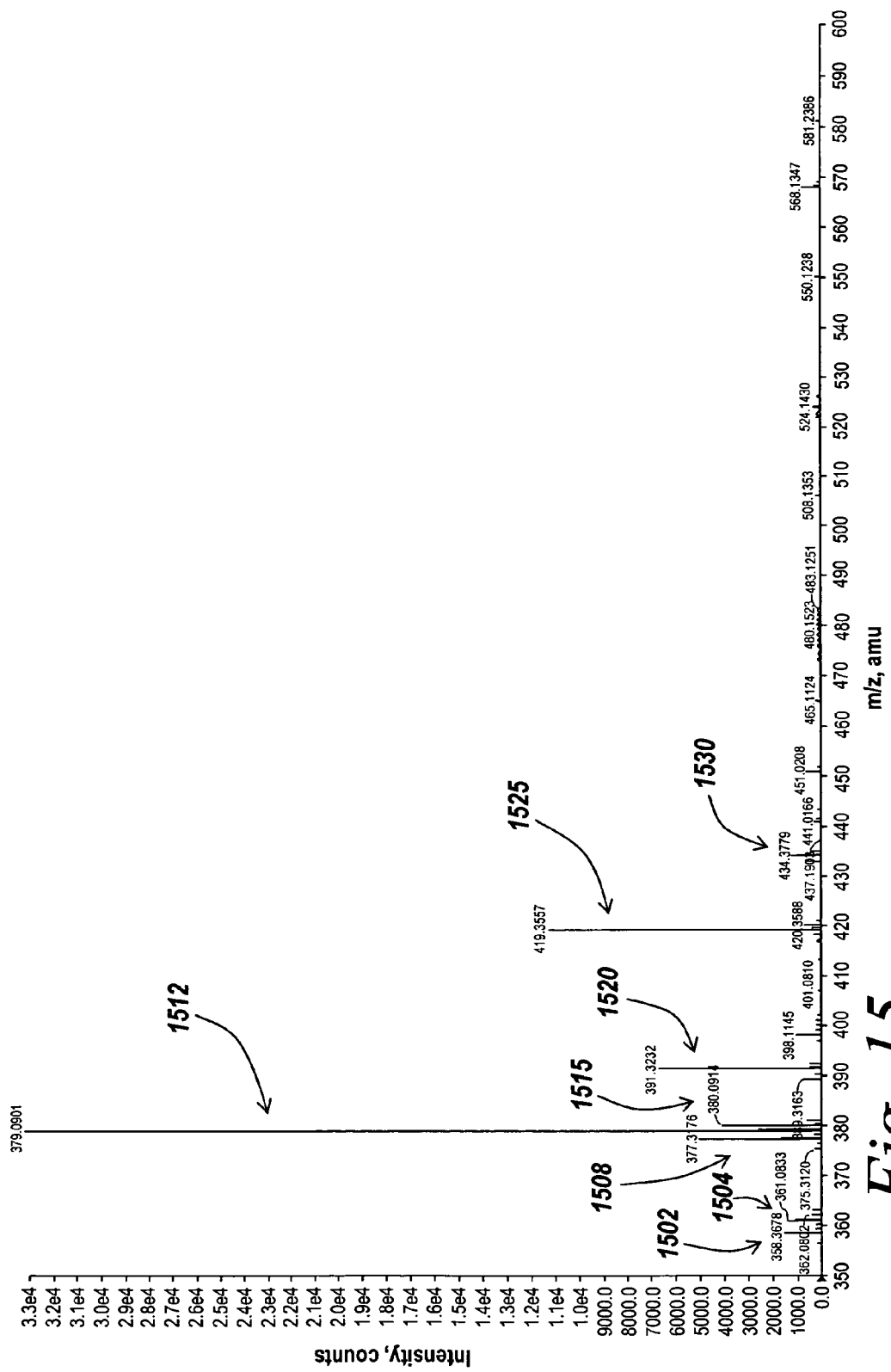

FIG. 15 depicts an O-MALDI mass spectrum of the four polyamines of Example 4 in a matrix of ACN and HCCA.

Figure 16A:
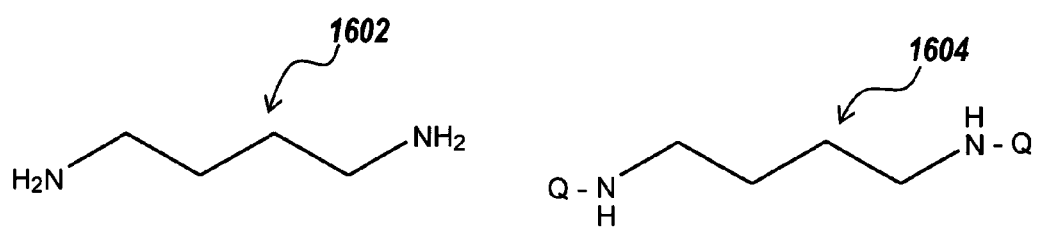
Figure 16B:
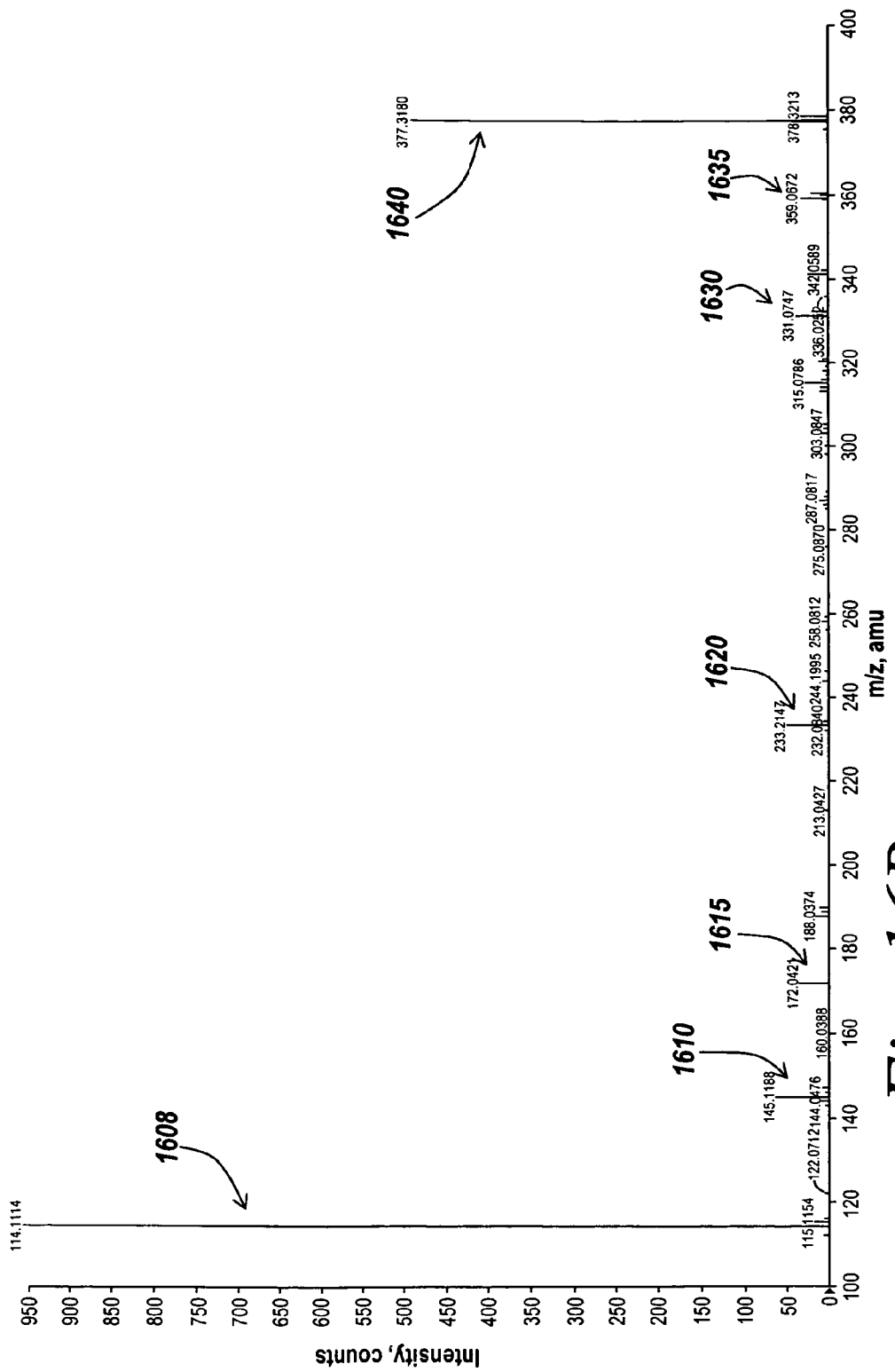

FIG. 16A schematically depicts the structure of unlabeled putrescene and putrescene labeled with an iTRAQ™ brand reagent, and FIG. 16B depicts an O-MALDI mass spectrum of isobarically labeled putrescene after PDITM.

Figure 17A:
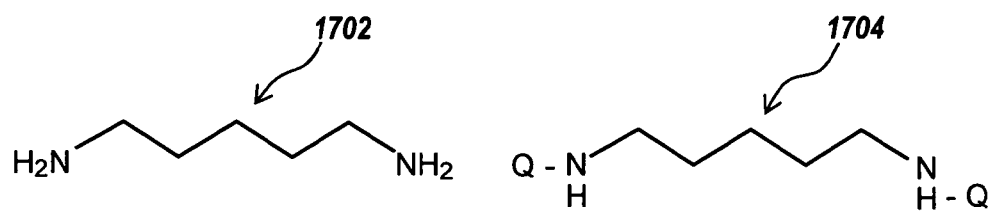
Figure 17B:
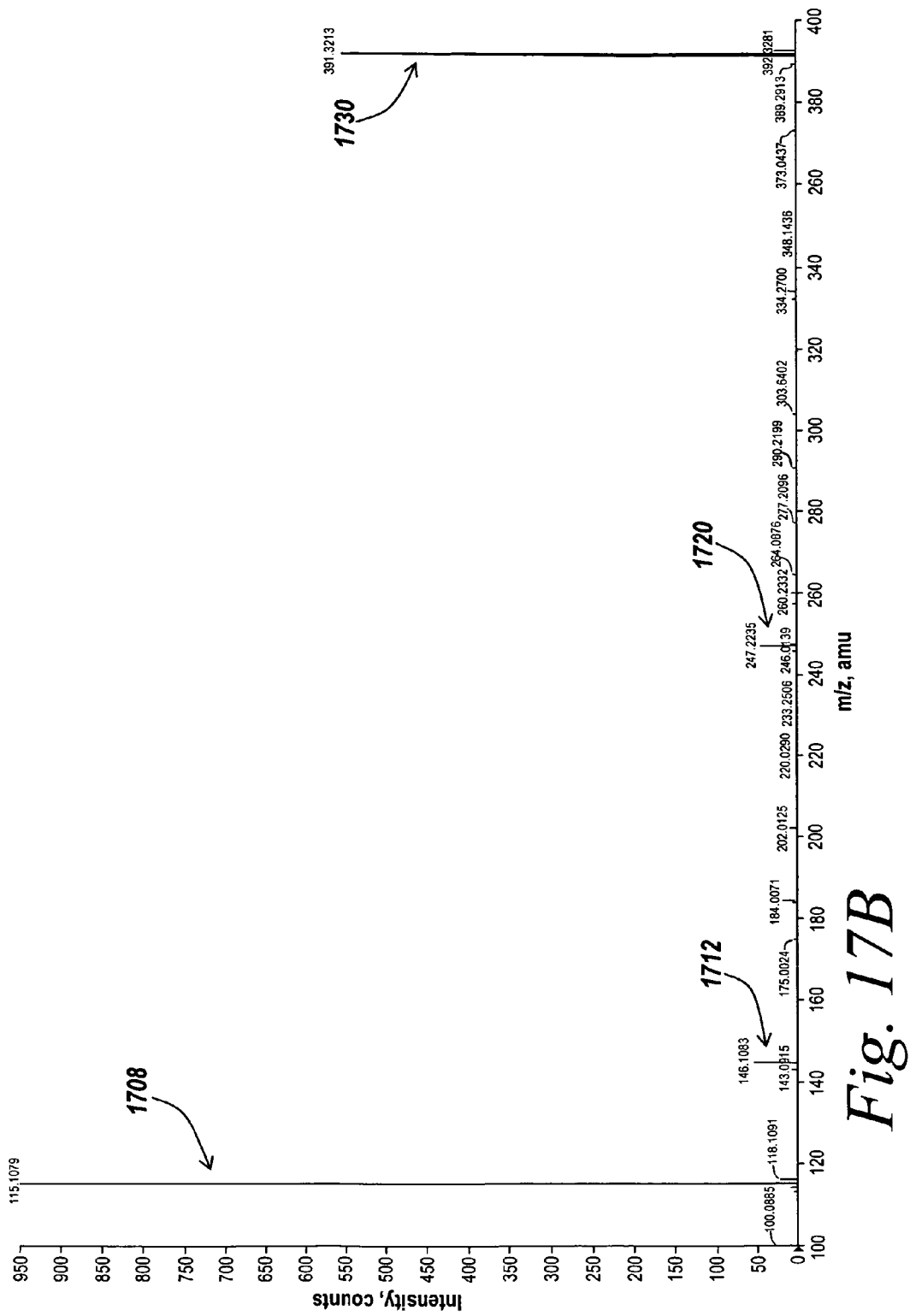

FIG. 17A schematically depicts the structure of unlabeled cadaverine and cadaverine labeled with an iTRAQ™ brand reagent, and FIG. 17B depicts an O-MALDI mass spectrum of isobarically labeled cadaverine after PDITM.

Figure 18A:
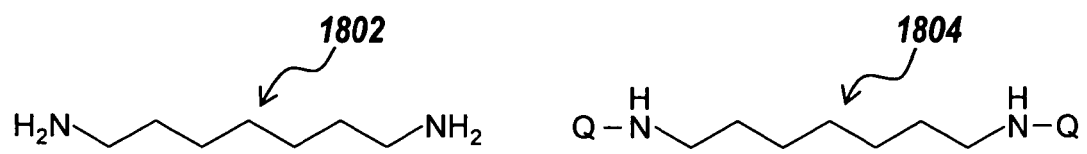

FIG. 18A schematically depicts the structure of unlabeled 1,7-diaminoheptane and 1,7-diaminoheptane labeled with an iTRAQ™ brand reagent, and FIG. 18B depicts an O-MALDI mass spectrum of isobarically labeled 1,7-diaminoheptane after PDITM.

Figure 19A:
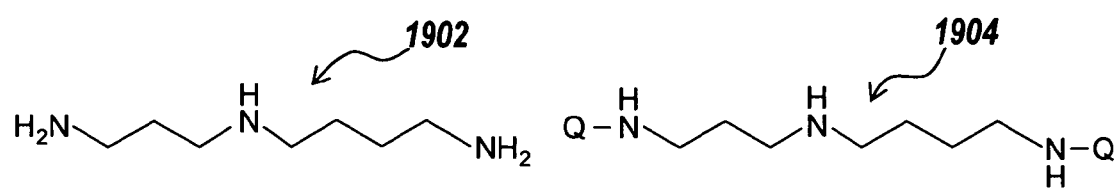
Figure 19B:
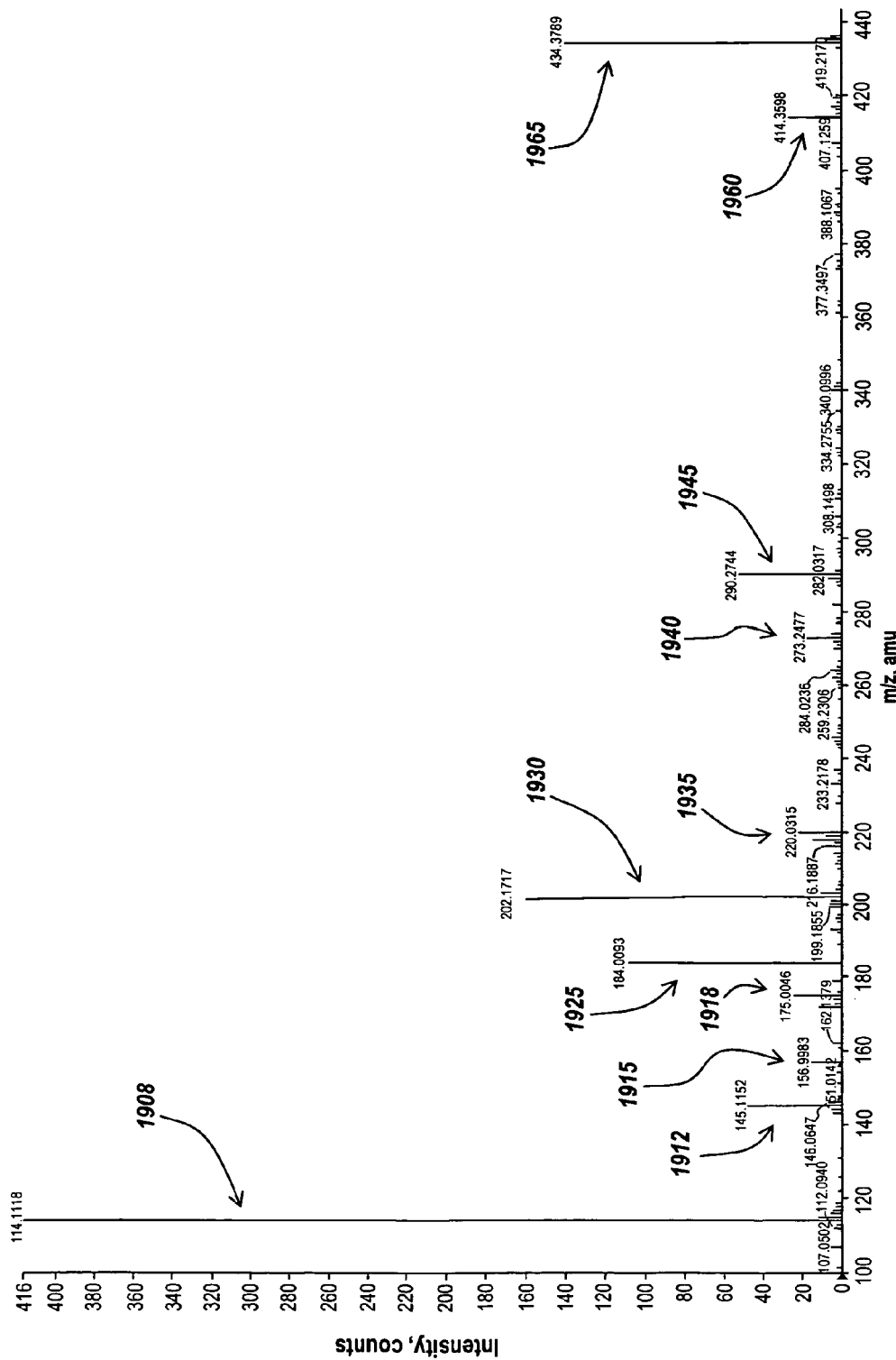

FIG. 19A schematically depicts the structure of unlabeled spermidine and spermidine labeled with an iTRAQ™ brand reagent, and FIG. 19B depicts an O-MALDI mass spectrum of isobarically labeled spemidine after PDITM.

Figure 20A:
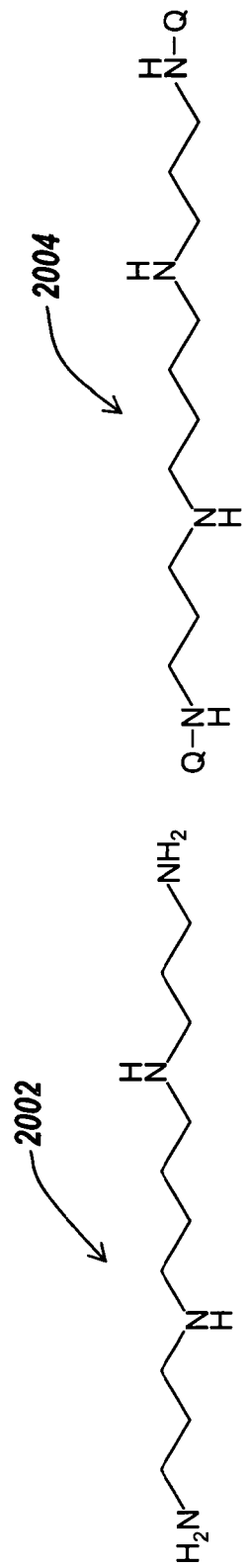
Figure 20B:
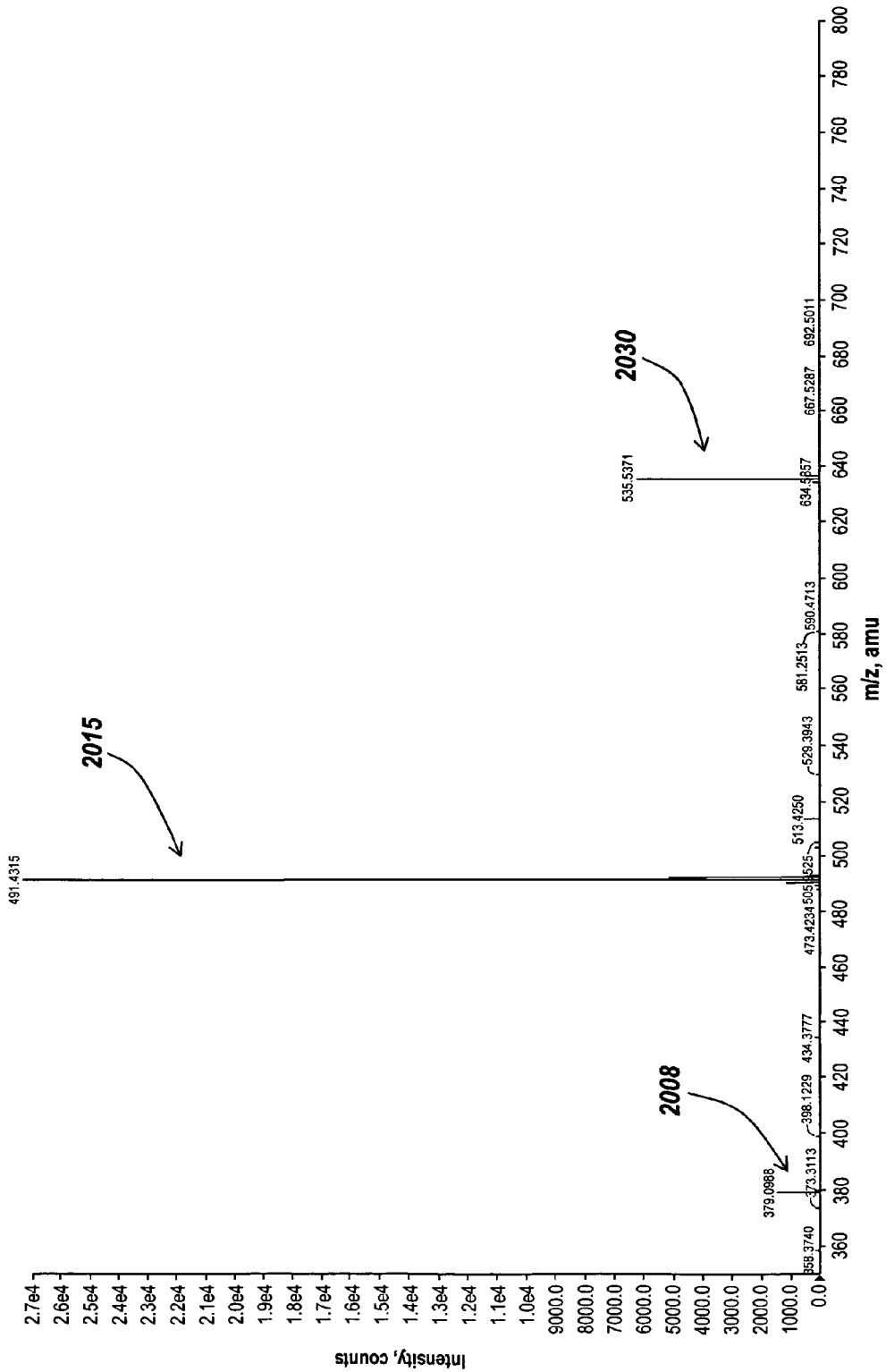

FIG. 20A schematically depicts the structure of unlabeled spermine and spermine labeled with an iTRAQ™ brand reagent, and FIG. 20B depicts an O-MALDI mass spectrum of isobarically labeled spemidine after PDITM.

Figure 21A:
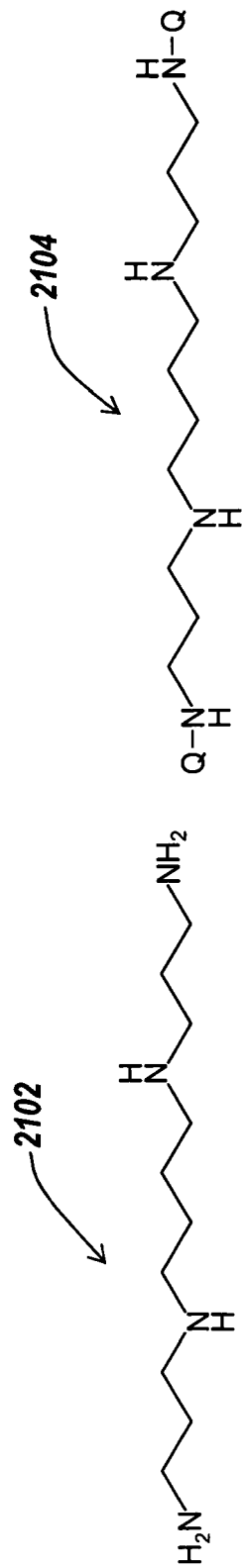
Figure 21B:
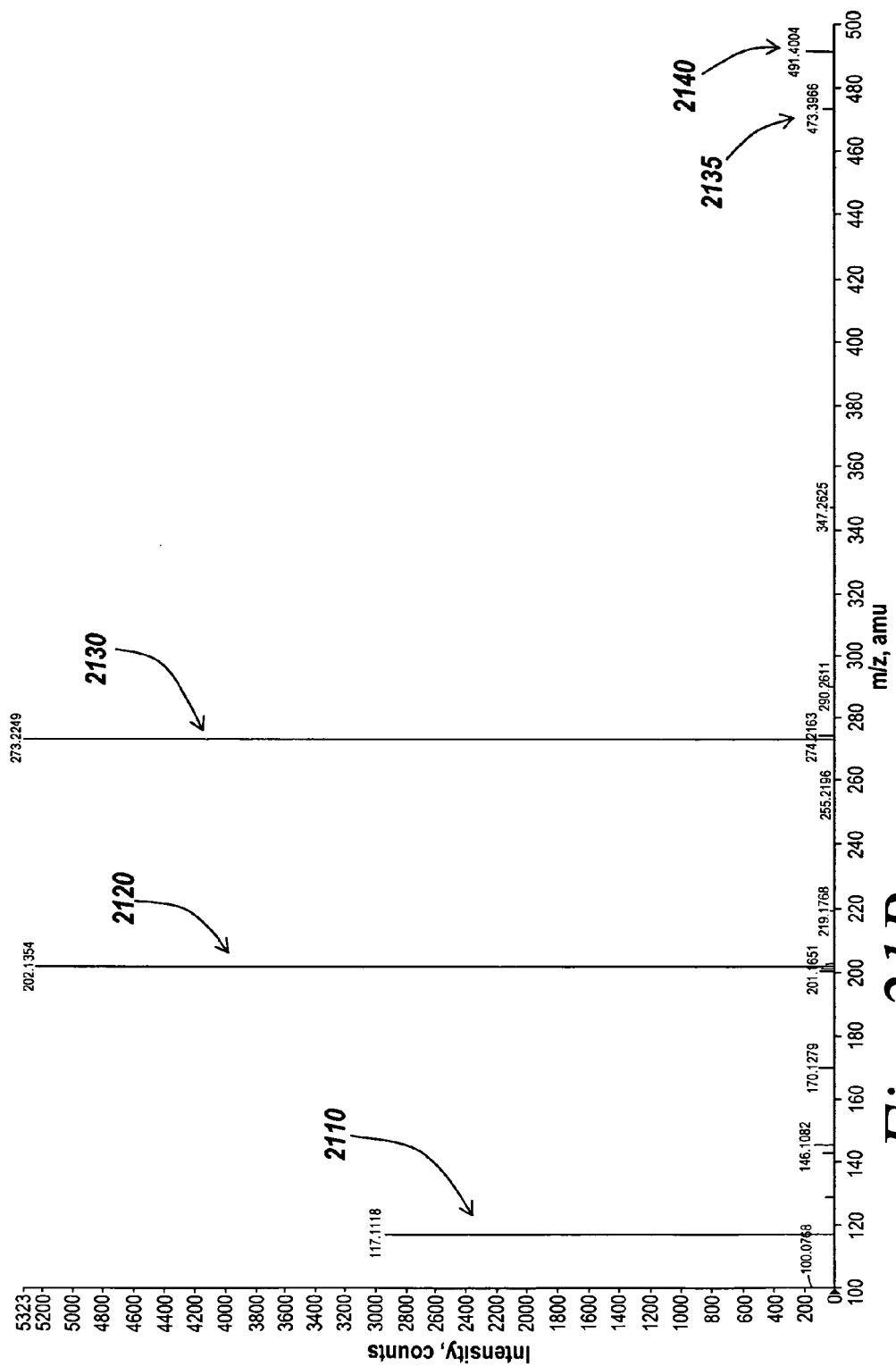
Figure 21C:
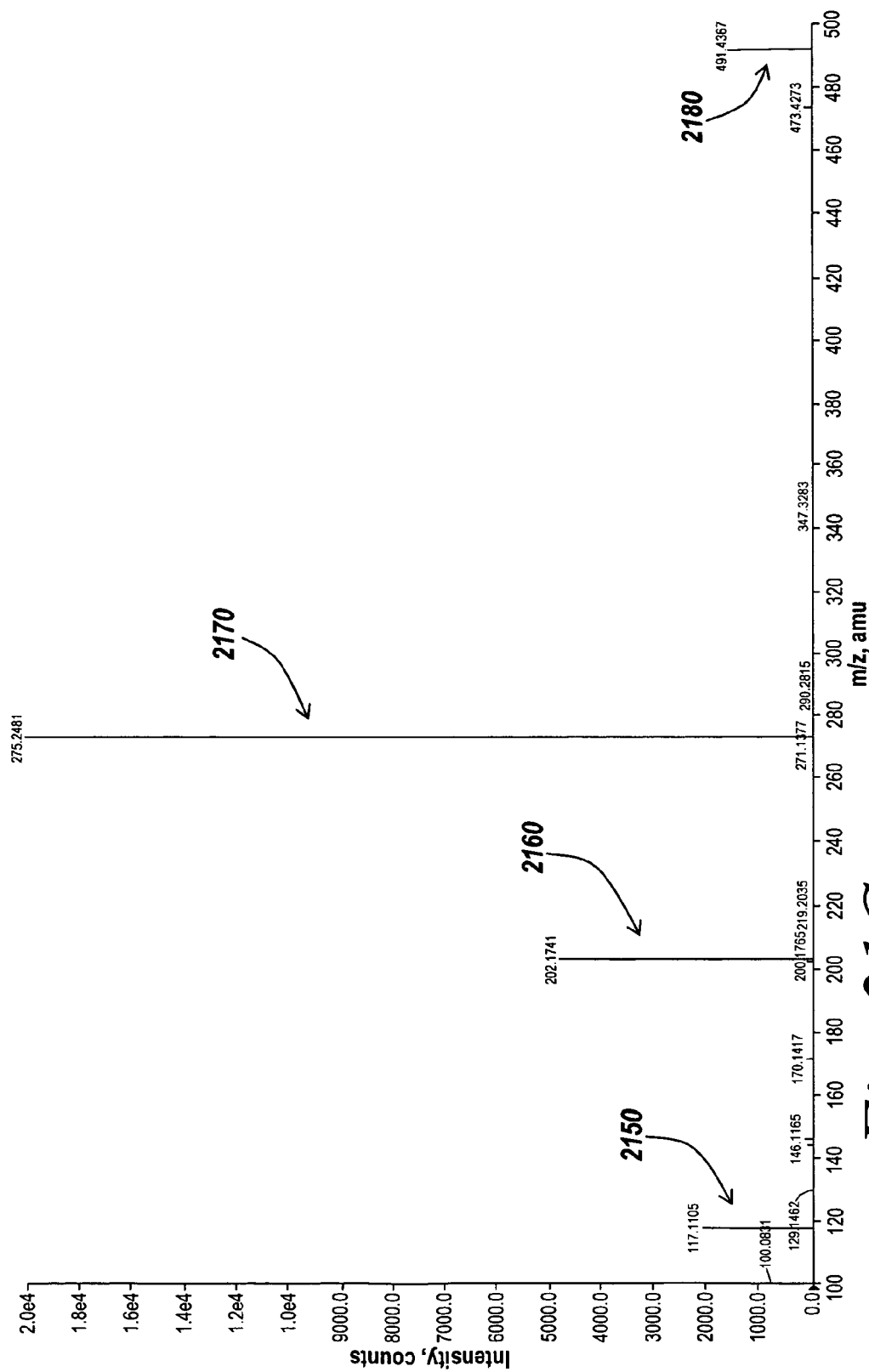

FIG. 21A schematically depicts the structure of unlabeled spermine and spermine labeled with an iTRAQ™ brand reagent, and FIGS. 21B and 21C depict O-MALDI mass spectra after PDITM.

Figure 22A:
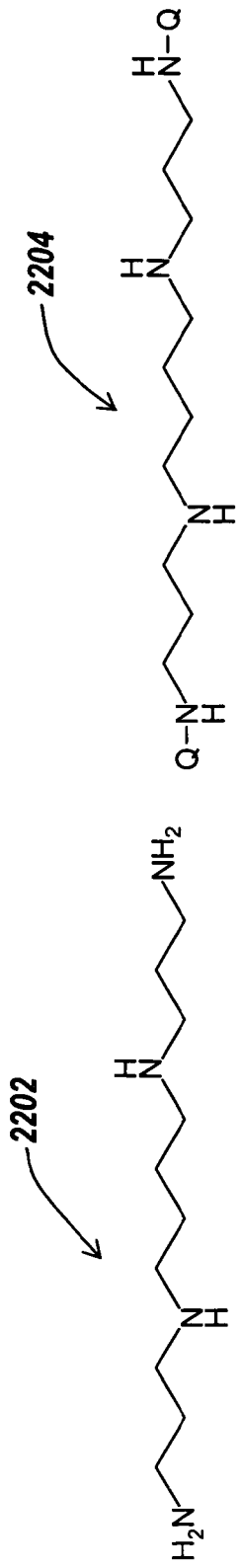
Figure 22B:
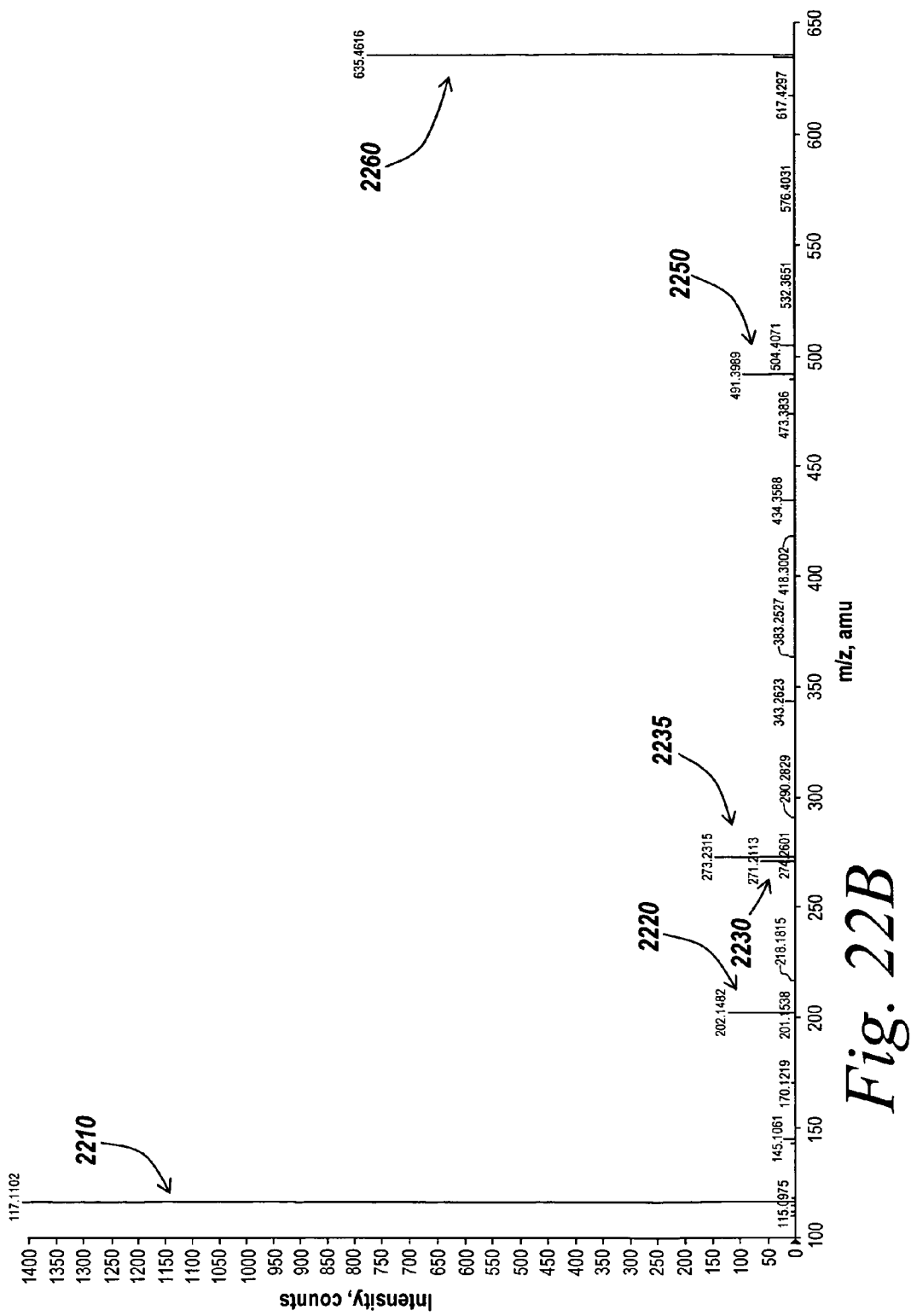

FIG. 22A schematically depicts the structure of unlabeled spermine and spermine labeled with an iTRAQ™ brand reagent, and FIG. 22B depicts an O-MALDI mass spectrum of isobarically labeled spemidine after PDITM.

Figure 23:
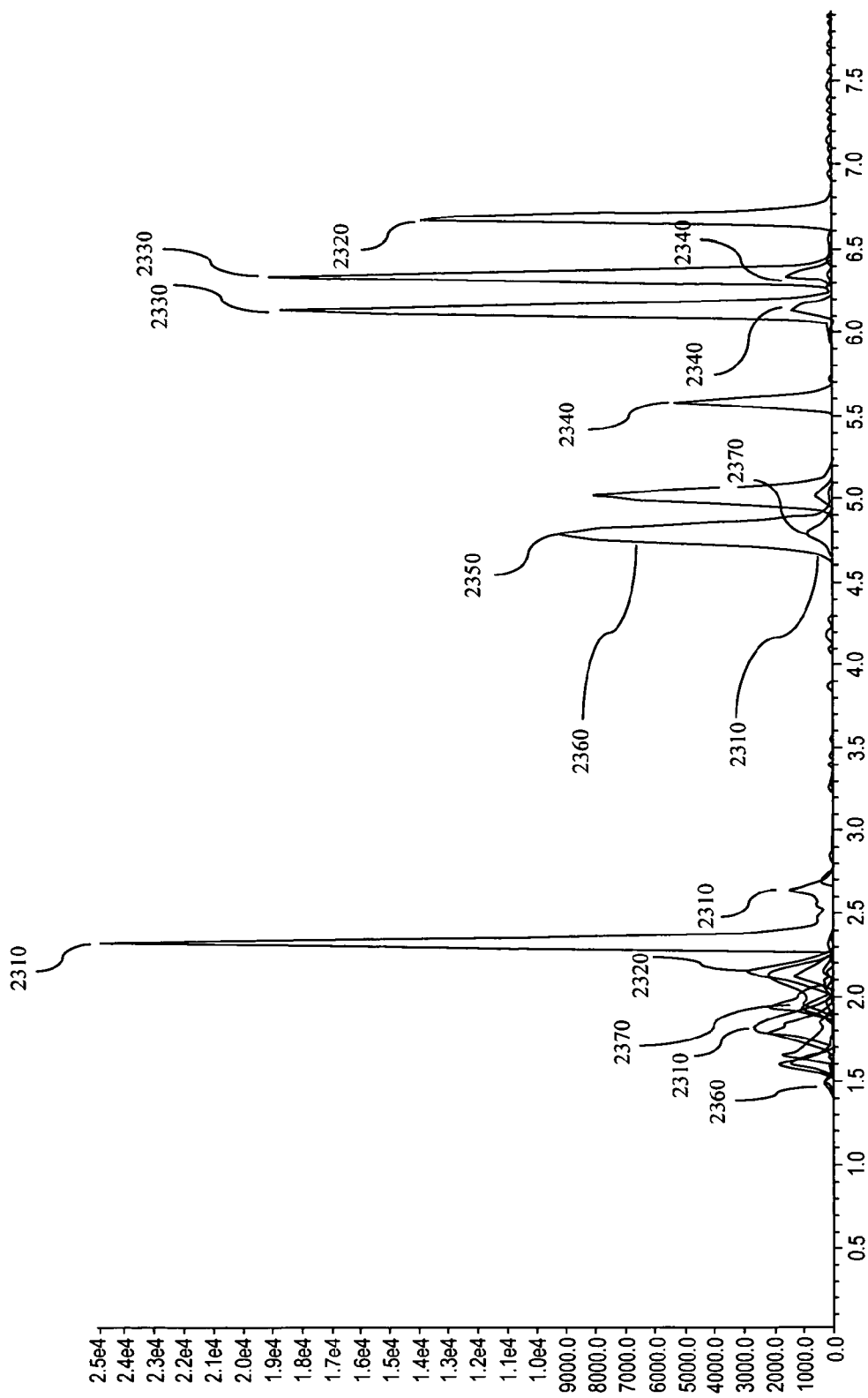

FIG. 23 schematically depicts a chromatogram of a mixture of labeled amino acids.

Figure 24:
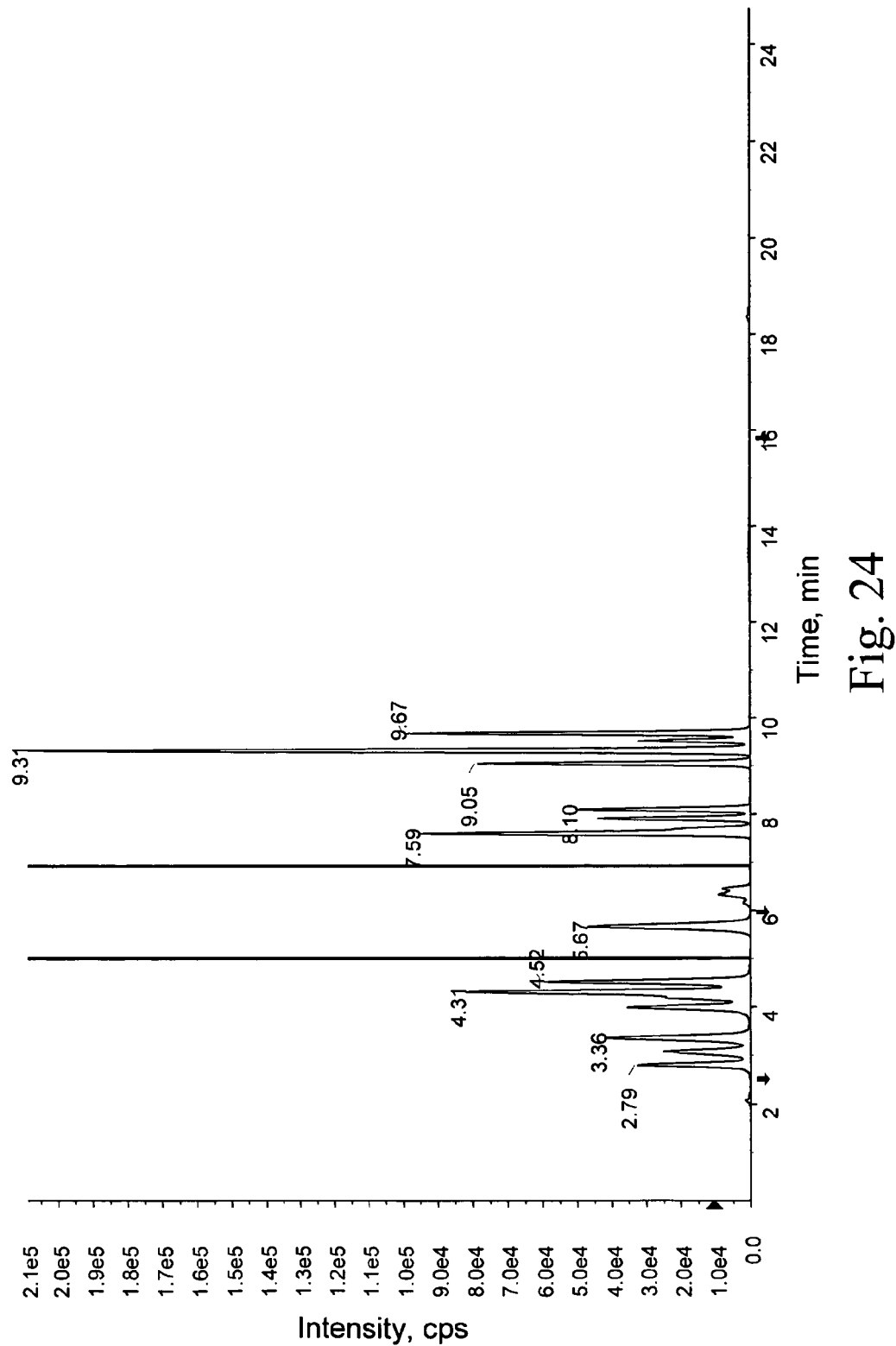

FIG. 24 schematically depicts a total ion current (TIC) chromatogram of a sample of a mixture of labeled amino acids of Example 5.

Figure 25A:
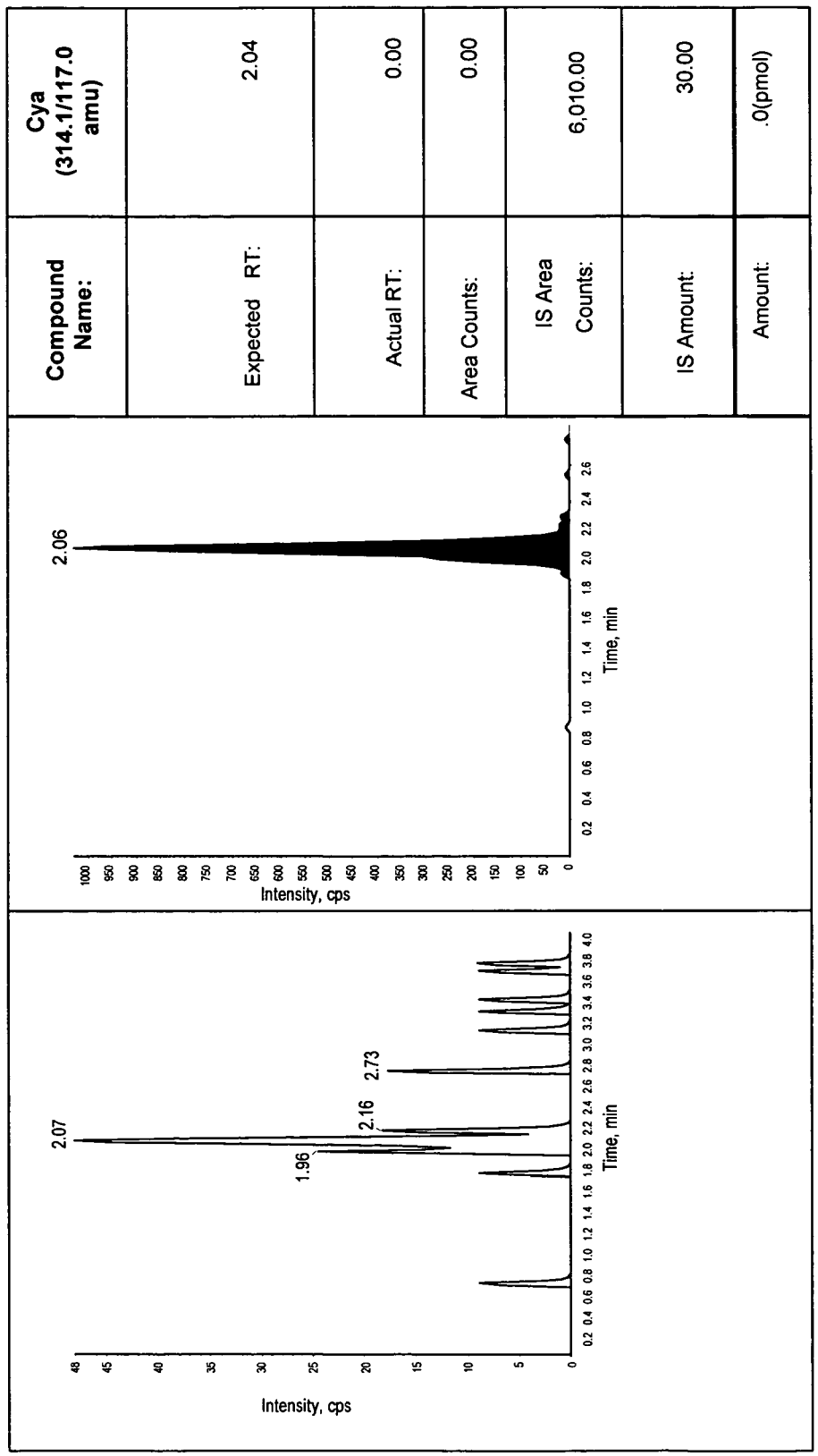
Figure 25B:
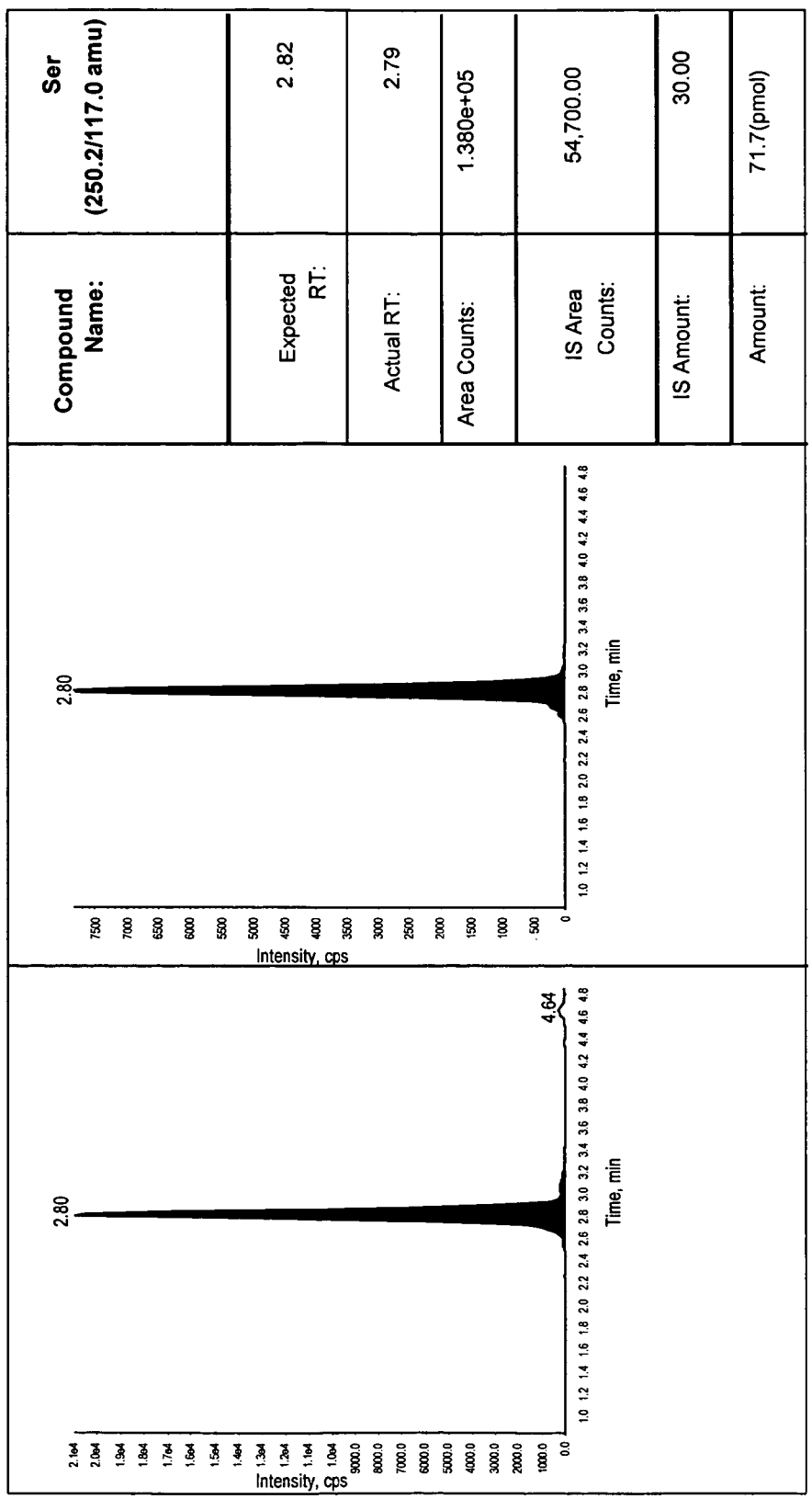
Figure 25C:
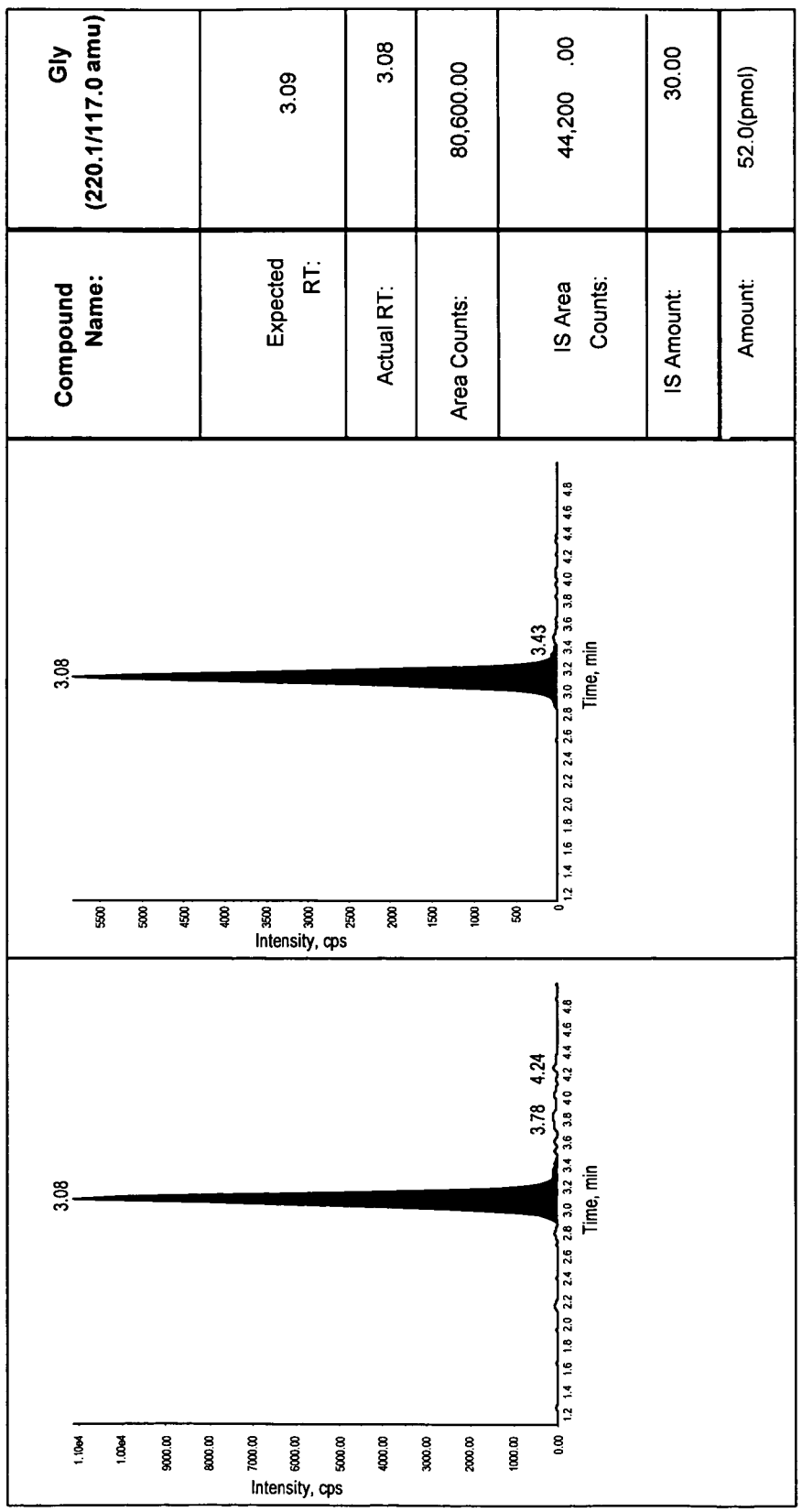
Figure 25D:
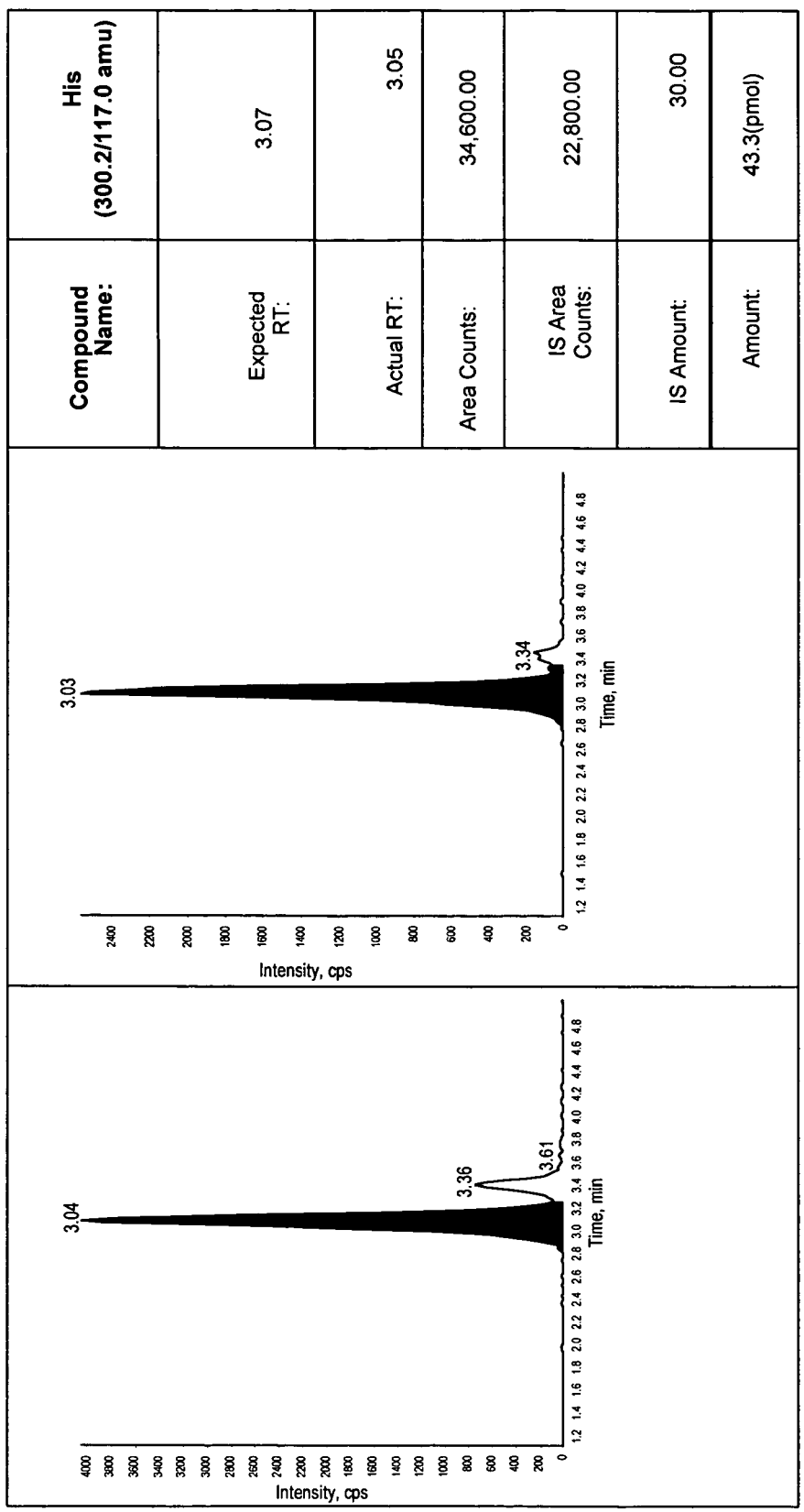
Figure 25E:
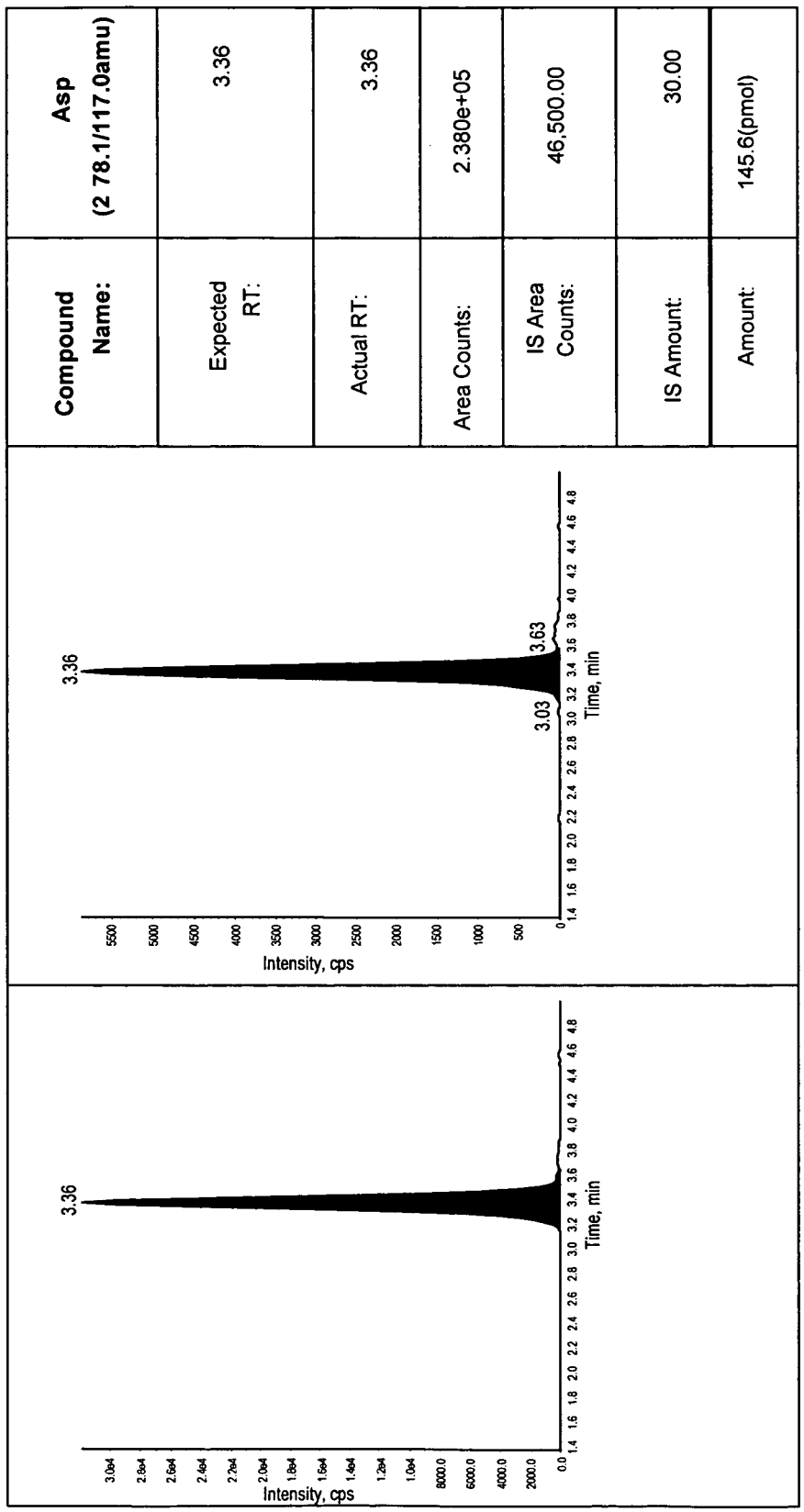
Figure 25F:
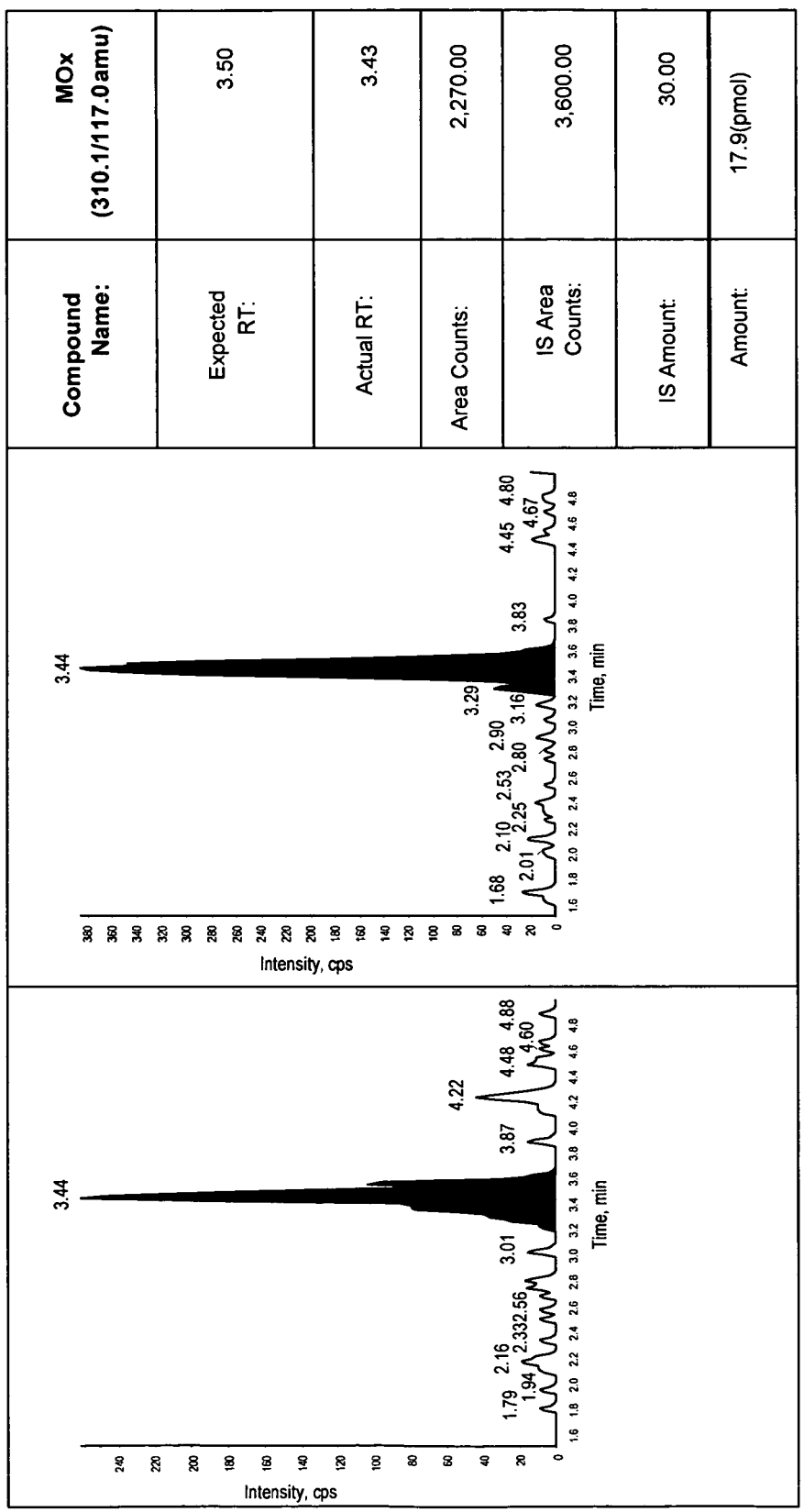
Figure 25G:
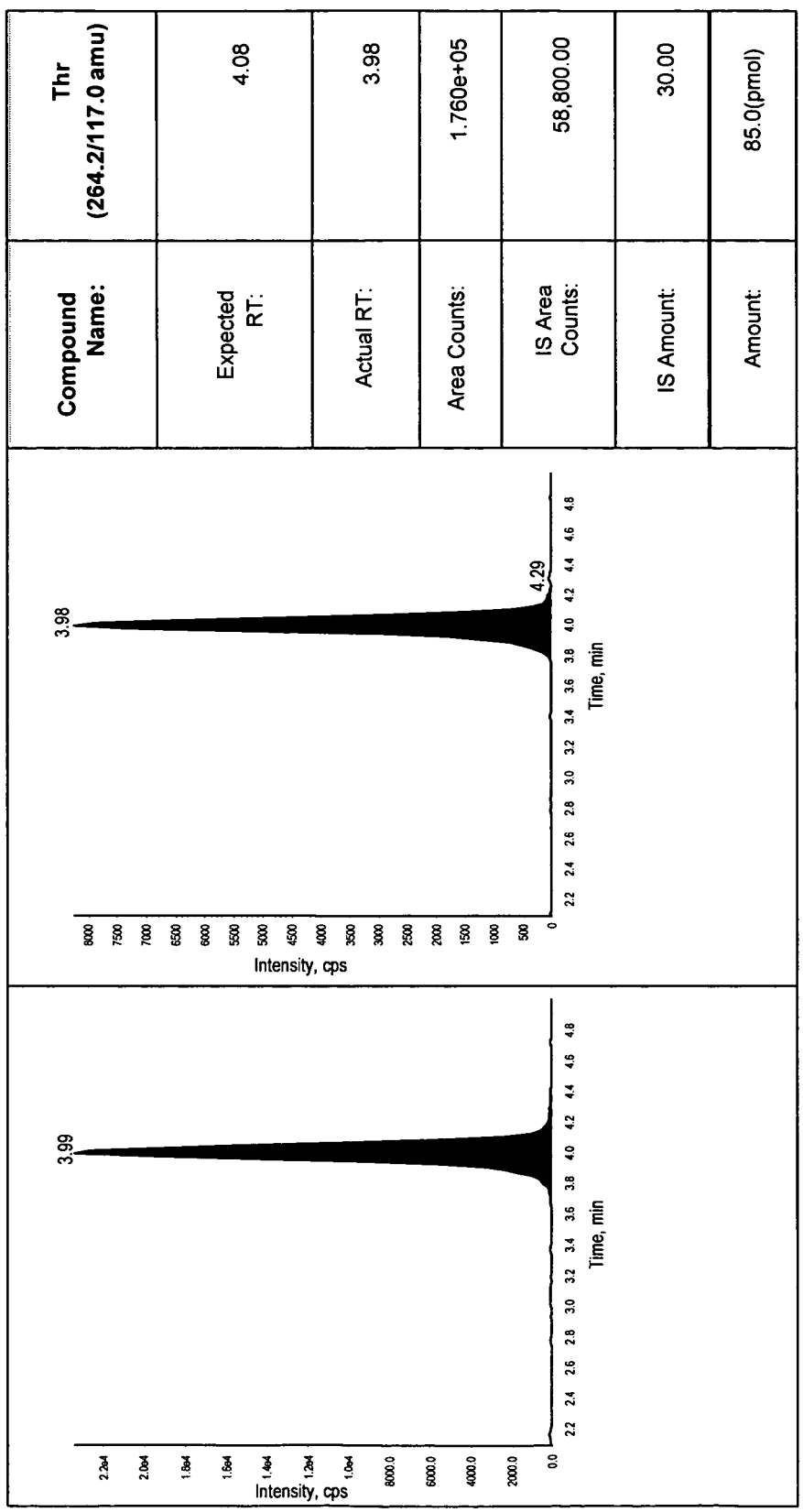
Figure 25H:
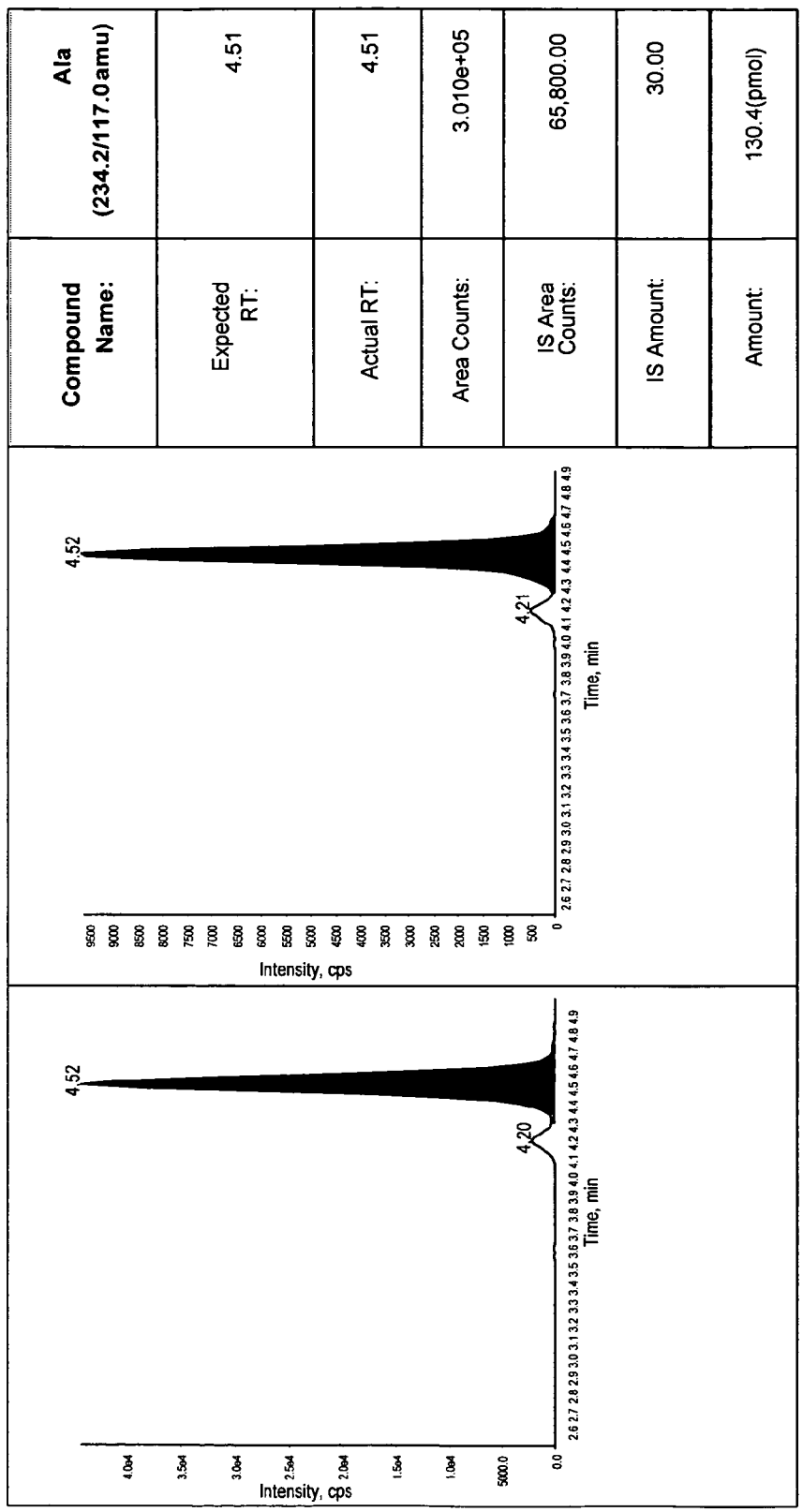
Figure 25I:
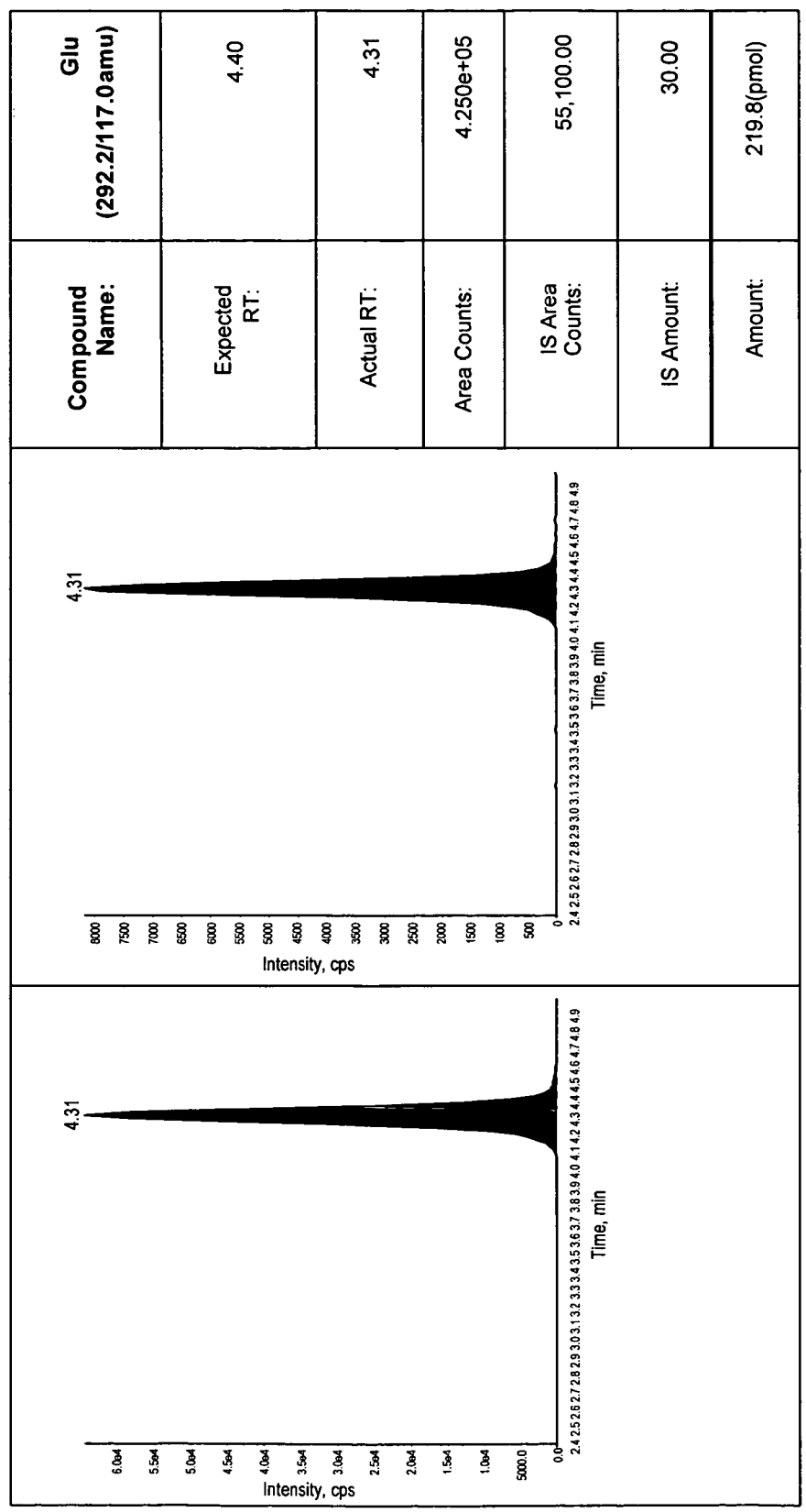
Figure 25J:
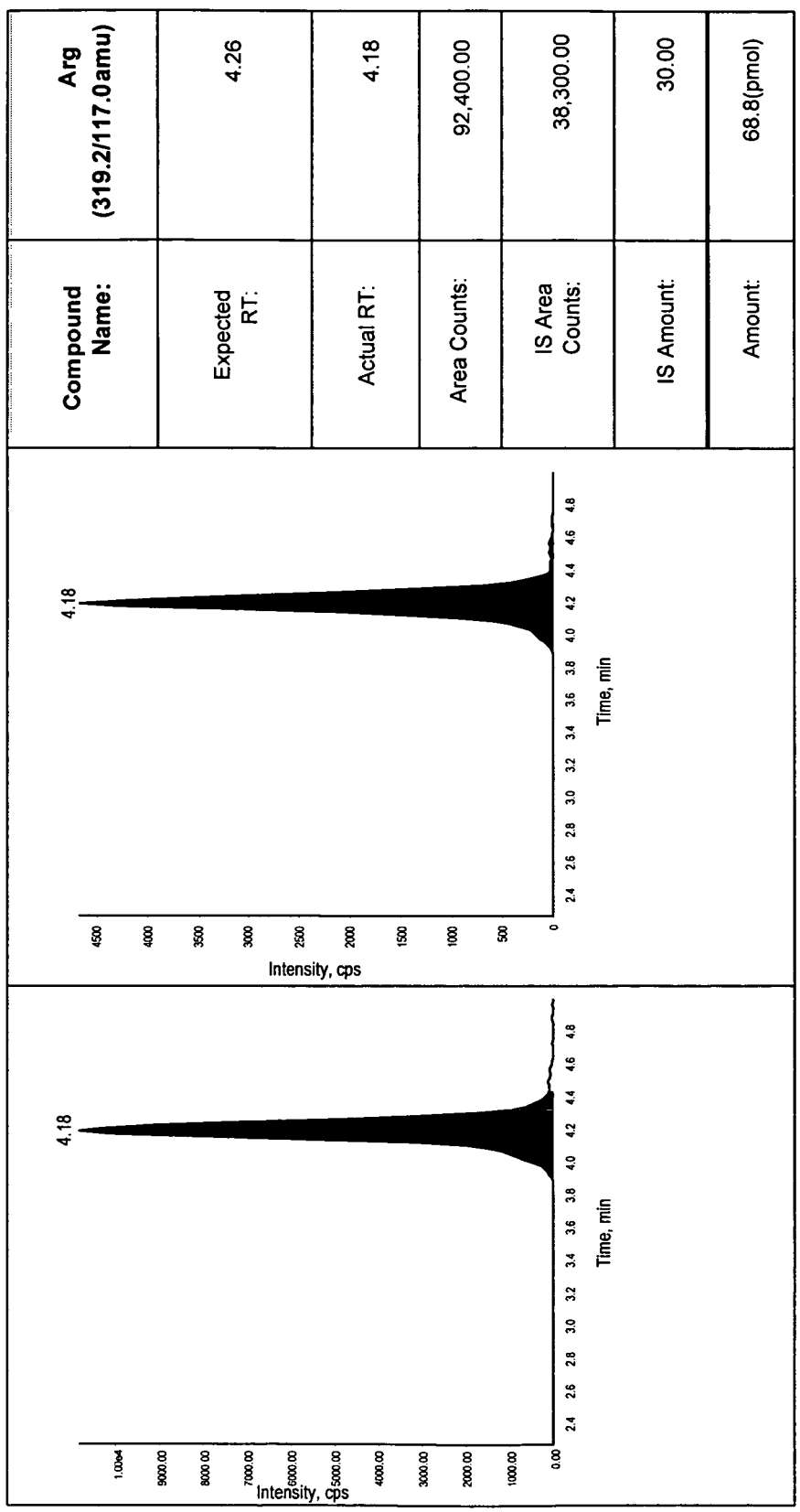
Figure 25K:
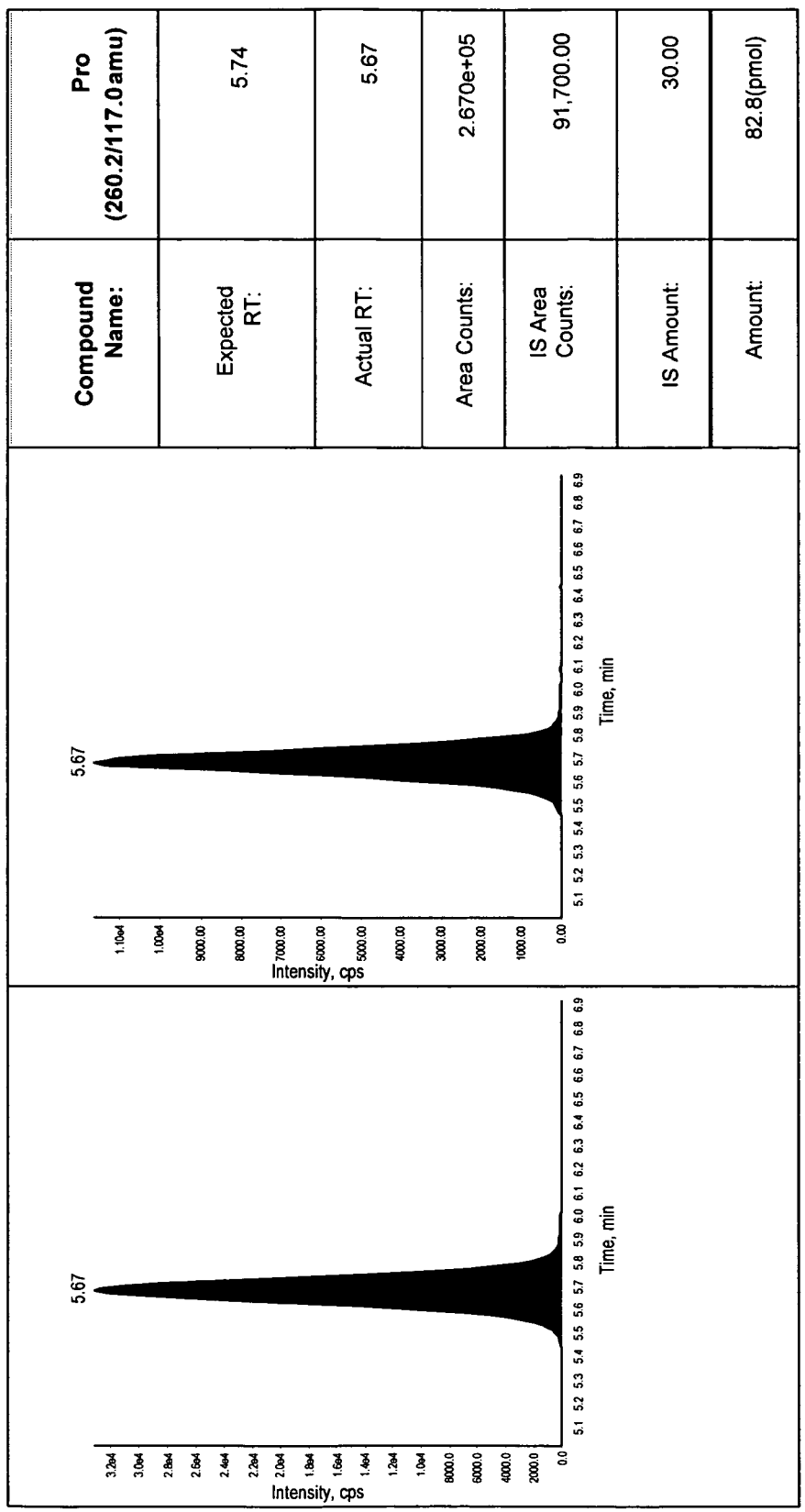
Figure 25L:
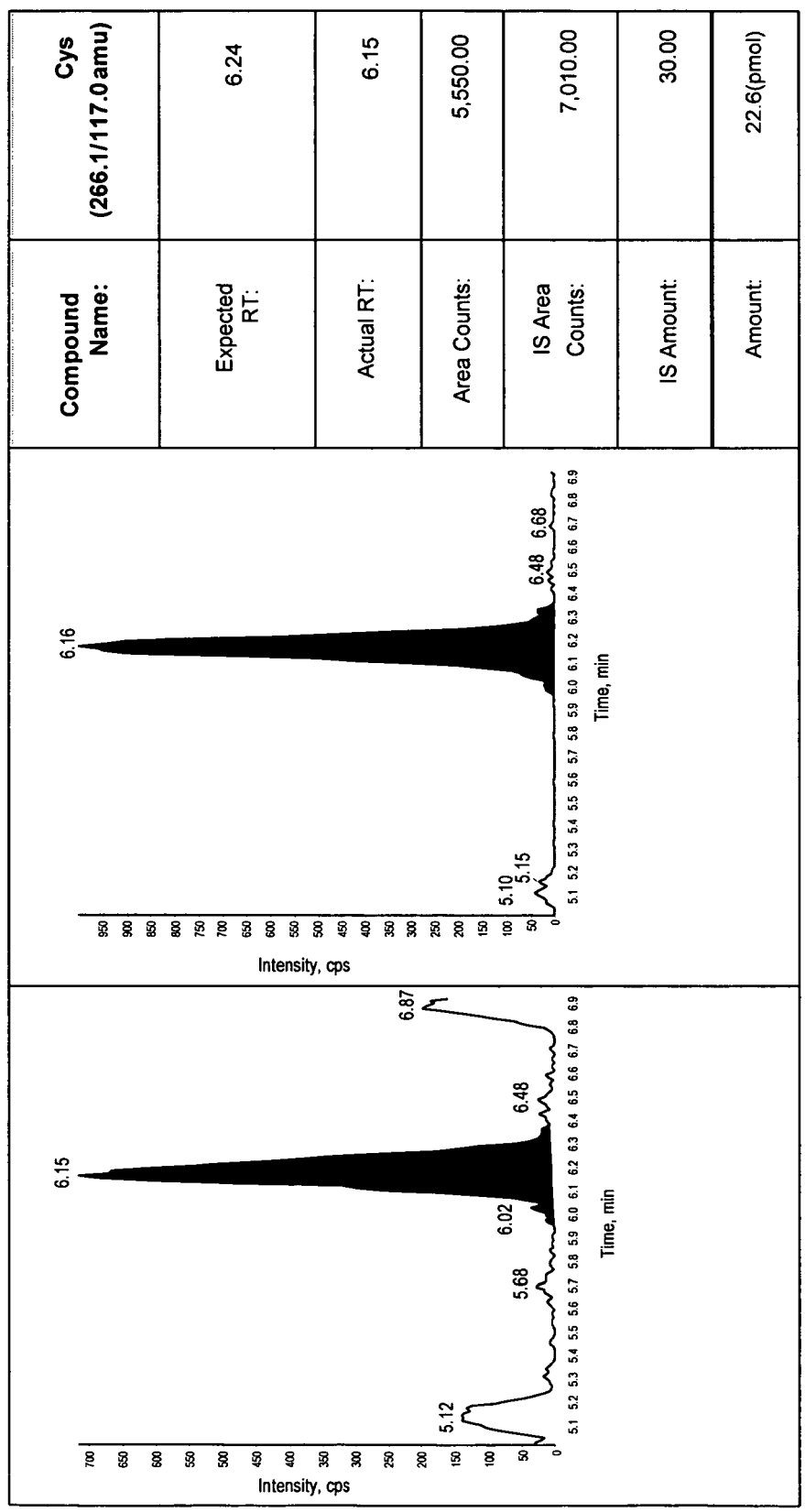
Figure 25M:
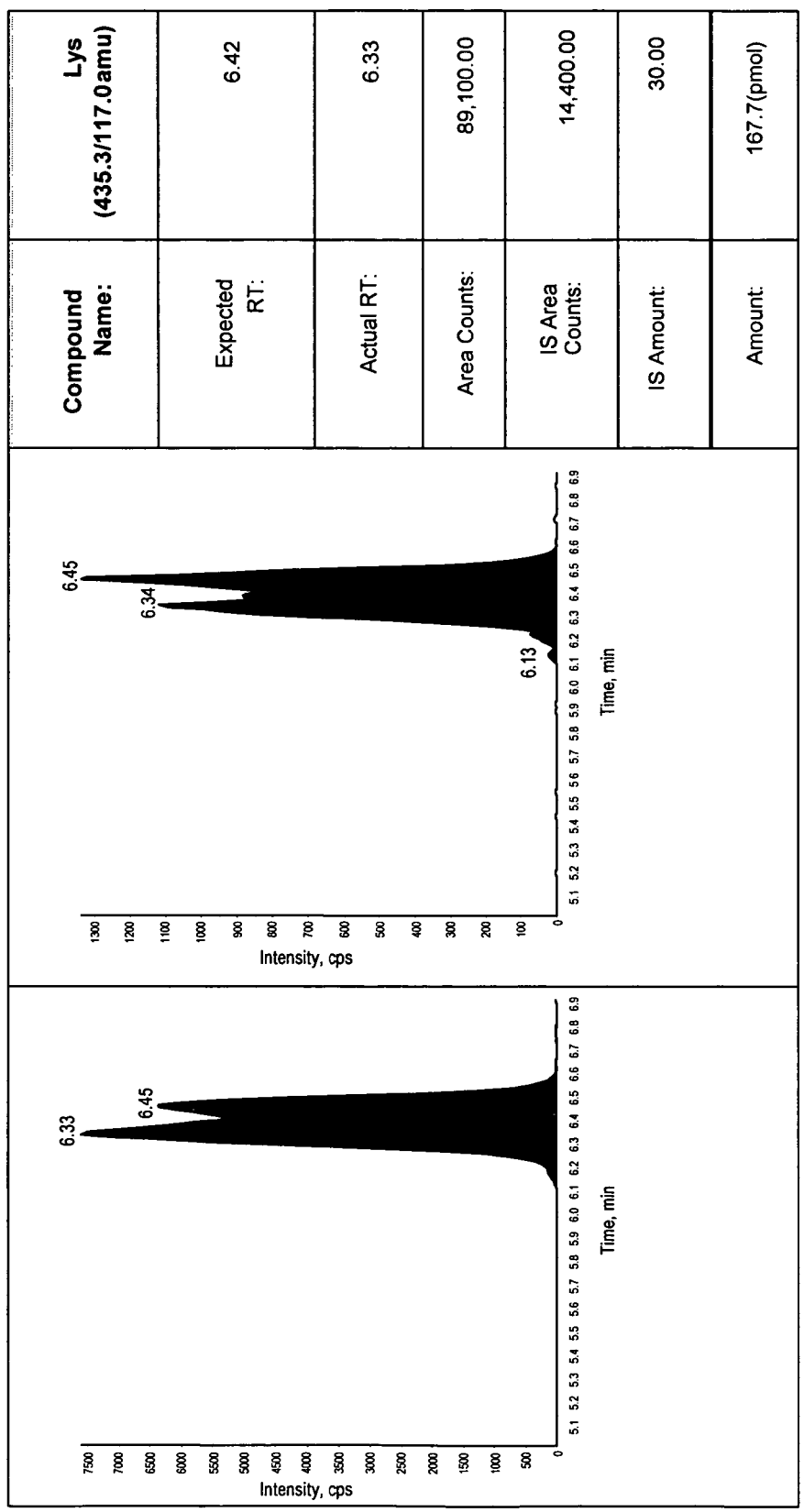
Figure 25N:
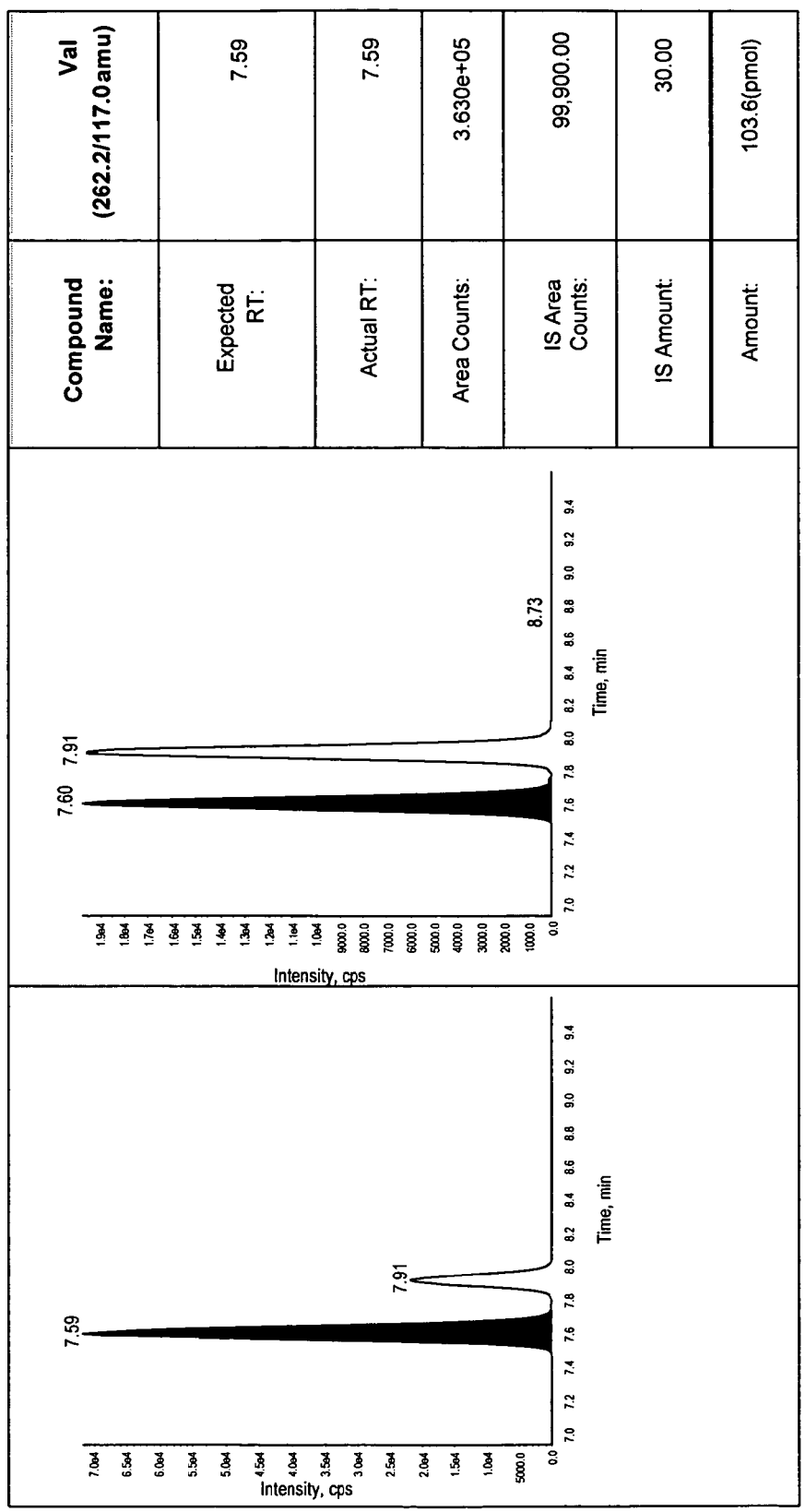
Figure 25O:
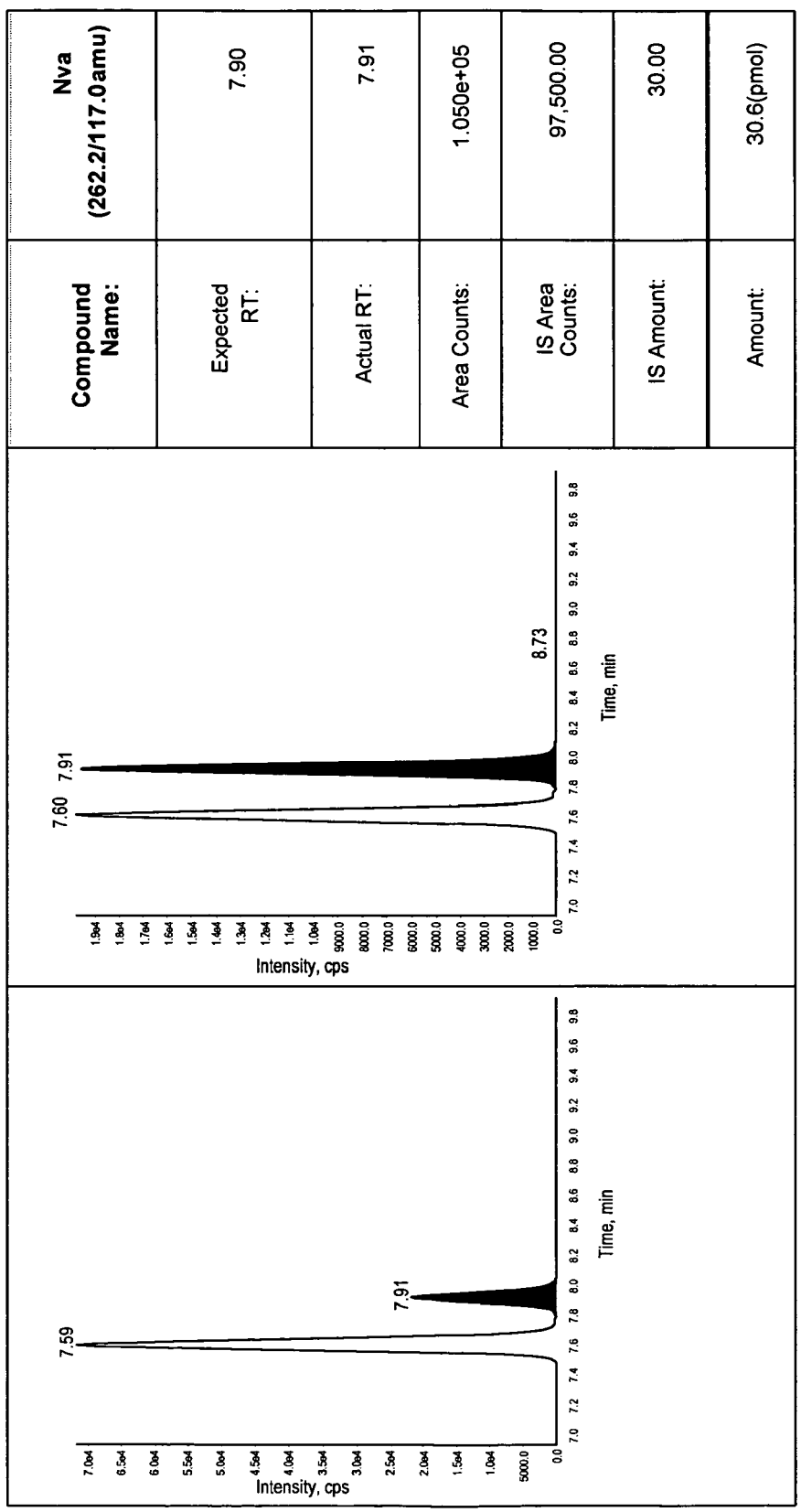
Figure 25P:
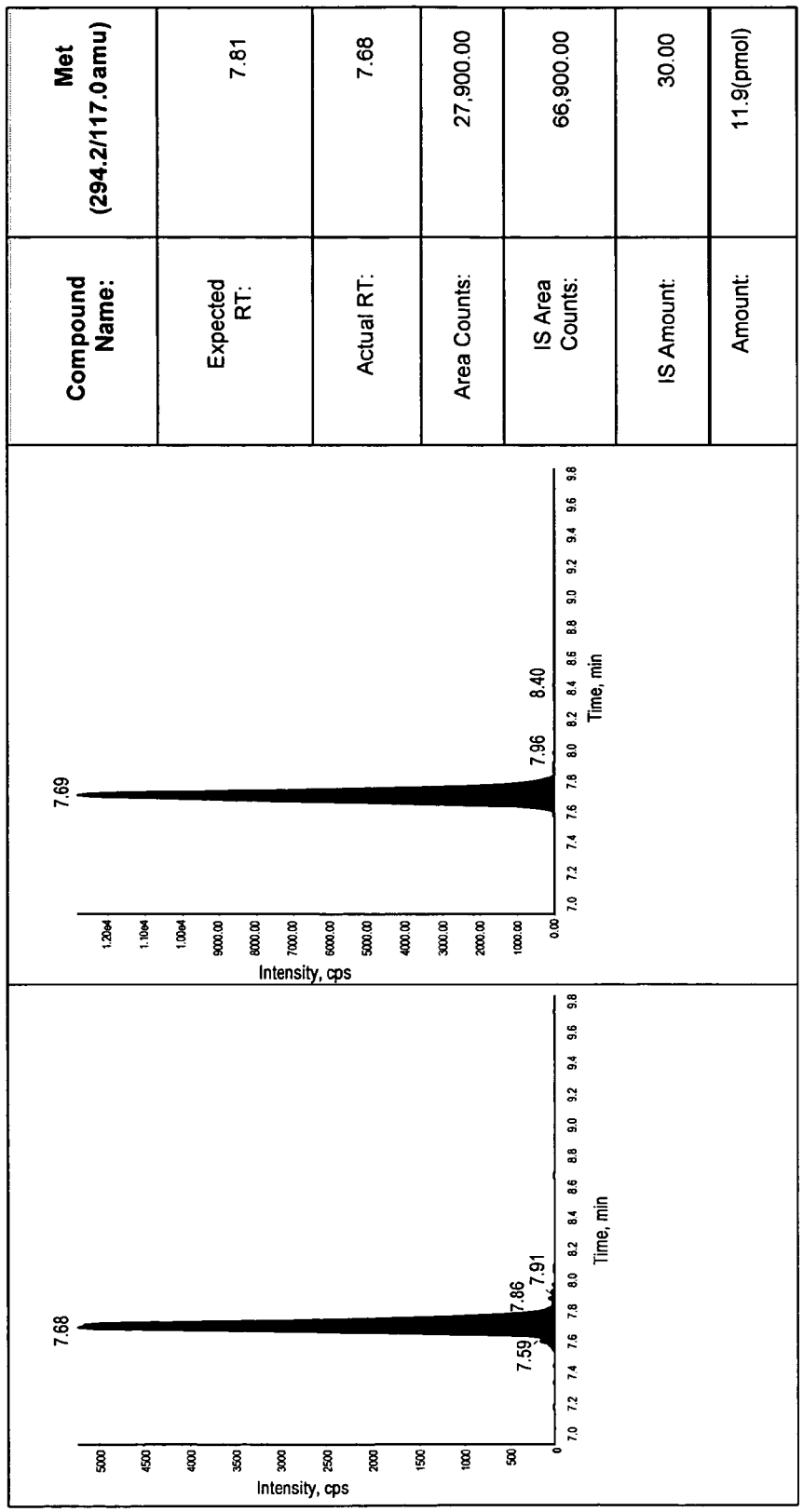
Figure 25Q:
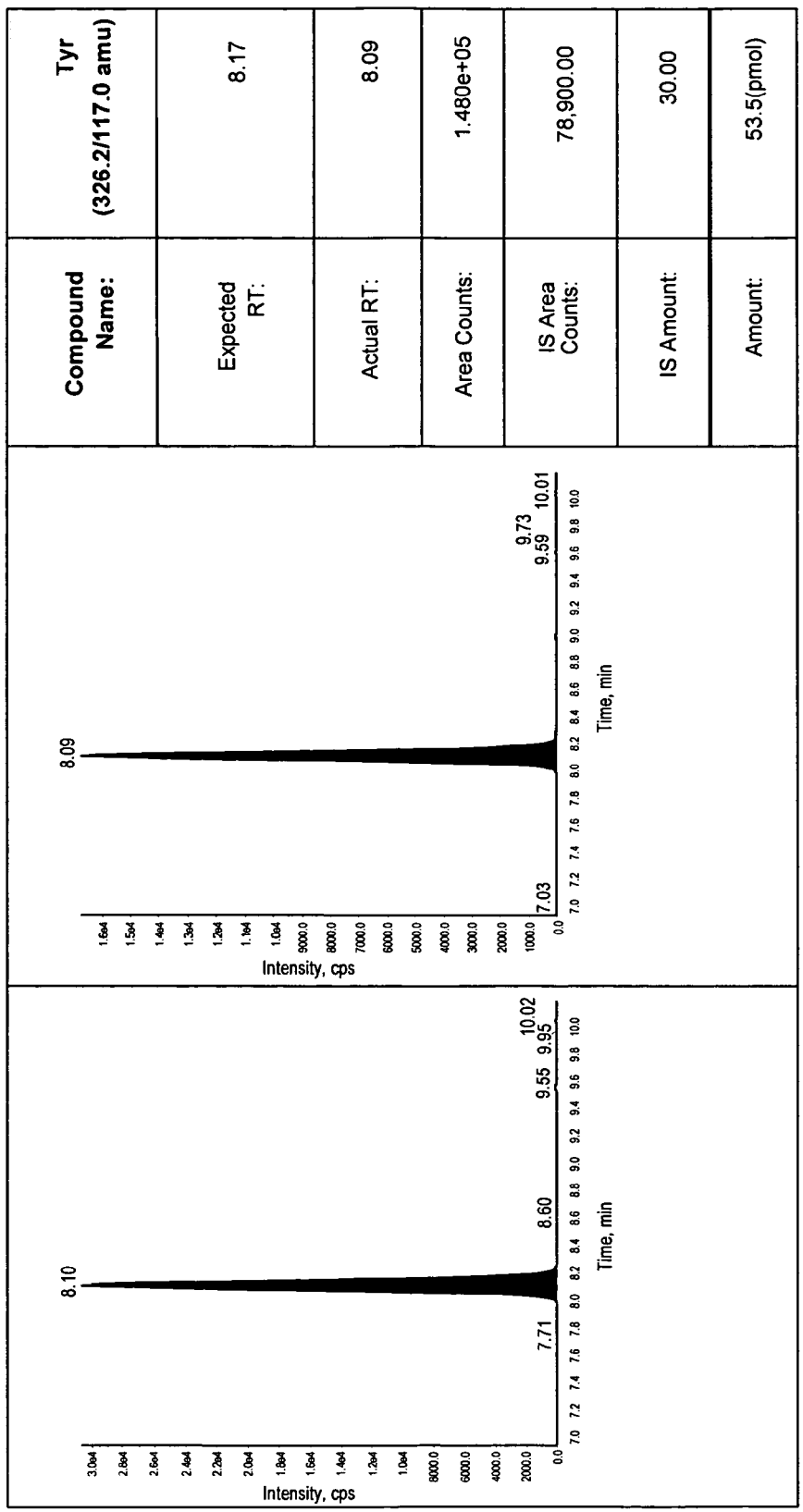
Figure 25R:
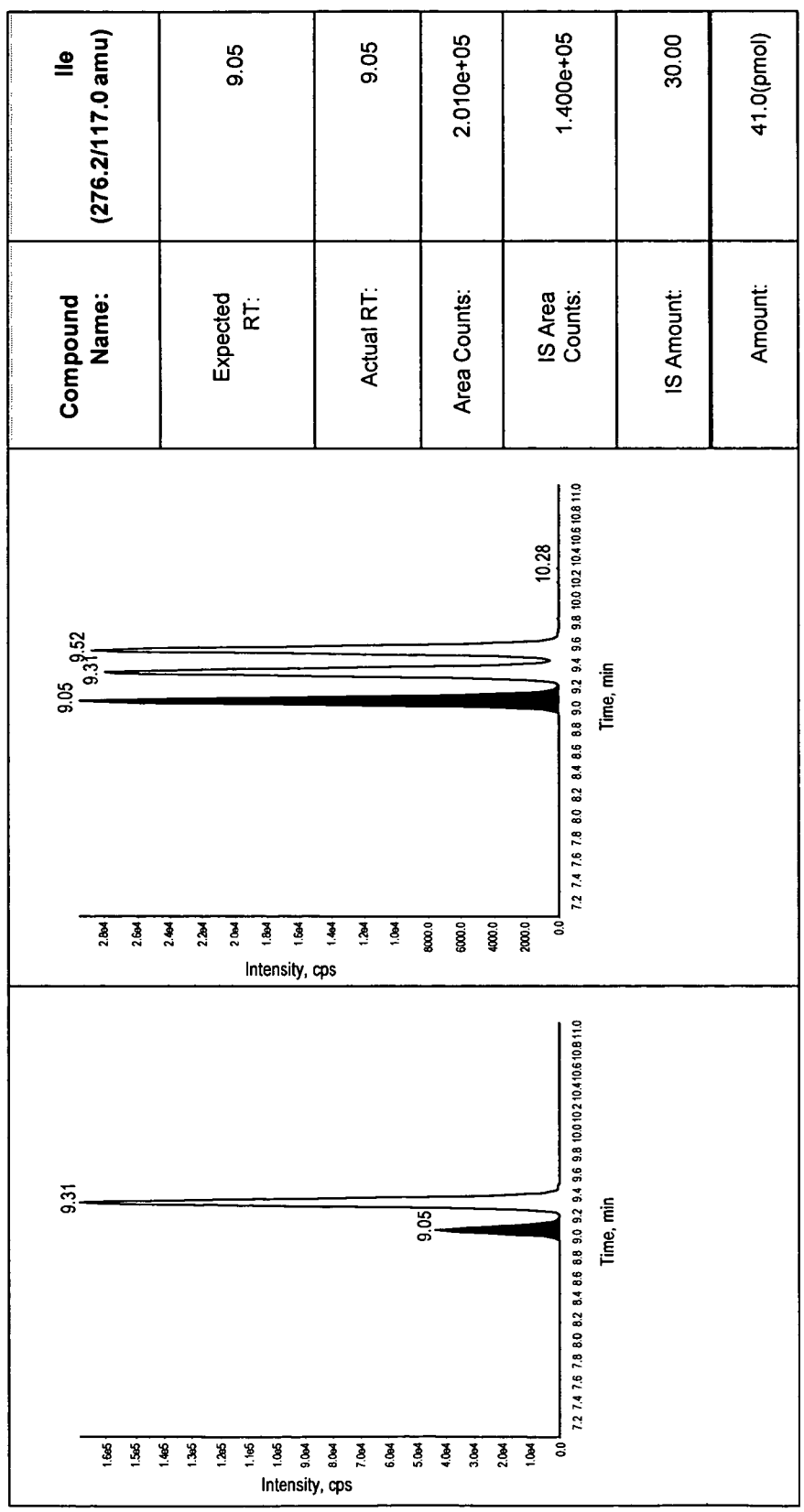
Figure 25S:
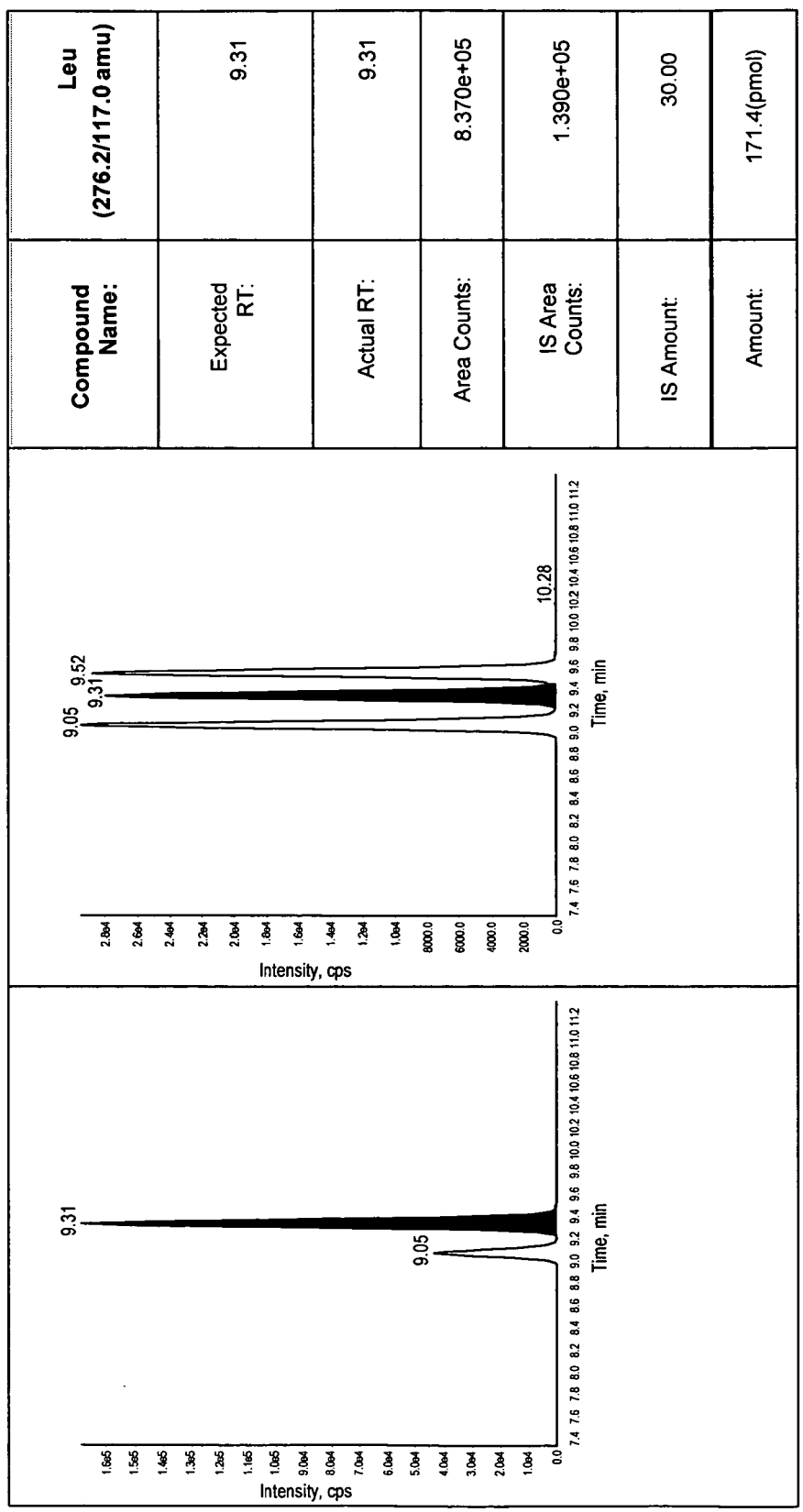
Figure 25T:
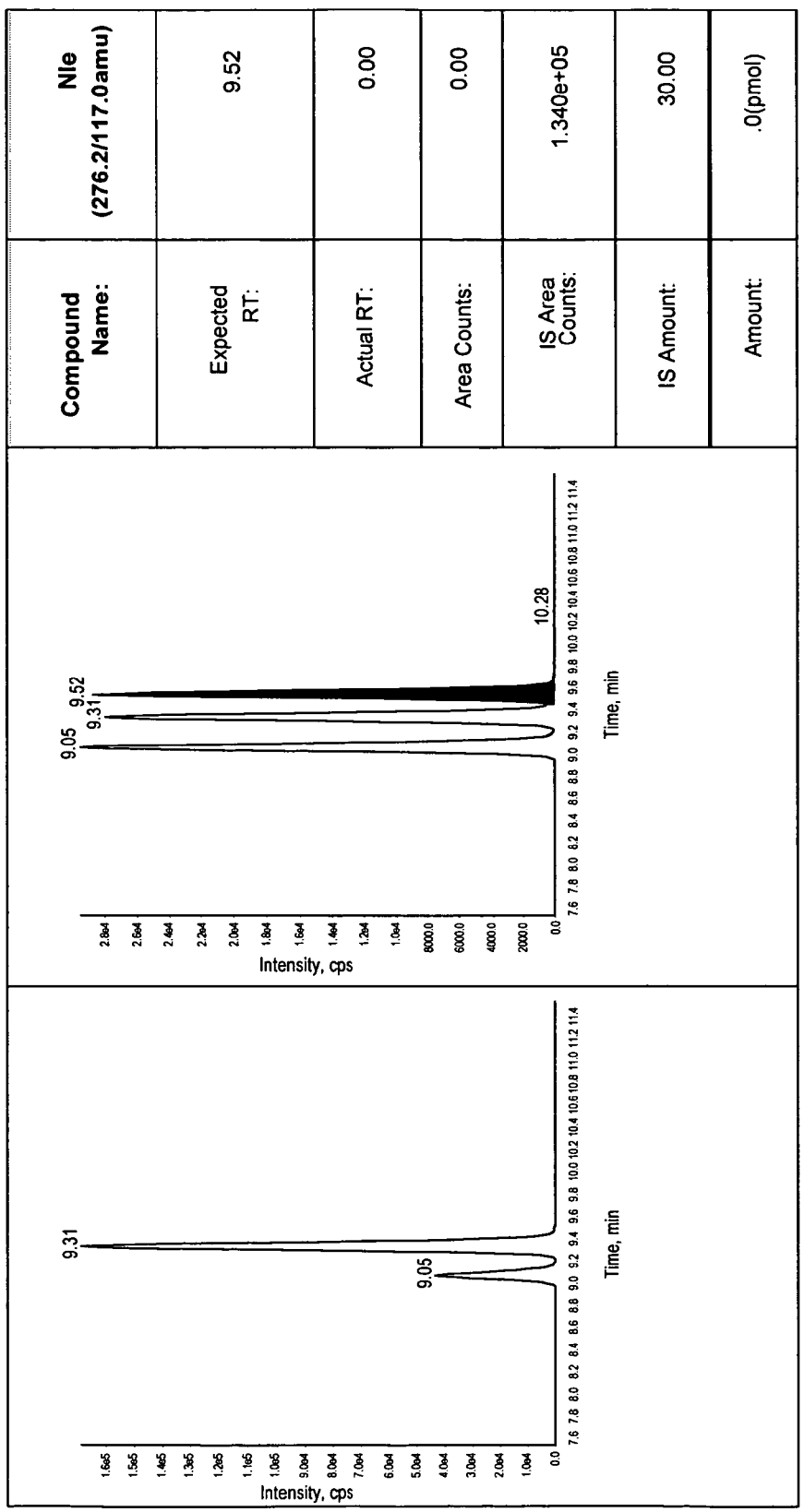
Figure 25U:
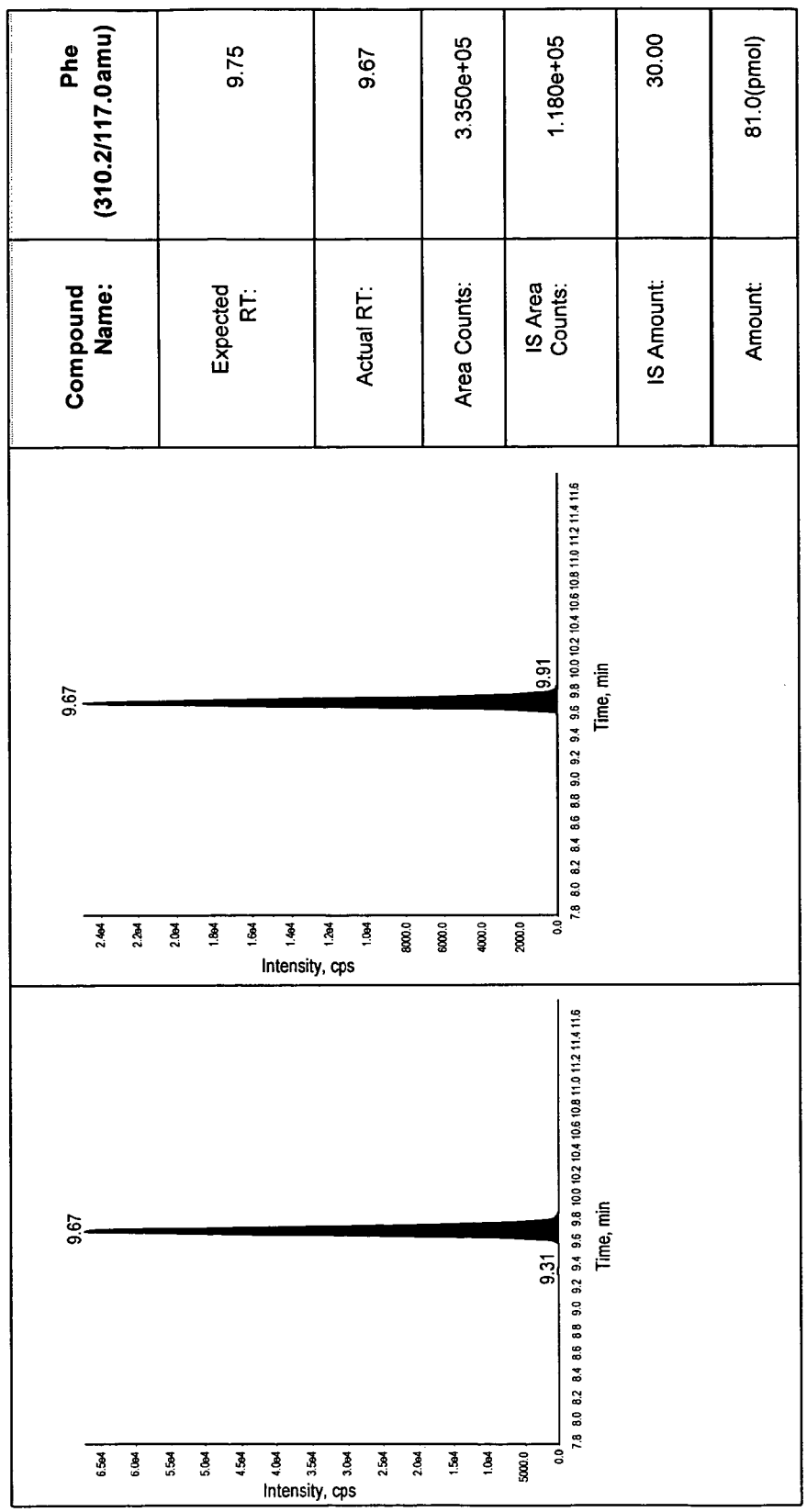

FIGS. 25A-25U schematically depict PDITM spectra of various amino acids measured in Example 5.

Figure 26A:
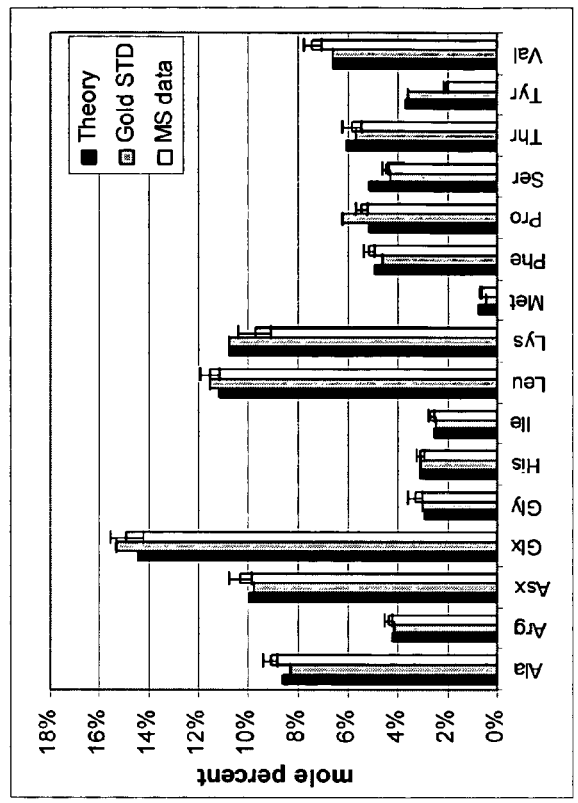
Figure 26B:
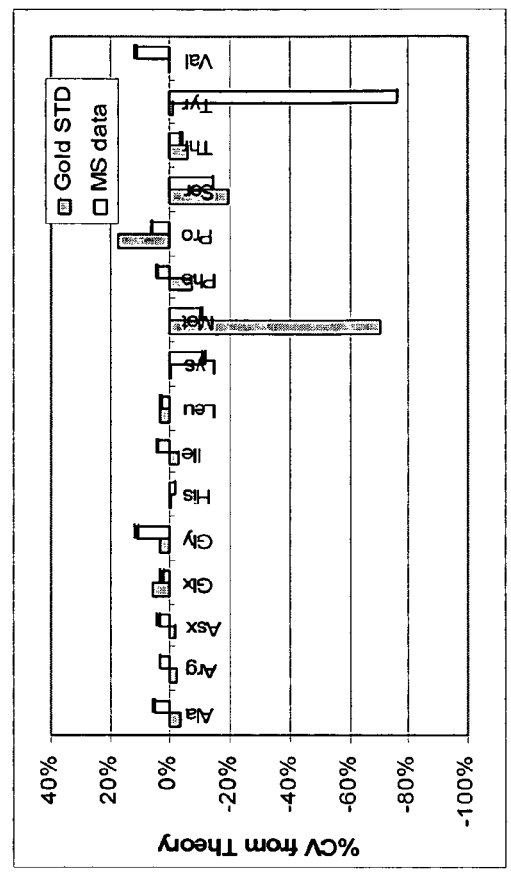

FIGS. 26A-26B present data comparing the measured amino acid concentrations of Example 5 to theory and various other measurement systems.

Figure 27A:
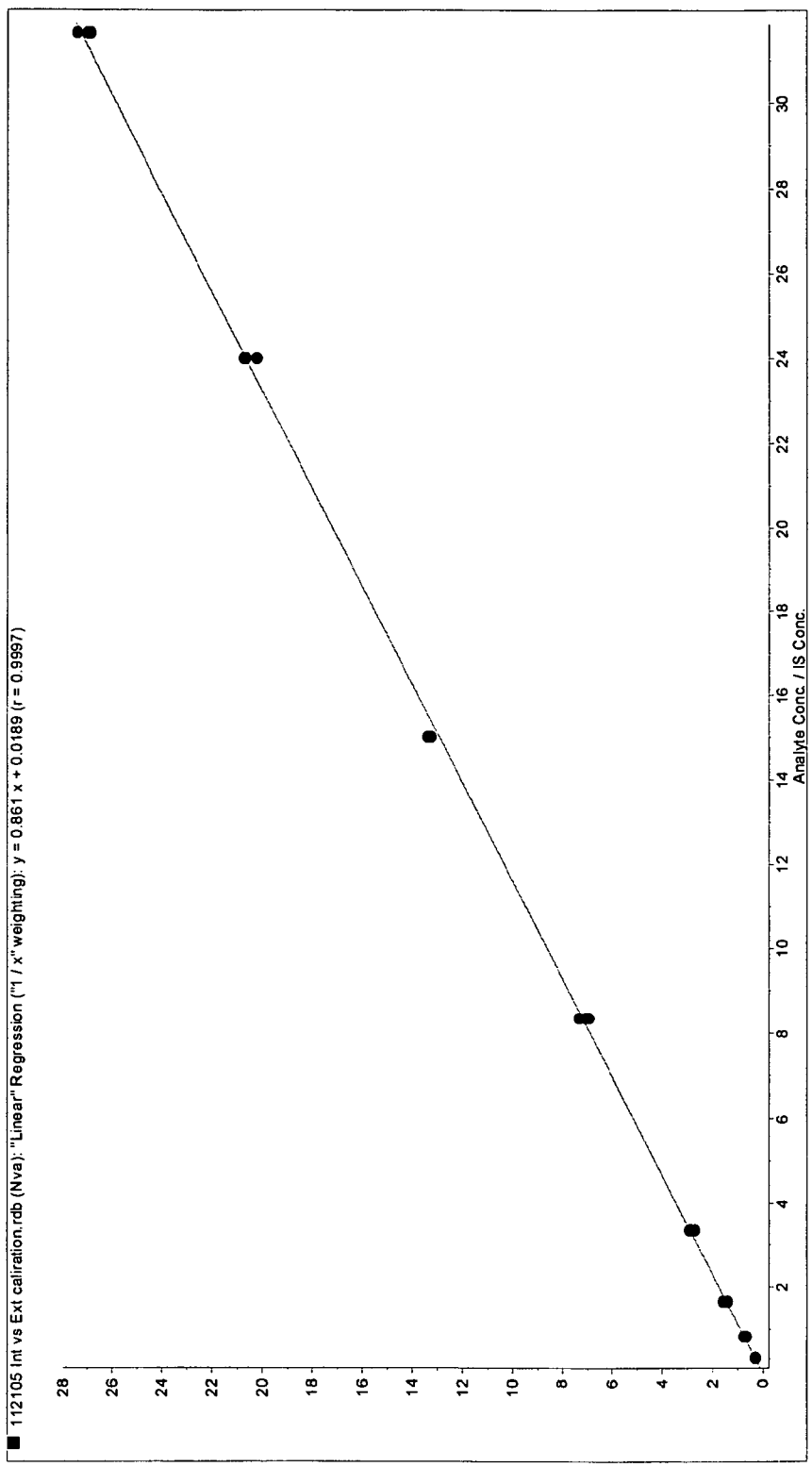
Figure 27B:
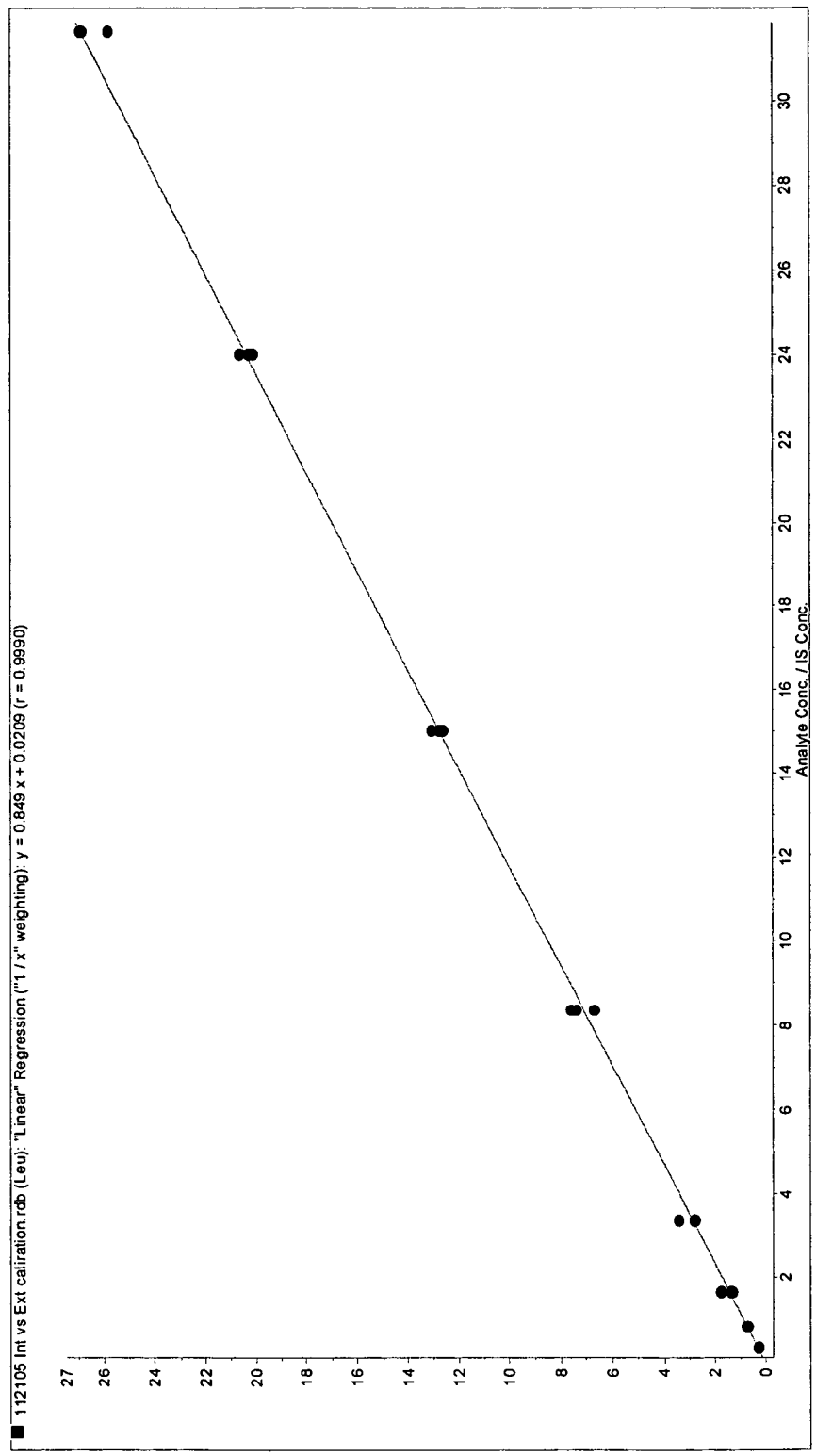

FIGS. 27A and 27B present data on the dynamic range and response of various embodiments of the present teachings for the determination of amino acid concentrations.

DESCRIPTION OF VARIOUS EMBODIMENTS

Figure 1:
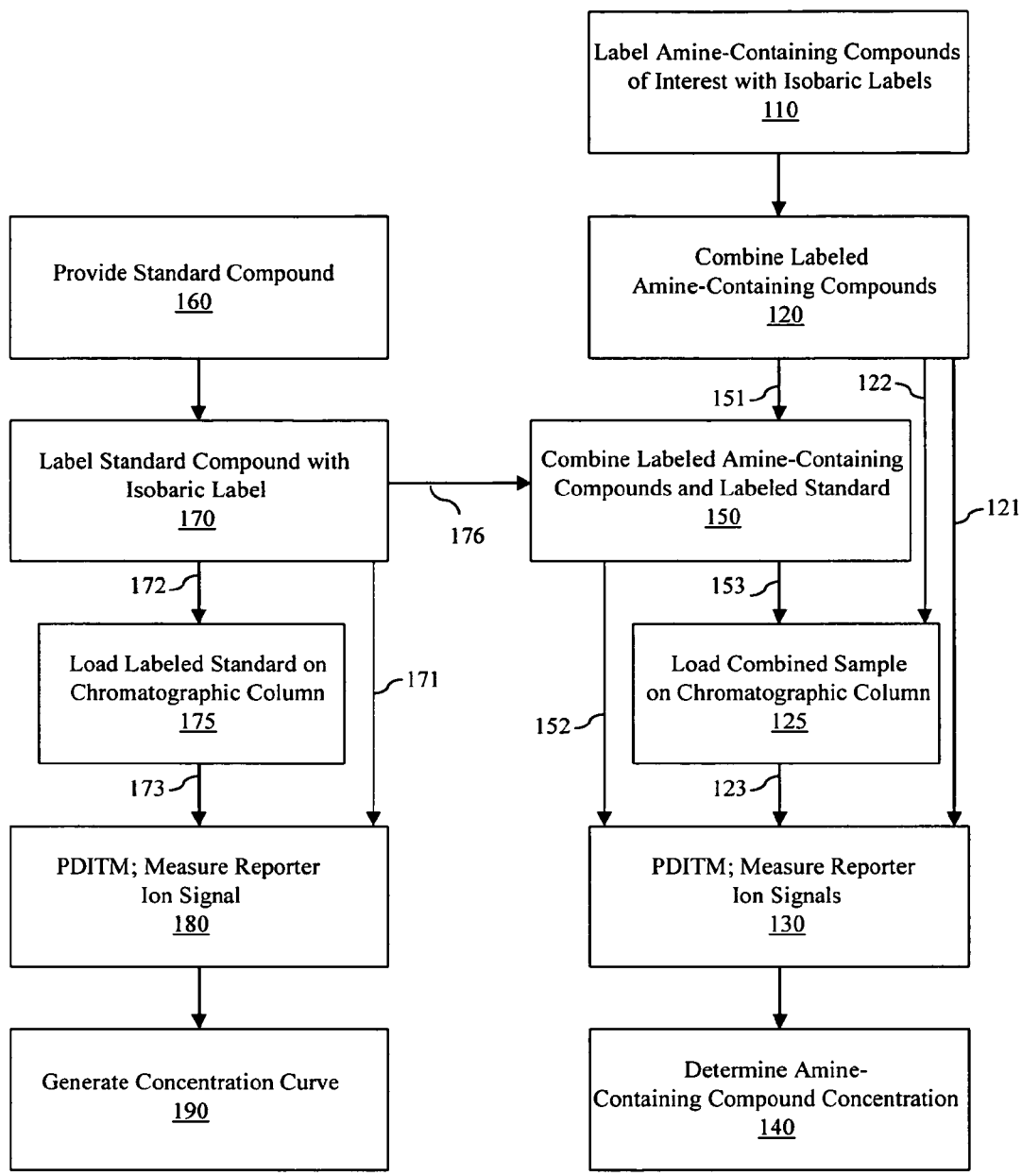

In various aspects, the present teachings provide methods for analyzing one or more amine-containing compounds in one or more samples using isobaric labels and parent-daughter ion transition monitoring (PDITM). In various embodiments, the present teachings provide methods for determining the concentration of one or more of amine-containing compounds. For example, referring to FIG. 1, in various embodiments, a method comprises the steps of labeling one or more amine-containing compounds each with a different isobaric tag from a set of isobaric tags (step 110), each isobaric tag from the set of isobaric tags comprising a reporter ion portion; combining at least a portion of each of the isobarically labeled amine-containing compounds to produce a combined sample (step 120) and subjecting at least a portion of the combined sample to parent-daughter ion transition monitoring (where the transmitted parent ion m/z range includes a m/z value of the isobarically labeled amine-containing compound and the transmitted daughter ion m/z range includes a m/z value of a reporter ion corresponding to the isobaric tag of the isobarically labeled amine-containing compound) and measuring the ion signal of one or more of the transmitted reporter ions (step 130); then determining the concentration of one or more of the isobarically labeled amine-containing compounds based at least on a comparison of the measured ion signal of the corresponding reporter ion to one or more measured ion signals of a standard compound (step 140). The ion signal(s) can, for example, be based on the intensity (average, mean, maximum, etc.) of the ion peak, an area of the ion peak, or a combination thereof.

In various embodiments, PDITM can be performed on a mass analyzer system comprising a first mass separator, and ion fragmentor and a second mass separator. The transmitted parent ion m/z range of a PDITM scan (selected by the first mass separator) is selected to include a m/z value of one or more of the isobarically labeled amine-containing compounds and the transmitted daughter ion m/z range of a PDITM scan (selected by the second mass separator) is selected to include a m/z value one or more of the reporter ions corresponding to the transmitted amine-containing compound.

In various embodiments, the one or more amine-containing samples are labeled with one or more of isobaric tags selected from a set of isobaric tags, so that, for example, within one experimental measurement: (i) multiple amine-containing compounds from different samples (e.g., a control, treated) can be compared; (ii) multiple concentration measurements can be determined on the same amine-containing compound from the same sample; (iii) different isolates of cancer tissue can be evaluated against normal tissue; (iv) antibiotic contaminated food or beverage can be evaluated against non-contaminated food or beverage; (v) flavor trends between different samples of food or beverage can be compared; (vi) the progress of fermentation can be monitored; etc.

Referring again to FIG. 1, in various embodiments, the step of subjecting at least a portion of the combined sample to PDITM comprises introducing the combined sample directly into a mass analyzer system (workflow path 121 and step 130), e.g., by introduction of the combined sample in a suitable solution using an electrospray ionization (ESI) ion source, mixing the combined sample with a suitable matrix and introducing the sample using a suitable matrix assisted laser desorption/ionization (MALDI) ion source.

Referring again to FIG. 1, in various embodiments, the step of subjecting at least a portion of the combined sample to PDITM comprises loading the portion of the combined sample on a chromatographic column (e.g., a LC column, a gas chromatography (GC) column, or combinations thereof) (workflow path 122 and step 125), subjecting at least a portion of the eluent from the chromatographic column to parent-daughter ion transition monitoring and measuring the ion signal of one or more of the transmitted reporter ions (workflow path 123 and step 130).

In various embodiments, the combined sample is cleaned up (e.g., to remove, e.g., interfering sample, buffer artifacts, etc; by high performance liquid chromatography (HPLC), reverse phase (RP)-HPLC, exchange fractionation, cation exchange, high resolution cation exchange, etc., and combinations thereof) before it is used to measure a reporter ion signal.

In various embodiments, the concentration of an amine-containing compound is determined by comparing the measured ion signal of the corresponding amine-containing compound-reporter ion transition (the amine-containing compound-reporter ion transitions signal) to one or more of:

(i) a concentration curve for a standard compound-reporter ion transition; and (ii) a standard compound-reporter ion transition signal for a standard compound in the combined sample with the amine-containing compound.

Referring again to FIG. 1, the one or more measured ion signals of a standard compound used in the step of determining the concentration of one or more of the isobarically labeled amine-containing compounds (step 140) can be provided in many ways. In various embodiments, one or more standard compounds are labeled with an isobaric tag from the set of isobaric tags and at least a portion of one or more of the one or more isobarically labeled standard compounds is combined with at least a portion of each of the isobarically labeled amine-containing compounds to produce a combined sample (step 150); followed by subjecting at least a portion of this combined sample to PDITM and measuring the ion signal of one or more of the transmitted reporter ions (step 130).

The measured ion signals of one or more of the reporters ions corresponding to one or more of the one or more of isobarically labeled standard compounds in the combined sample can then be used in determining the concentration of one or more of the isobarically labeled amine-containing compounds. Accordingly, in various embodiments, determining the concentration of an isobarically labeled amine-containing compound is based at least on a comparison of the measured ion signal of the corresponding reporter ion to the measured ion signal of one or more reporter ions corresponding to one or more of the one or more of isobarically labeled standard compounds in the combined sample (step 140). The step of subjecting at least a portion of this combined sample to PDITM can comprise, e.g., a direct introduction into a mass analyzer system (workflow path 152 and step 130); first loading at least a portion of this combined sample on a chromatographic column (workflow path 153 and step 125) followed by subjecting at least a portion of the eluent from the chromatographic column to PDITM and measuring the ion signal of one or more of the transmitted reporter ions (workflow path 123 and step 130); or combinations thereof.

In various embodiments, determining the concentration of one or more of the isobarically labeled amine-containing compounds (step 140) is based at least on a comparison of the measured ion signal of the corresponding reporter ion to the measured ion signal of one or more reporter ions corresponding to one or more concentration curves of one or more standard compounds. In various embodiments, a standard compound is provided having a first concentration (step 160) and labeled with an isobaric tag from the set of isobaric tags (step 170). At least a portion of the isobarically labeled standard compound is subjected to parent-daughter ion transition monitoring (where the transmitted parent ion m/z range includes a m/z value of the isobarically labeled standard compound and the transmitted daughter ion m/z range includes a m/z value of a reporter ion corresponding to the isobaric tag of the isobarically labeled standard compound) and the ion signal of the reporter ion is measured (step 180). The steps of labeling (step 170) and the steps of PDITM and measuring the ion signal of the transmitted reporter ions (step 180) are repeated for at least on or more standard compound concentrations different from the first concentration to generate a concentration curve for the standard compound (step 190).

The step of subjecting at least a portion of the isobarically labeled standard compound to PDITM can comprise, e.g., a direct introduction into a mass analyzer system (workflow path 171 and step 180) (e.g., by introduction of the combined sample in a suitable solution using an ESI ion source, mixing the combined sample with a suitable matrix and introducing the sample using a suitable MALDI ion source); first loading at least a portion of this combined sample on a chromatographic column (workflow path 172 and step 175) followed by subjecting at least a portion of the eluent from the chromatographic column to PDITM and measuring the ion signal of one or more of the transmitted reporter ions (workflow path 173 and step 180); or combinations thereof.

In various embodiments, PDITM on a standard compound can be performed on a mass analyzer system comprising a first mass separator, and ion fragmentor and a second mass separator. The transmitted parent ion m/z range of a PDITM scan (selected by the first mass separator) is selected to include a m/z value of one or more of the isobarically labeled standard compounds and the transmitted daughter ion m/z range of a PDITM scan (selected by the second mass separator) is selected to include a m/z value one or more of the reporter ions corresponding to the transmitted standard compound.

In various embodiments, the generation of a concentration curve can use one or more internal standards included in at least a portion of the standard compound to, e.g., facilitate concentration determination, account for differences in injection volumes, etc.

In various embodiments, a concentration curve can be generated by using PDITM to measure the ion signal of a reporter ion associated with the corresponding standard compound and generating a concentration curve by linear extrapolation of the measured concentration such that zero concentration corresponds to zero reporter ion signal. In various embodiments, a concentration curve can be generated by using PDITM to measure the ion signal of a reporter ion associated with the corresponding standard compound at two or more known concentrations and generating a concentration curve by fitting a function to the measured reporter ion signals. Suitable fitting functions can depend, for example, on the response of the detector (e.g., detector saturation, non-linearity, etc.). In various embodiments, the fitting function is a linear function.

In various embodiments, determining the concentration of one or more of the isobarically labeled amine-containing compounds (step 140) is based at least on both: (i) a comparison of the measured ion signal of the corresponding reporter ion to the measured ion signal of one or more reporter ions corresponding to one or more concentration curves of one or more standard compounds, and (ii) a comparison of the measured ion signal of the corresponding reporter ion to the measured ion signal of one or more reporter ions corresponding to one or more isobarically labeled standard compounds combined with the isobarically labeled amine-containing compounds. In various embodiments, a standard compound is provided having a first concentration (step 160) and labeled with an isobaric tag from the set of isobaric tags (step 170) used to label the one or more amine-containing compounds (e.g., of step 120). A portion of the isobarically labeled standard compound is combined with at least a portion of each of the isobarically labeled amine-containing compounds to produce a combined sample (workflow path 176 and step 150), and this combined sample can then be further analyzed as described herein. In various embodiments, a portion of the same isobarically labeled standard compound used to produce the combined sample is also used in generating a concentration curve, as described herein.

The same standard compound portion used to measure a reporter ion signal, or another portion, can be used to determine parent-daughter ion transition monitoring conditions for the mass analyzer. For example, where the mass analyzer system comprises a liquid chromatography (LC) component, the standard compound can be used to determine chromatography retention times. In various embodiments, the standard compound can be used to determine for a amine-containing compound its ionization efficiency in the ion source and fragmentation efficiency in the ion fragmentor under various conditions.

Amine-Containing Compounds

The methods of the present teachings can be applied to a wide variety of primary and secondary amine-containing compounds, including, but not limited to, amino acids, catecholamines, nitrofuran metabolites, polyamines, peptides, proteins, polypeptides, and combinations thereof.

In various embodiments, an amine-containing compound of interest comprises an amino acid. Examples of amino acids include, but are not limited to, leucine, proline, alanine, valine, glycine, serine, asparagine, glutamine, aspartic acid, glutamic acid, methionine, tryptophan, phenylalanine, isoleucine, threonine, cysteine, tyrosine, histidine, lysine, arginine, and isomers thereof, and post-translationally modified amino acids thereof.

In various embodiments, an amine-containing compound of interest comprises one or more catecholamines. Examples of catecholamines include, but are not limited to, epinephrine, norepinephine, dopamine, and combinations thereof. In various embodiments, an amine-containing compound of interest comprises a polyamine. Examples of polyamines, include, but are not limited to, spermine, N-acetylspermine, spermidine, N-acetylspermidine, putrescine (1,4-diaminobutane), 2-hydroxypurtescine, cadaverine (1,5-diaminopentane), 1,6-diamineohexane, 1,7-diaminoheptane, 1,10-diaminododecanes, and combinations thereof. In various embodiments, an amine-containing compound of interest comprises a protein or polypeptide. Examples of proteins and polypeptides include, but are not limited to, cytochrome P450 isoforms, angiotensins, and whey and milk proteins such as beta lactoglobulin. Examples of the cytochrome P450 isoforms include, but are not limited to, Cyp1a2, Cyp1b1, Cyp2a4, Cyp2a12, Cyp2b10, Cyp2c29, Cyp2c37, Cyp2c39, Cyp2c40, Cyp2d9, Cyp2d22, Cyp2d26, Cyp2j5, Cyp2e1, Cyp3a11, Cyp4a10, Cyp4a14, and combinations thereof. In various embodiments, an amine-containing compound of interest comprises a nitrofuran metabolite. Examples of nitrofuran metabolites include, but are not limited to, 3-amino-2-oxazolidinone (AOZ), 5-morpholinomethyl-3-amino-oxazolidinone (AMOZ), semicarbazide (SEM), 1-aminohydantoin (AHD), and combinations thereof.

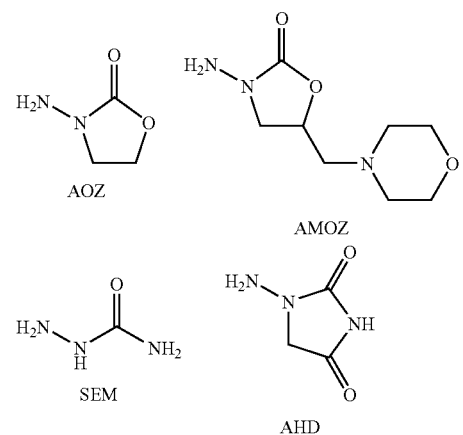

AOZ

AMOZ

SEM

AHD

The amine-containing compounds to which various embodiments of the present teachings can be applied can come from a wide variety of source types such as, for example, physiological fluid samples, cell or tissue lysate samples, synthetic peptide samples, polypeptide samples, protein samples, cell culture samples, fermentation broth media samples, agricultural product samples, animal product samples, animal feed samples, samples of food or beverage for human consumption, and combinations thereof. The samples can be from different sources, conditions, or both; for example, control vs. experimental, samples from different points in time (e.g. to form a sequence), disease vs. normal, experimental vs. disease, contaminated vs. non-contaminated, etc. Examples of physiological fluids, include, but are not limited to, blood, serum, plasma, sweat, tears, urine, peritoneal fluid, lymph, vaginal secretion, semen, spinal fluid, ascetic fluid, saliva, sputum, breast exudates, and combinations thereof. Examples of foods or beverages for human consumption include, but are not limited to, wine, honey, soy sauce, poultry, pork, beef, fish, shellfish, and combinations thereof. In various embodiments, the amine-containing compounds of interest are amino acids and the source of the amino acids comprises proteins which are, e.g., hydrolyzed, digested, to produce the amino acids. In various embodiments, the amine-containing compounds of interest are synthetic peptides.

Standard Compounds

A wide variety of compounds can be used as standard compounds. In various embodiments, a standard compound comprises one of the amine-containing compounds of interest. In various embodiments, the standard compound is from one or more control samples, samples of known concentration, or combinations thereof. In various embodiments, a standard compound is provided for each amine-containing compound of interest in the analysis.

In various embodiments, a concentration curve for a standard compound can be generated using PDITM to measure the ion signal of a reporter ion associated with the standard compound at two or more known concentrations.

Isobaric Tags

In various embodiments, an isobaric tag can be represented by the general formula (I):

R-L-ARG  (I), where R represents a reporter group (R) covalently linked to an amine reactive group (ARG) though a cleavable linker group (L), the linker group including a balance group having a mass such that the mass of the R+L is substantially the same for each isobaric tag of the set of isobaric tags. For example, in various embodiments, the linker group L can be represented by the general formula (II):

X—B—Y  (II), where X represents a bond between the balance group and the reporter group, where the bond X breaks upon collision of the labeled analyte with a neutral gas (e.g., via collision induced dissociation), Y represents a bond between the balance group and the analyte when the analyte reactive group has been reacted with the analyte to label the analyte, and where B represents the balance group. Analytes can be labeled by reaction of the analyte with the reagent of formula (I), a salt thereof and/or a hydrate thereof.

Amine Reactive Group

Examples of amine reactive groups include, but are not limited to, those groups that selectively react with an amine functional group to form covalent or non-covalent bond with the amine-containing compound at specific sites. The amine reactive group can be preexisting or it can be prepared in-situ. In-situ preparation of the amine reactive group can proceed in the absence of the analyte or it can proceed in the presence of the analyte. For example, a carboxylic acid group can be modified in-situ with water-soluble carbodiimide (e.g. 1-(3-dimethylaminopropyl)-3-ethylcarbodiimide hydrochloride; EDC) to thereby prepare an electrophilic group that can be reacted with a nucleophile such as an alkyl or aryl amine group. In various embodiments, activation of the carboxylic acid group of a labeling reagent with EDC can be performed in the presence of an amine (nucleophile) containing analyte. In various embodiments, the amine (nucleophile) containing analyte can also be added after the initial reaction with EDC is performed. In various embodiments, the reactive group can be generated in-situ by the in-situ removal of a protecting group. Consequently, any existing or newly created reagent or reagents that can effect the derivatization of analytes by the reaction of nucleophiles and/or electrophiles are contemplated.

In various embodiments, suitable amine reactive groups comprise an active ester. Active esters are well known in peptide synthesis and refer to certain esters that are easily reacted with the N-α amine of an amino acid under conditions commonly used in peptide synthesis. The amine reactive active ester can be, e.g., an N-hydroxysuccinimidyl ester (NHS), a N-hydroxysulfosuccinimidyl ester, a pentafluorophenyl ester (Pfp), a 2-nitrophenyl ester, a 4-nitrophenyl ester, a 2,4-dinitrophenylester or a 2,4-dihalophenyl ester. In various embodiments, the amine reactive group can be a mixed anhydride since mixed anhydrides can efficiently react with amine groups to thereby produce amide bonds.

Reporter Group

The reporter group of the isobaric tag or tags used in various embodiments of the present teachings can be a group that has a unique mass (or mass to charge ratio) that can be determined. For example, each reporter of a set can have a unique gross mass. Different reporters can comprise one or more heavy atom isotopes to achieve their unique mass. For example, isotopes of carbon ($^{12}C$, $^{13}C$ and $^{14}C$), nitrogen ($^{14}N$ and $^{15}N$), oxygen ($^{16}O$ and $^{18}O$) or hydrogen (hydrogen, deuterium and tritium) exist and can be used in the preparation of a diverse group of reporter moieties. Examples of stable heavy atom isotopes include, but are not limited to, $^{13}C$, $^{15}N$, $^{18}O$ and deuterium.

A unique reporter can be associated with a sample of interest thereby labeling one or multiple analytes of that sample with the reporter. In this way, e.g., information about the reporter can be associated with information about one or all of the analytes of the sample. However, the reporter need not be physically linked to an analyte when the reporter is determined. Rather, the unique gross mass of the reporter can, for example, be determined in a second mass analysis of a tandem mass analyzer, after ions of the labeled analyte are fragmented to thereby produce daughter fragment ions and detectable reporters. The determined reporter can be used to identify the sample from which a determined analyte originated. Further, the amount of the unique reporter, either relative to the amount of other reporters or relative to a calibration standard (e.g. an analyte labeled with a specific reporter), can be used to determine the relative or absolute amount (often expressed as a concentration and/or quantity) of analyte in the sample or samples. Therefore information, such as the amount of one or more analytes in a particular sample, can be associated with the reporter moiety that is used to label each particular sample. Where the identity of the analyte or analytes is also determined, that information can be correlated with information pertaining to the different reporters to thereby facilitate the determination of the identity and amount of each labeled analyte in one or a plurality of samples.

The reporter can comprise a fixed charge or can be capable of becoming ionized. Because the reporter can comprise a fixed charge or can be capable of being ionized, the labeling reagent might be isolated or used to label the reactive analyte in a salt (or a mixture of salts) or zwitterionic form. Ionization of the reporter facilitates its determination in a mass spectrometer. Accordingly, the reporter can be determined as an ion, sometimes referred to as a signature ion. When ionized, the reporter can comprise one or more net positive or negative charges. Thus, the reporter can comprise one or more acidic groups or basic groups since such groups can be easily ionized in a mass spectrometer. For example, the reporter can comprise one or more basic nitrogen atoms (positive charge) or one or more ionizable acidic groups such as a carboxylic acid group, sulfonic acid group or phosphoric acid group (negative charge). Non-limiting examples of reporters comprising a basic nitrogen include, substituted or unsubstituted, morpholines, piperidines or piperazines.

The reporter can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label comprises one or more heavy atom isotopes. The heterocyclic ring can be substituted or unsubstituted. The heterocyclic ring can be aliphatic or aromatic. Possible substituents of the heterocylic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

The reporter can be selected so that it does not substantially sub-fragment under conditions typical for the analysis of the analyte. The reporter can be chosen so that it does not substantially sub-fragment under conditions of dissociative energy applied to cause fragmentation of both bonds X and Y of at least a portion of selected ions of a labeled analyte in a mass spectrometer. By "does not substantially sub-fragment" we mean that fragments of the reporter are difficult or impossible to detect above background noise when applied to the successful analysis of the analyte of interest. The gross mass of a reporter can be intentionally selected to be different as compared with the mass of the analyte sought to be determined or any of the expected fragments of the analyte. For example, where proteins or peptides are the analytes, the reporter's gross mass can be chosen to be different as compared with any naturally occurring amino acid or peptide, or expected fragments thereof. This can facilitate analyte determination since, depending on the analyte, the lack of any possible components of the sample having the same coincident mass can add confidence to the result of any analysis.

Linker Group

The linker of the labeling reagent or reagents used with various embodiments of the present teachings links the reporter to the analyte or the reporter to the analyte reactive group (ARG) depending on whether or not a reaction with the analyte has occurred. The linker can be selected to produce a neutral species when both bonds X and Y are fragmented (e.g., undergoes neutral loss upon fragmentation of both bonds X and Y). The of a linker can be a very small moiety such as a carbonyl or thiocarbonyl group. The linker can be a larger moiety. The linker can be a polymer or a biopolymer. The linker can be designed to sub-fragment when subjected to dissociative energy levels; including sub-fragmentation to thereby produce only neutral fragments of the linker.

The linker group can comprise one or more heavy atom isotopes such that its mass compensates for the difference in gross mass between the reporters for each labeled analyte of a mixture or for the isobaric reagents of set. Moreover, the aggregate gross mass (i.e. the gross mass taken as a whole) of the reporter/linker combination can be substantially the same for each labeled analyte of a mixture or for the reagents of set and/or kit. Because the linker can act as a mass balance for the reporter in the labeling reagents, such that the aggregate gross mass of the reporter/linker combination is the same for all reagents of a set or kit, the linker group is also referred to as comprising a balance group (B). The greater the number of atoms in the balance group (B) of the linker, the greater the possible number of different isomeric/isobaric labeling reagents of a set and/or kit.

Bonds X and Y

X is a bond between an atom of the reporter and an atom of the linker. Y is a bond between an atom of the linker and an atom of either the amine reactive group or, if the labeling reagent has been reacted with an analyte, the analyte. Bond X is selected such that in at least a portion of the selected ions of the labeled analytes (e.g., R—X—B—Y-analyte) bond X breaks when subjected to a sufficient dissociative energy level. In various embodiments, bond Y is also selected such that in at least a portion of the selected ions of the labeled analytes (e.g., R—X—B—Y-analyte) bond Y breaks when subjected to a sufficient dissociative energy level. A dissociative energy level can be adjusted in a mass spectrometer so that bond X, bond Y, or both Bond X and Y, break in at least a portion of the selected ions of the labeled analytes. Breaking of bond X releases the reporter from the analyte so that the reporter can be determined independently from the analyte. Breaking of bond Y releases the reporter/linker combination from the analyte, or the linker from the analyte, depending on whether or not bond X has already been broken. In various embodiments, bond Y can be more labile than bond X, bond X can be more labile than bond Y, or bonds X and Y can be of substantially the same relative lability.

When, for example, the analyte of interest is a protein or peptide, the relative lability of bonds X and Y can be adjusted with regard to an amide (peptide) bond. Bond X, bond Y or both bonds X and Y, can be more, equal or less labile as compared with a typical amide (peptide) bond. For example, under conditions of dissociative energy, bond X and/or bond Y can be less prone to breaking (fragmentation) as compared with the peptide bond of a Z-pro dimer or Z-asp dimer, wherein Z is any natural amino acid, pro is proline and asp is aspartic acid. In various embodiments, bonds X and Y will break with approximately the same level of dissociative energy as a typical amide bond.

Bonds X and Y can also exist such that breaking of bond Y results in the breaking of bond X, and vice versa. In various embodiments, both bonds X and Y can fragment essentially simultaneously such that no substantial amount of analyte, or daughter fragment ion thereof, comprises a partial label in the second mass analysis. By "substantial amount of analyte" we mean that less than about 25%, and preferably less than about 10%, partially labeled analyte can be determined in the MS/MS spectrum.

Figure 2:
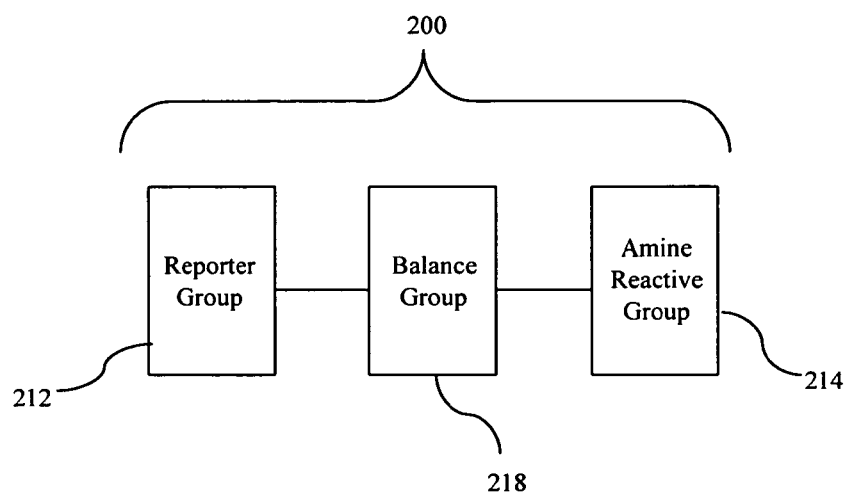

Referring to FIG. 2A, a schematic representation of isobaric tags 200 is illustrated. Each tag is comprised of a reporter group 212, an amine reactive group 214 and a balance group 218 (e.g., balancing out the difference in masses between the reporter groups) such that the nominal masses of each tag are substantially equal.

In various embodiments, a set of isobaric tags comprises amine-derivatized amine-containing compounds that are substantially chromatographically indistinguishable and substantially indistinguishable mass spectrometrically in the absence of fragmentation, but which produce strong low-mass MS/MS signature ions following CID.

In various embodiments, a set of isobaric tags comprises tags, Q114, Q115, Q116 and Q117, represented, respectively, by the general formulas (IIIa)-(IIId):

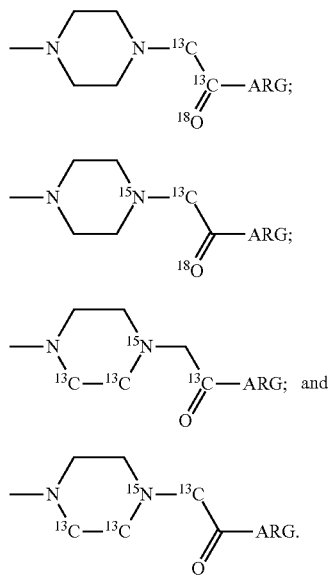

Further examples of reporter groups, linker groups, balance groups, amine reactive groups, isobaric tags and sets of isobaric tags suitable for use in various embodiments of the present teachings can be found in U.S. Publications Nos. 2004/0219686; 2004/0220412; 20050147982; 2005/0147985; 2005/0148087; 2005/0148771; 2005/0148773; 2005/0148774; and 2005/0208550 the entire contents of all of which are incorporated herein by reference.

Combined Samples

Any suitable combination of one or more isobarically labeled standard compounds, one or more isobarically labeled amine-containing compounds, or combinations thereof, can be used in the methods of the present teachings. For example, in general, the number of different isobarically labeled compounds in a combined sample, N, is less than or equal to the number, T, of isobaric tags in the set of isobaric tags. In any one combined sample, the possible of combinations of isobarically labeled standard compounds, one or more isobarically labeled amine-containing compounds can be expressed as:

$$(S+C) \leq T \quad (1),$$

where T represents the number of isobaric tags in the set of isobaric tags; S represents the number of isobarically labeled standard compounds with different isobaric labels and ranges from 0 to T inclusive; and C represents the number of isobarically labeled amine-containing compounds different isobaric labels and ranges from 0 to T inclusive.

For example, in various embodiments, one or more isobarically labeled standard compounds (e.g., from a control sample, from a sample of known concentration, etc.) is combined with one or more isobarically labeled amine-containing test compounds of interest, the one or more isobarically labeled standard compounds providing one or more reporter ion signals that can serve, e.g., as internal concentration standards. In various embodiments, the addition of an isobarically labeled standard compound can serve as an internal standard for one or more amine-containing compounds of interest in the combined sample. In various embodiments, a different isobarically labeled standard compound is added for each different amine-containing compound of interest in the combined sample (e.g., S=C), each different isobarically labeled standard compound, for example, serving as an internal standard for a different amine-containing compound of interest.

In various embodiments, two or more of the amine containing compounds to be analyzed in the combined sample comprise the same amine-containing compound of interest. For example, amine containing compounds #1 to #X (where X>1) can comprise the same amine-containing compound of interest but, e.g., from different samples a different isobaric label being used for the amine-containing compounds from different samples. For example, the different samples can be from different points in time for the same system (e.g., patient, location, etc.) and used e.g., to monitor the progression of some process, e.g., disease, fermentation, etc.

In various embodiments, a sample is processed with different isobaric tags used for the same amine-containing compound. For example, a sample is processed in triplicate, a different isobaric tag being used for each of the three portions which are then combined to provide at least in part the combined sample (which can also include one or more standard compounds); to provide, e.g, a three measurements of the concentration of the amine-containing compound in a single experimental analysis of the combined sample. Triplicate, or more generally multiplate measures, are often required to provide statistically significant and/or accurate results. For example, amino acid analysis results using traditional approaches are typically based on triplicate analysis of the same sample due to the run-to-run variations and background interferences that are commonly encountered in these traditional techniques. The ability of various embodiments of the present teachings to provide multiple measures of an amine-containing compounds concentration in a single experimental run can facilitate reducing the inaccuracy due to such run-to-run variations.

In various embodiments, an isobarically labeled standard compound is not added to the combined sample and, in various embodiments, e.g., the concentration of one or more of the amine-containing compounds of interest can be determined based at least on a comparison of the corresponding reporter ion signal of the amine-containing compound to a concentration curve of a standard compound.

In various embodiments, a combined sample is cleaned up (e.g., to remove, e.g., interfering sample, buffer artifacts, etc; by high performance liquid chromatography (HPLC), reverse phase (RP)-HPLC, exchange fractionation, cation exchange, high resolution cation exchange, etc., and combinations thereof) before it is used to measure a reporter ion signal.

Mass Analyzers

A wide variety of mass analyzer systems can be used in the present teachings to perform PDITM. Suitable mass analyzer systems include two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, or combinations thereof.

Examples of suitable mass spectrometry systems for the mass analyzer include, but are not limited to, those which comprise one or more of a triple quadrupole, a quadrupole-linear ion trap (e.g., 4000 Q TRAP® LC/MS/MS System, Q TRAP® LC/MS/MS System), a quadrupole TOF (e.g., QSTAR® LC/MS/MS System), and a TOF-TOF.

Suitable ion sources for the mass spectrometry systems include, but are not limited to, an electrospray ionization (ESI), matrix-assisted laser desorption ionization (MALDI), atmospheric pressure chemical ionization (APCI), and atmospheric pressure photoionization (APPI) sources. For example, ESI ion sources can serve as a means for introducing an ionized sample that originates from a LC column into a mass separator apparatus. One of several desirable features of ESI is that fractions from the chromatography column can proceed directly from the column to the ESI ion source.

In various embodiments, the mass analyzer system comprises a MALDI ion source. In various embodiments, at least a portion of the combined sample is mixed with a MALDI matrix material and subjected to parent-daughter ion transition monitoring using a mass analyzer with a MALDI ionization source. In various embodiments, at least a portion of the combined sample loaded on chromatographic column and at least a portion of the eluent mixed with a MALDI matrix material and subjected to parent-daughter ion transition monitoring using a mass analyzer with a MALDI ionization source. Examples of MALDI matrix materials include, but are not limited to, those listed in Table 1.

TABLE 1

| Matrix Material | Typical Uses |
| --- | --- |
| 2,5-dihydroxybenzoic acid (2,5-DHB) MW 154.03 Da | Peptides, glycolipids, polar and non-polar synthetic polymers, neutral or basic carbohydrates, small molecules |
| Sinapinic Acid MW 224.07 Da | Peptides and Proteins >10,000 Da |
| a-cyano-4-hydroxy cinnamic acid (aCHCA) MW 189.04 Da | Peptides, proteins and PNAs <10,000 Da |
| 3-hydroxy-picolinic acid (3-HPA) MW 139.03 Da | Large oligonucleotides >3,500 Da |
| 2,4,6-Trihydroxy acetophenone (THAP) MW 168.04 Da | Small oligonucleotides <3,500 acidic carbohydrates, acidic glycopeptides |
| Dithranol MW 226.06 Da | Nonpolar synthetic polymers |
| Trans-3-indoleacrylic acid (IAA) MW 123.03 Da | Nonpolar polymers |
| 2-(4-hydroxyphenylazo)-benzoic acid (HABA) MW 242.07 Da | Proteins, Polar and nonpolar synthetic polymers |
| 2-aminobenzoic (anthranilic) acid MW 137.05 Da | Oligonucleotides (negative ions) |

In various embodiments, the mass spectrometer system comprises a triple quadrupole mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the parent ions to fragment. The third quadrupole is selected to transmit the selected daughter ion to a detector. In various embodiments, a triple quadrupole mass spectrometer can include an ion trap disposed between the ion source and the triple quadrupoles. The ion trap can be set to collect ions (e.g., all ions, ions with specific m/z ranges, etc.) and after a fill time, transmit the selected ions to the first quadrupole by pulsing an end electrode to permit the selected ions to exit the ion trap. Desired fill times can be determined, e.g., based on the number of ions, charge density within the ion trap, the time between elution of different signature peptides, duty cycle, decay rates of excited state species or multiply charged ions, or combinations thereof.

In various embodiments, one or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole selects the parent ion. The second quadrupole is maintained at a sufficiently high collision gas pressure and voltage so that multiple low energy collisions occur causing some of the parent ions to fragment. The third quadrupole is selected to trap fragment ions and, after a fill time, transmit the selected daughter ion to a detector by pulsing an end electrode to permit the selected daughter ion to exit the ion trap. Desired fill times can be determined, e.g., based on the number of fragment ions, charge density within the ion trap, the time between elution of different signature peptides, duty cycle, decay rates of excited state species or multiply charged ions, or combinations thereof.

In various embodiments, the mass spectrometer system comprises two quadrupole mass separators and a TOF mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the ions to fragment, and the TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof.

In various embodiments, the mass spectrometer system comprises two TOF mass analyzers and an ion fragmentor (such as, for example, CID or SID). In various embodiments, the first TOF selects the parent ion (e.g., by deflecting ions that appear outside the time window of the selected parent ions away from the fragmentor) for introduction in the ion fragmentor and the second TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof. The TOF analyzers can be linear or reflecting analyzers.

In various embodiments, the mass spectrometer system comprises a time-of-flight mass spectrometer and an ion reflector. The ion reflector is positioned at the end of a field-free drift region of the TOF and is used to compensate for the effects of the initial kinetic energy distribution by modifying the flight path of the ions. In various embodiments ion reflector consists of a series of rings biased with potentials that increase to a level slightly greater than an accelerating voltage. In operation, as the ions penetrate the reflector they are decelerated until their velocity in the direction of the field becomes zero. At the zero velocity point, the ions reverse direction and are accelerated back through the reflector. The ions exit the reflector with energies identical to their incoming energy but with velocities in the opposite direction. Ions with larger energies penetrate the reflector more deeply and consequently will remain in the reflector for a longer time. The potentials used in the reflector are selected to modify the flight paths of the ions such that ions of like mass and charge arrive at a detector at substantially the same time.

In various embodiments, the mass spectrometer system comprises a tandem MS-MS instrument comprising a first field-free drift region having a timed ion selector to select a parent ion of interest, a fragmentation chamber (or ion fragmentor) to produce daughter ions, and a mass separator to transmit selected daughter ions for detection. In various embodiments, the timed ion selector comprises a pulsed ion deflector. In various embodiments, the ion deflector can be used as a pulsed ion deflector. The mass separator can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In various embodiments, the mass spectrometer system comprises a tandem TOF-MS having a first, a second, and a third TOF mass separator positioned along a path of the plurality of ions generated by the pulsed ion source. The first mass separator is positioned to receive the plurality of ions generated by the pulsed ion source. The first mass separator accelerates the plurality of ions generated by the pulsed ion source, separates the plurality of ions according to their mass-to-charge ratio, and selects a first group of ions based on their mass-to-charge ratio from the plurality of ions. The first mass separator also fragments at least a portion of the first group of ions. The second mass separator is positioned to receive the first group of ions and fragments thereof generated by the first mass separator. The second mass separator accelerates the first group of ions and fragments thereof, separates the first group of ions and fragments thereof according to their mass-to-charge ratio, and selects from the first group of ions and fragments thereof a second group of ions based on their mass-to-charge ratio. The second mass separator also fragments at least a portion of the second group of ions. The first and/or the second mass separator may also include an ion guide, an ion-focusing element, and/or an ion-steering element. In various embodiments, the second TOF mass separator decelerates the first group of ions and fragments thereof. In various embodiments, the second TOF mass separator includes a field-free region and an ion selector that selects ions having a mass-to-charge ratio that is substantially within a second predetermined range. In various embodiments, at least one of the first and the second TOF mass separator includes a timed-ion-selector that selects fragmented ions. In various embodiments, at least one of the first and the second mass separators includes an ion fragmentor. The third mass separator is positioned to receive the second group of ions and fragments thereof generated by the second mass separator. The third mass separator accelerates the second group of ions and fragments thereof and separates the second group of ions and fragments thereof according to their mass-to-charge ratio. In various embodiments, the third mass separator accelerates the second group of ions and fragments thereof using pulsed acceleration. In various embodiments, an ion detector positioned to receive the second group of ions and fragments thereof. In various embodiments, an ion reflector is positioned in a field-free region to correct the energy of at least one of the first or second group of ions and fragments thereof before they reach the ion detector.

In various embodiments, the mass spectrometer system comprises a TOF mass analyzer having multiple flight paths, multiple modes of operation that can be performed simultaneously in time, or both. This TOF mass analyzer includes a path selecting ion deflector that directs ions selected from a packet of sample ions entering the mass analyzer along either a first ion path, a second ion path, or a third ion path. In some embodiments, even more ion paths may be employed. In various embodiments, the second ion deflector can be used as a path selecting ion deflector. A time-dependent voltage is applied to the path selecting ion deflector to select among the available ion paths and to allow ions having a mass-to-charge ratio within a predetermined mass-to-charge ratio range to propagate along a selected ion path.

For example, in various embodiments of operation of a TOF mass analyzer having multiple flight paths, a first predetermined voltage is applied to the path selecting ion deflector for a first predetermined time interval that corresponds to a first predetermined mass-to-charge ratio range, thereby causing ions within first mass-to-charge ratio range to propagate along the first ion path. In various embodiments, this first predetermined voltage is zero allowing the ions to continue to propagate along the initial path. A second predetermined voltage is applied to the path selecting ion deflector for a second predetermined time range corresponding to a second predetermined mass-to-charge ratio range thereby causing ions within the second mass-to-charge ratio range to propagate along the second ion path. Additional time ranges and voltages including a third, fourth etc. can be employed to accommodate as many ion paths as are required for a particular measurement. The amplitude and polarity of the first predetermined voltage is chosen to deflect ions into the first ion path, and the amplitude and polarity of the second predetermined voltage is chosen to deflect ions into the second ion path. The first time interval is chosen to correspond to the time during which ions within the first predetermined mass-to-charge ratio range are propagating through the path selecting ion deflector and the second time interval is chosen to correspond to the time during which ions within the second predetermined mass-to-charge ratio range are propagating through the path selecting ion deflector. A first TOF mass separator is positioned to receive the packet of ions within the first mass-to-charge ratio range propagating along the first ion path. The first TOF mass separator separates ions within the first mass-to-charge ratio range according to their masses. A first detector is positioned to receive the first group of ions that are propagating along the first ion path. A second TOF mass separator is positioned to receive the portion of the packet of ions propagating along the second ion path. The second TOF mass separator separates ions within the second mass-to-charge ratio range according to their masses. A second detector is positioned to receive the second group of ions that are propagating along the second ion path. In some embodiments, additional mass separators and detectors including a third, fourth, etc. may be positioned to receive ions directed along the corresponding path. In one embodiment, a third ion path is employed that discards ions within the third predetermined mass range. The first and second mass separators can be any type of mass separator. For example, at least one of the first and the second mass separator can include a field-free drift region, an ion accelerator, an ion fragmentor, or a timed ion selector. The first and second mass separators can also include multiple mass separation devices. In various embodiments, an ion reflector is included and positioned to receive the first group of ions, whereby the ion reflector improves the resolving power of the TOF mass analyzer for the first group of ions. In various embodiments, an ion reflector is included and positioned to receive the second group of ions, whereby the ion reflector improves the resolving power of the TOF mass analyzer for the second group of ions.

In another aspect of the present teachings, the functionality of the methods described herein may be implemented as computer-readable instructions on a general purpose computer. The computer may be separate from, detachable from, or integrated into a mass spectrometry system. The computer-readable instructions may be written in any one of a number of high-level languages, such as, for example, FORTRAN, PASCAL, C, C++, or BASIC. Further, the computer-readable instructions may be written in a script, macro, or functionality embedded in commercially available software, such as EXCEL or VISUAL BASIC. Additionally, the computer-readable instructions could be implemented in an assembly language directed to a microprocessor resident on a computer. For example, the computer-readable instructions could be implemented in Intel 80x86 assembly language if it were configured to run on an IBM PC or PC clone. In one embodiment, the computer-readable instructions be embedded on an article of manufacture including, but not limited to, a computer-readable program medium such as, for example, a floppy disk, a hard disk, an optical disk, a magnetic tape, a PROM, an EPROM, CD-ROM, DVD-ROM.

EXAMPLES

Aspects of the present teachings may be further understood in light of the following examples, which are not exhaustive and which should not be construed as limiting the scope of the present teachings in any way.

Example 1

Compounds from Different Sample Types

The following example illustrates the use of a variety of sample types. The teachings of this example are not exhaustive, and are not intended to limit the scope of these experiments or the present teachings Various embodiments of the analysis of one or more amine-containing compounds from various sample types using a method of the present teachings are illustrated. In various embodiments, the one or more of amine-containing compounds of interest can originate from one or more diverse sample types, e.g, plasma, wines, proteins, peptides and amino acids in this example. In general, a sample can be processed such that compounds of interest in a sample contain one or more amine groups suitable for labeling with an isobaric tag, such as, for example, primary and secondary amines.

Figure 3:
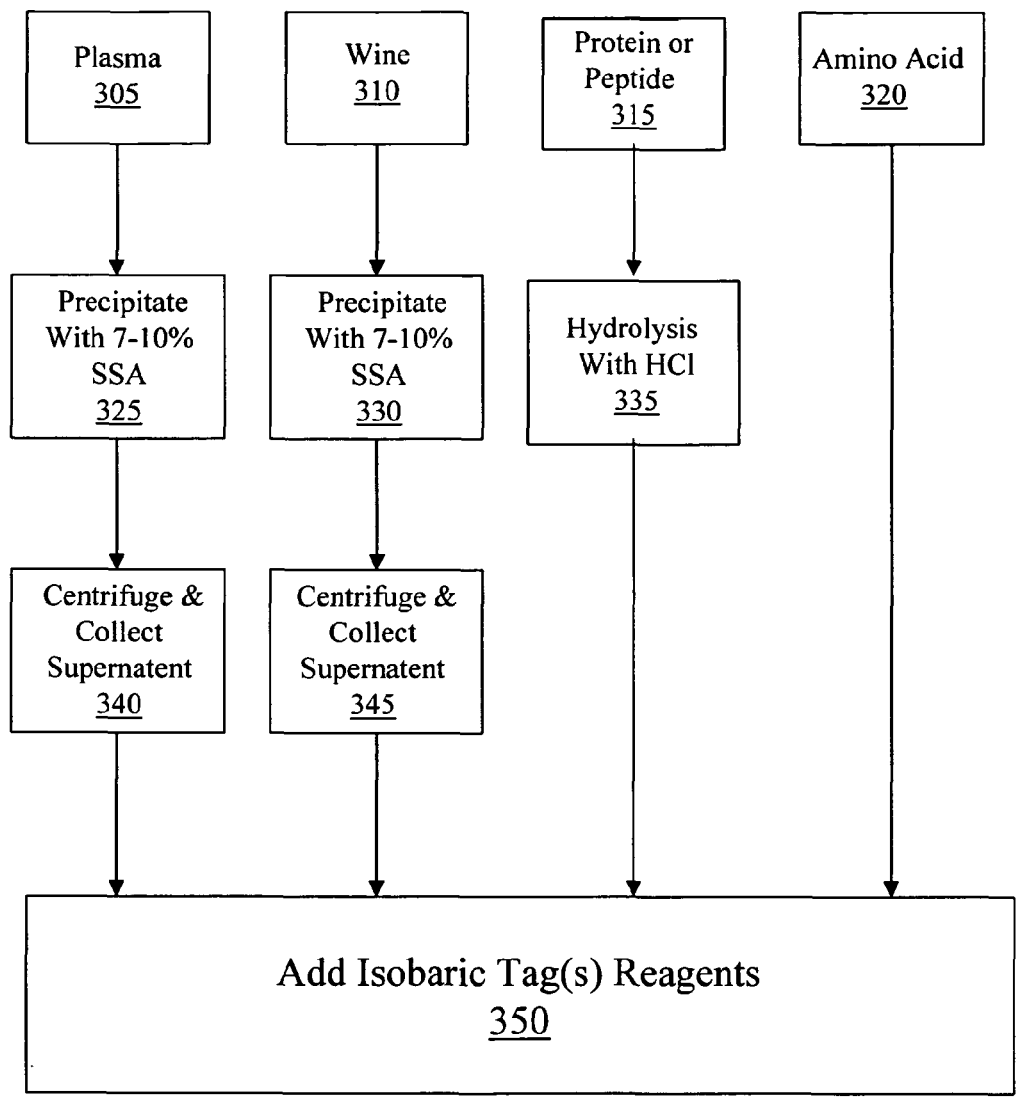
FIG. 3 is a schematic diagram of various embodiments using multiple sample types.

Referring to FIG. 3, in various embodiments, the labeling of one or more amine-containing compounds contained in a sample of plasma (block 305) comprises precipitating one or more of the amine-containing compounds of interest (step 325), followed by centrifugation and collection of at least a portion of the supernatant (step 340). A wide variety of approaches can be used to precipitate out an amine containing compound of interest including, but not limited to, a 7-10% sulfosalicyclic acid (SSA) solution, ethanol, isoproanol, and combinations thereof. At least a portion of the supernatant is then combined with one or more isobaric tags from a set of isobaric tags (e.g., iTRAQ™ brand reagents) (step 350) to prepare isobarically labeled amine-containing compounds of interest from the plasma sample.

In various embodiments, the labeling of one or more amine-containing compounds contained in a sample of wine (block 310) comprises precipitating one or more of the amine-containing compounds of interest with a 7-10% SSA solution (step 330), followed by centrifugation and collection of at least a portion of the supernatant (step 345). At least a portion of the supernatant is then combined with one or more isobaric tags from a set of isobaric tags (e.g., iTRAQ™ brand reagents) (step 350) to prepare isobarically labeled amine-containing compounds of interest from the wine sample.

In various embodiments, the labeling of one or more amine-containing compounds contained in a sample of proteins, peptides or polypeptides (block 315) comprises hydrolyzing (e.g, with 6 molar (M) hydrochloric acid (HCl)), digesting (e.g, with trypsin), or both, at least a portion of the sample (step 325) (e.g., to produce peptide and/or amino acid fragments) and combing the processed sample with one or more isobaric tags from a set of isobaric tags (e.g., iTRAQ™ brand reagents) (step 350) to prepare isobarically labeled amine-containing compounds of interest from the protein, peptide or polypeptide sample.

In various embodiments, the sample comprises an amino acid or mixture of amino acids (block 320) of which one or more of the amino acids comprise the amine-containing compounds of interest. In various embodiments, an amino acid sample can be combined with one or more isobaric tags from a set of isobaric tags (e.g., iTRAQ™ brand reagents) (step 350) to prepare isobarically labeled amine-containing compounds of interest from the amino acid sample. In various embodiments using iTRAQ™ brand reagents, the isobarically labeled amine-containing compounds of interest can be prepared without substantially altering one or more postranslation modifications.

Example 2

Sample Preparation and Labeling with iTRAQ™ Brand Reagents

The following example illustrates examples of various embodiments preparaing and labeling one or more samples comprising one or more proteins or peptides with one or more isobaric tags using iTRAQ™ brand reagents. The teachings of this example are not exhaustive, and are not intended to limit the scope of these experiments or the present teachings.

Reduction and of Protein or Peptide Samples and Cysteine Blocking

Figure 4A:
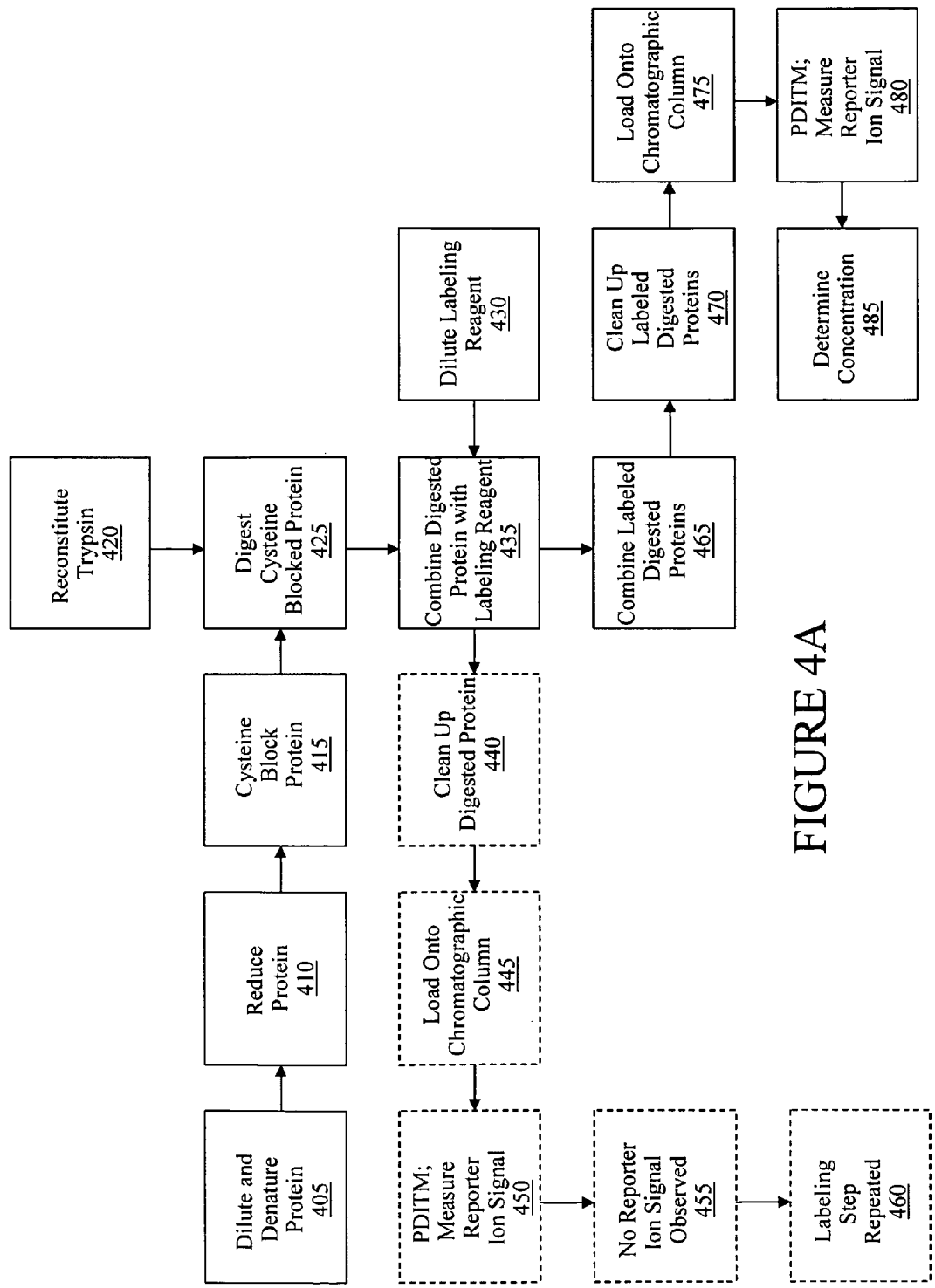
FIGS. 4A and 4B illustrate various embodiments of steps isobarically labeling using iTRAQ™ brand reagents.

Referring to FIG. 4A, in various embodiments, to each of at least one and up to four sample tubes, each containing between 5 and 100 μg of protein, is added 20 μL Dissolution Buffer and 1 μL Denaturant, followed by vortexing to mix (step 405). To each sample tube, 2 μL Reducing Reagent is added, followed by vortexing to mix and incubation at 60° C. for 1 hour (step 410). Spinning each sample tube is followed by addition of 1 μL Cysteine Blocking Reagent to each sample tube, then mixing by vortexing, spinning and incubation at room temperature for 10 minutes (step 415).

Digestion of Protein or Peptide Samples with Trypsin

Referring to FIG. 4A, in various embodiments, in various embodiments, where at least one and up to two sample tubes, each containing between 5 and 100 μg of reduced and cysteine blocked protein to be labeled, one vial of trypsin is reconstituted with 25 μL MillQ® Water or its equivalent. In other embodiments, for example, where at least one and up to four samples tubes, each containing between 5 and 100 μg of reduced and cysteine blocked protein to be labeled, two vials of tryspin are reconstituted with 25 μL MillQ® Water or its equivalent. Each of the diluted vials of trypsin are mixed by vortexing and spinning (step 420).

To each of at least one and up to four samples tubes, each containing between 5 and 100 μg of reduced and cysteine blocked protein to be labeled, is added 10 μL of trypsin solution. Each sample tube is mixed by vortexing, then spun and incubated at 37° C. for at least 12 hours and up to 16 hours. The sample digest in each sample tube is then spun (step 425).

Hydrolysis of Protein or Peptide Samples

Figure 4B:
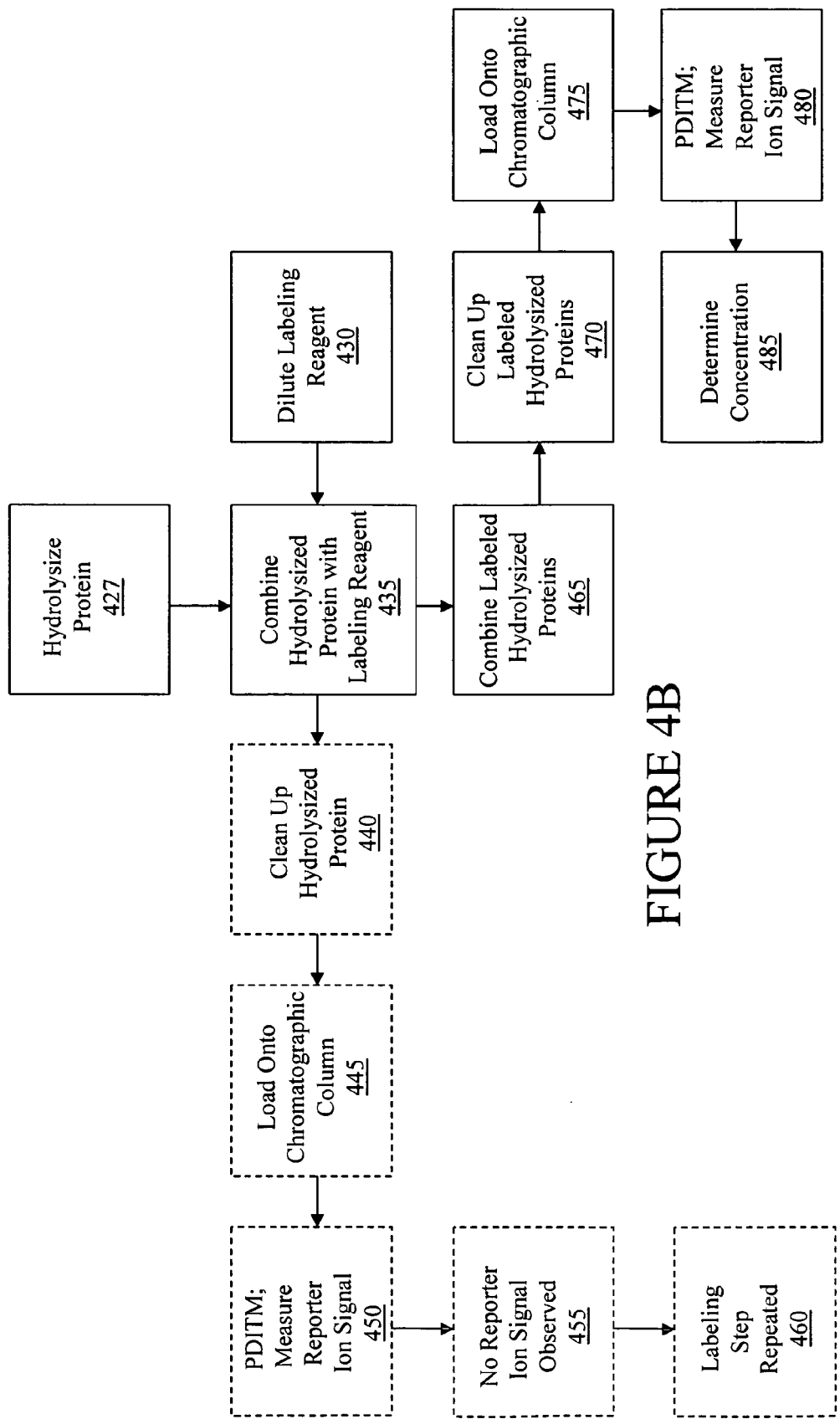

In various embodiments, protein or peptide samples are prepared for analysis by hydrolysis. Accordingly, in various embodiments, a reduction step (e.g., step 410) and a digestion step (e.g., step 420) are not used. Referring to FIG. 4B, in various embodiments, a sample comprising proteins and/or peptides is hydrolysated, e.g., with an acid (step 427). A wide variety of techniques are available in the art for the hydrolysis of proteins and peptides that are suitable for use with the present teachings. Hydrolysis can be conducted, e.g., using strong acid hydrolysis (e.g., by treatment with 6N hydrochloric acid at 100° C. in vacuo) to produce free amino acids. It is to be understood that some hydrolysis conditions can convert some amides (e.g., Asn, Gln) to their acids and decompose other amino acids. Accordingly, in various embodiments, hydrolysis methods other than strong acid hydrolysis can be used.

Labeling Amino Acids with iTRAQ™ Brand Reagents

Referring to FIGS. 4A and 4B, in various embodiments, at least one vial iTRAQ™ brand isobaric reagent, and up to four vials of different iTRAQ™ brand isobaric reagents are warmed to room temperature and to each vial of iTRAQ™ brand isobaric reagent is added 70 μL ethanol, followed by vortexing to mix and spinning (step 430). One vial of iTRAQ™ brand isobaric reagents is used for each sample tube of amino acids from the, e.g., digested protein, hydrolysated protein, etc.

To one sample tube of amino acids, the contents of one vial containing one iTRAQ™ brand isobaric reagent in ethanol is added, followed by vortexing to mix, spinning and incubation for 1 hour at room temperature (step 435). In various embodiments, at least a portion of each of the labeled, amino acids is cleaned up (step 440) (e.g., to remove, e.g., interfering sample, buffer artifacts, etc; by high performance liquid chromatography (HPLC), reverse phase (RP)-HPLC, exchange fractionation, cation exchange, high resolution cation exchange, etc., and combinations thereof) before it is used to measure the reporter ion signal. At least a portion of the cleaned-up, labeled, amino acids is loaded on a chromatographic column (step 445) (e.g., a LC column, a gas chromatography (GC) column, or combinations thereof). At least a portion of the eluent from the chromatographic column is then directed to a mass spectrometry system (step 450) and the amine-containing compound-reporter ion transition signal of one or more amine-containing compounds is measured. In various embodiments, no amine-containing compound-reporter ion transition signal is observed (step 455). In various embodiments, where no amine-containing compound-reporter ion transition signal is observed, for samples of labeled, amino acids, the steps of labeling the amino acids are repeated (step 460).

Combining the iTRAQ™ Brand Reagent-Labeled Amino Acids for Analysis

Referring to FIGS. 4A and 4B, in various embodiments, the entire contents of each labeled, amino acids sample tube is transferred to one fresh sample tube to provide a combined sample, which is vortexed to mix, then spun (step 465). At least a portion of each of the labeled, digested protein is cleaned up (step 470) (e.g., to remove, e.g., interfering sample, buffer artifacts, etc; by high performance liquid chromatography (HPLC), reverse phase (RP)-HPLC, exchange fractionation, cation exchange, high-resolution cation exchange, etc., and combinations thereof) before it is used to measure the reporter ion signal (step 475). At least a portion of the cleaned-up, labeled, amino acids sample is loaded on a chromatographic column (e.g., a LC column, a gas chromatography (GC) column, or combinations thereof). At least a portion of the eluent from the chromatographic column is then directed to a mass spectrometry system (step 480) and the amine-containing compound-reporter ion transition signal of one or more amine-containing compounds is measured using PDITM (e.g., MRM). The concentration (e.g., relative, absolute, or both) of one or more of the amine-containing compounds of interest in the combined sample is then determined (step 485).

Example 3

Combining with a Standard Compound

Figure 5:
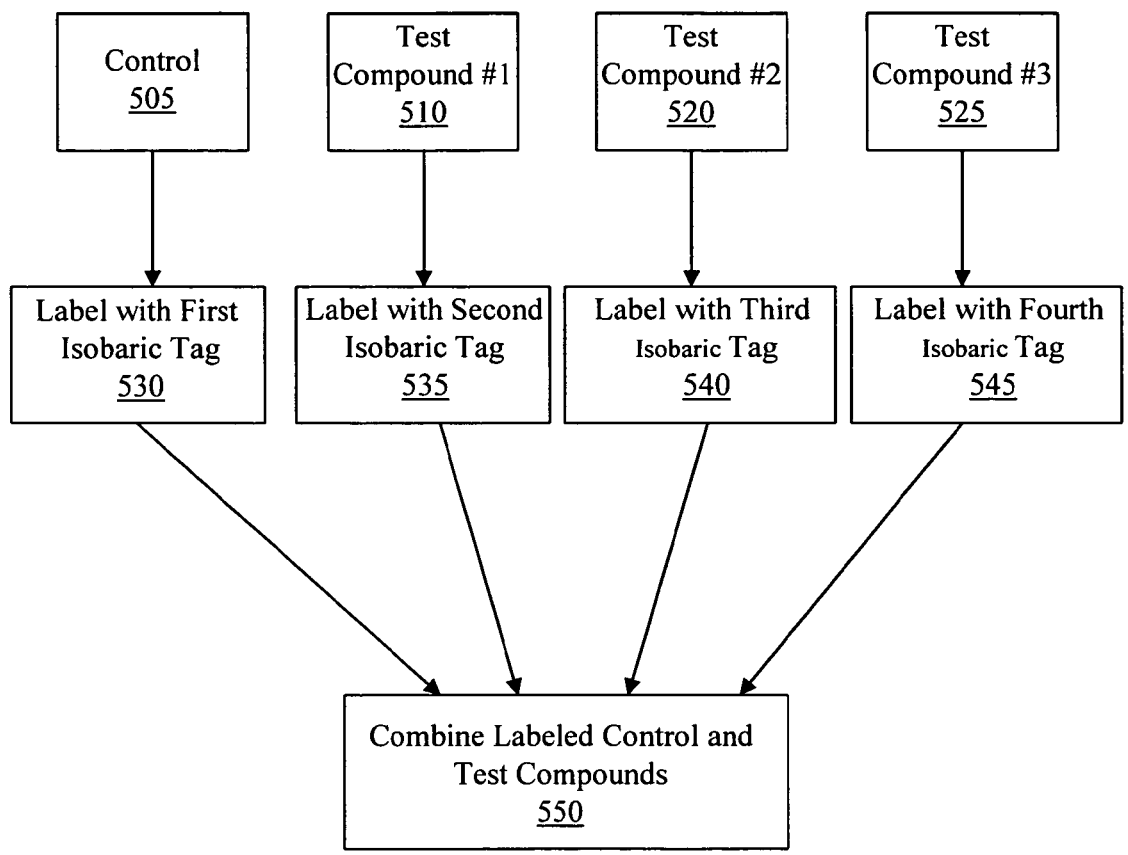
FIG. 5 is a schematic diagram of various embodiments of using a standard compound in a combined sample.

Referring to FIG. 5, in various embodiments, the determination of the concentration of one or more amine-containing compounds in one or more samples can proceed with providing one or more amine-containing compounds, including, but not limited to peptides, polypeptides, proteins, amino acids, nitrofuran metabolites, polyamines and catecholamines. In various embodiments, an isobarically labeled standard compound (step 505) (e.g., an amine-containing compound of interest from a control sample, an amine-containing compound of interest from a sample of known concentration, etc.) is used as an internal standard (e.g., combined with) two or more isobarically labeled amine-containing test compounds to be analyzed, e.g., test compound #1 (step 510), test compound #2 (step 520), and test compound #3 (step 525).

In various embodiments, two or more of the amine containing compounds to be analyzed comprise the same amine-containing compound of interest. For example, test compound #1, test compound #2, and test compound #3 can comprise the same amine-containing compound of interest (e.g., a lysine) but, e.g., from three different samples (e.g., time point 1, time point 2, time point 3, etc., e.g., to monitor the progression of some process, e.g., disease, fermentation, etc.), the same sample (e.g., to provide a triplicate analysis, in one experimental run, of the sample), or combinations thereof.

The determination of the concentration of one or more of the amine-containing compounds can proceed with labeling the standard compound and each of the amine-containing test compounds with a different isobaric tag from a set of isobaric tags (e.g, iTRAQ™ brand reagents). For example, the standard compound can be labeled with a first isobaric tag from the set of isobaric tags (step 530), test compound #1 labeled with a second isobaric tag from the set of isobaric tags (step 535), test compound #2 labeled with a third isobaric tag from the set of isobaric tags (step 540), and test compound #3 with a fourth isobaric tag from the set of isobaric tags (step 545).

In various embodiments, at least a portion of an isobarically labeled standard compound and portions of the isobarically labeled test compounds are combined (step 550) to produce a combined sample and at least a portion of the combined sample is subjected to PDITM.

In various embodiments, the addition of an isobarically labeled standard compound can serve as an internal standard for one or more amine-containing compounds of interest in the combined sample. In various embodiments, a different isobarically labeled standard compound is added for each different amine-containing compound of interest in the combined sample, each different isobarically labeled standard compound, for example, serving as an internal standard for a different amine-containing compound of interest.

Example 4

Multiple Determination of Amine-Containing Compound Concentrations

The following example illustrates the multiplex determination of the concentration of four polyamines using isobaric tags from a set of iTRAQ™ brand reagents. The teachings of this example are not exhaustive, and are not intended to limit the scope of these experiments or the present teachings.
Materials and Methods:

The spectra of this example were obtained using an API 2000 triple quadrupole LC/MS/NIS system for the spectra of FIGS. 6B through 10D and an API 2000 triple quadrupole instrument coupled to an HPLC system equipped with an HILC column. for the spectra of FIGS. 11 through 13. The chromatographic set-up comprised a binary gradient HPLC system equipped with an autosampler, 150×2.1 mm C18 reverse phase column and column heater. Amine-containing compounds were prepared by dissolving them in methanol and then reacting them with iTRAQ reagents using standards labeling protocol. Standard amines were obtained from Fluka.
Spectra:

Example 4 illustrates a determination of the concentration of multiple amine-containing compounds using a combined sample. FIGS. 6A-10D depict mass spectra of the individual amine-containing compounds, both unlabeled and labeled with an isobaric tag from a set of isobaric tags. In this example, the isobaric tags were iTRAQ™ brand reagents. FIGS. 11 and 13 depict a chromatogram for the combined sample. The amine-containing compounds of interest in the combined sample in this example were 1,4 diaminobutane (putrescene), 1,5 diaminopentane (cadaverine), $N^1$-(3-aminopropyl)-butane-1,4-diamine (spermidine) and 1,7 diaminoheptane. FIGS. 12A-12C depict chromatograms, respectively, for 1,4 diaminobutane (putrescene), 1,5 diaminopentane (cadaverine), and 1,7 diaminoheptane.

Referring to FIGS. 6A-6C, mass spectra of putrescene both unlabeled 602 and labeled at the primary amines with isobaric tag 604 were obtained. In this example, the 114 isobaric tag Q114 from the set of iTRAQ brand reagent isobaric tags was used to label the primary amines of putrescene. FIG. 6B depicts an ESI-TOF mass spectrum of putrescene labeled with isobaric tag Q114 from the set of iTRAQ brand reagent isobaric tags. The main peak observed 635 corresponded to labeled putrescene (m/z about 377), although minor peaks corresponding to a labeled putrascene-sodium adduct 640 (m/z about 399) and to low mass impurities present in the solvent 630 (m/z about 375), 610 (m/z about 245), and a a cluster of peaks 615, 620, 625 (between m/z of about 319 to 321) were also observed.

FIG. 6C depicts an ESI TOF-TOF mass spectrum of labeled putrescene subjected to CD. The main peak observed 650 corresponded to the reporter ion of the 114 isobaric tag, although peaks corresponding to labeled putrescene (m/z about 377), 670 and to a putrescene structure specific fragment 660 (m/z of about 233) were also observed.

Referring to FIGS. 7A-7C, mass spectra of cadaverine both unlabeled 702 and labeled at the primary amines with isobaric tag 704 were obtained. In this example, the 115 isobaric tag Q115 from the set of iTRAQ™ brand reagents isobaric tags was used to label the primary amines of cadaverine. FIG. 7B depicts an ESI-TOF mass spectrum of cadaverine labeled with isobaric tag Q115 from the set of iTRAQ™ brand reagent isobaric tags. The peak observed at 730 corresponded to the labeled cadaverine (m/z about 391), although peaks corresponding to background from solvent 710 (m/z about 102) and 725 (m/z about 248), and to iTRAQ™ reaction side product 715 (m/z about 163) and 720 (m/z about 191) were also observed.

FIG. 7C depicts an ESI TOF-TOF mass spectrum of labeled cadaverine subjected to CID. The main peak observed 740 corresponded to the reporter ion of the 115 isobaric tag, although peaks corresponding to labeled cadaverine 760 (m/z about 391) and to a cadaverine structure specific fragment 750 (m/z about 247) were also observed.

Referring to FIG. 8A-8C, mass spectra of 1,7-diaminoheptane both unlabeled 802 and labeled at the primary amines with isobaric tag 804 were obtained. In this example, the 116 isobaric tag Q116 from the set of iTRAQ™ brand reagents isobaric tags was used to label the primary amines of 1,7-diaminoheptane. FIG. 8B depicts and ESI-TOF mass spectrum of 1,2-diaminoheptane labeled with isobaric tag Q116 from the set of iTRAQ™ brand reagent isobaric tags. The peak observed 825 corresponded to the labeled 1,7-diaminoheptane (m/z about 419), although peaks corresponding to solvent background 810 (m/z about 102) and to iTRAQ™ reaction by-products 815 (m/z about 163) and 820 (m/z about 191) were also observed.

FIG. 8C depicts an ESI TOF-TOF mass spectrum of labeled 1,7-diaminoheptane subjected to OD. The main peak observed 830 corresponded to the reporter ion of the 116 isobaric tag, although peaks corresponding to the labeled 1,7-diaminoheptane 850 (m/z about 419) and to a structure specific fragment 840 (m/z about 275) were also observed.

Referring to FIGS. 9A-9D, mass spectra of spermidine both unlabeled 902 and labeled at the primary amines with isobaric tag 904 were obtained. In this example, the 114 isobaric tag Q114 from the set of iTRAQ™ brand reagent isobaric tags was used to label the primary amines of spermidine. FIG. 9B depicts an ESI-TOF mass spectrum of spermidine labeled with isobaric tag Q114 from the set of iTRAQ™ brand reagent isobaric tags. The peak observed 925 corresponded to labeled spermidine (m/z about 434), although peaks corresponding to iTRAQ™ reaction by-products 908 (m/z about 163), 916 (m/z about 217), 918 (m/z about 245), 930 (m/z about 458) and to partially labeled secondary amine 935 (m/z about 578) were also observed.

FIG. 9C depicts an ESI TOF-TOF mass spectrum of labeled spermidine subjected to CD. The peak observed 945 corresponded to the reporter ion of the 114 isobaric tag, although peaks corresponding the labeled spermidine 980 (m/z about 434), to structure specific fragments 940 (m/z about 97), 955 (m/z about 202) and 970 (m/z about 290), to an iTRAQ™ label 950 (m/z about 145), and to a solvent structure fragment 960 (m/z about 216) were also observed.

FIG. 9D depicts an ESI TOF-TOF mass spectrum of labeled spermidine subjected to CID. The peak observed 985 corresponded to the reporter ion of the 114 isobaric tag, although peaks corresponding to the labeled spermidine 995 (m/z about 434) and to a secondary labeled amine 990 (m/z about 578) were also observed.

Referring to FIGS. 10A-10D, mass spectra of spermine both unlabeled 1002 and labeled at the primary amines with isobaric tag 1004 were obtained. In this example, the 117 isobaric tag Q117 from the set of iTRAQ™ brand reagent isobaric tags was used to label the primary amines of spermine. FIG. 10B depicts and ESI-TOF mass spectrum of spermine labeled with isobaric tag Q117 from the set of iTRAQ™ brand reagent isobaric tags. The peak observed 1035 corresponded to the labeled spermine (m/z about 491), although peaks corresponding to solvent background 1008 (m/z about 177), 1020 (m/z about 248) and 1022 (m/z about 185), to iTRAQ™ reaction by-products 1010 (m/z about 185), and 1012 (m/z about 191), to spermidine labeled with isobaric tag Q114 from the set of iTRAQ™ brand reagent isobaric tags 1030 (m/z about 434), to impurities in the standard spermidine 1040 (m/z about 535), 1045 (m/z about 738), and 1050 (m/z about 754) were also observed.

FIG. 10C depicts an ESI TOF-TOF mass spectrum of labeled spermine subjected to CID. The peak observed 1060 corresponded to the reporter ion of the 117 isobaric tag, although peaks corresponding to labeled spermine 1075 (m/z about 491), to structure specific fragments 1055 (m/z about 100), 1058 (m/z about 202), and 1070 (m/z about 273) were also observed.

FIG. 10D depicts an ESI TOF-TOF mass spectrum of labeled spermine subjected to CID. The peak observed 1080 corresponded to the reporter ion of the 117 isobaric tag, although peaks corresponding to labeled spermine 1090 (m/z about 491), to a structure specific fragment, with label on primary amine 1082 (m/z about 202), to a structure specific fragment 1085 (m/z about 273), and to an intact amine with all amines labeled 1095 (m/z about 635) were also observed.

FIG. 11 depicts chromatograms for a combined sample, depicting a chromatogram for 1,4 diaminobutane (putrescene) 1120, 1,5 diaminopentane (cadaverine) 1110, and 1,7 diaminoheptane 1105 analyzed in MRM mode on an API 2000 triple quadrupole instrument coupled to an HPLC system equipped with an HILC column.

Referring to FIGS. 12A-C, chromatograms of putrescene, cadaverine and 1,7-diaminoheptane labeled at the primary amines with an isobaric tag were obtained. FIG. 12A depicts an extracted ion chromatogram of putrescene labeled with 114 isobaric tag Q114 from the set of iTRAQ™ brand reagent isobaric tags obtained from the LC/MS/MS run shown in FIG. 11. The peak observed 1205 corresponded to the labeled putrescene (retention time about 8.9 minutes). FIG. 12B depicts an extracted ion chromatogram of cadaverine labeled with 115 isobaric tag Q115 from the set of iTRAQ™ brand reagent isobaric tags obtained from the LC/MS/MS run shown in FIG. 11. The peak observed 1215 corresponded to the labeled cadaverine (retention time about 8.8 minutes). FIG. 12C depicts an extracted ion chromatogram of 1,7-diaminoheptane labeled with 116 isobaric tag Q116 from the set of iTRAQ™ brand reagent isobaric tags obtained from the LC/MS/MS run shown in FIG. 11. The peak observed 1225 corresponded to the labeled 1,7-diaminoheptane (retention time about 8.4 minutes).

FIG. 13 depicts chromatograms for a combined sample, depicting the chromatogram for 1,7-diaminoheptane 1305, cadaverine 1310, and putrescene 1320.

Referring to FIGS. 14A-C, background O-MALDI mass spectra of 95% acetonitrile with matrix cyano-4-hydroxy cinnamic acid were obtained. Most of the ions seen in the 3 mass ranges of the same spectra arise from chemical background from the solvents and matrix ions from 4-hydroxycinnamic acid.

FIG. 15 depicts a O-MALDI-TOF mass spectrum of a mixture of putrescene, cadaverine and 1,7-diaminoheptane labeled at the primary amines with an isobaric tag in 95% acetonitrile (ACN) and cyano-4-hydroxy cinnamic acid (CHCA). The peaks observed corresponded to labeled putrescene 1512 (m/z about 379), labeled cadaverine 1520 (m/z about 391), labeled 1,7-diaminoheptane 1525 (m/z about 419) and labeled spermidine 1530 (m/z about 434), although peaks corresponding to chemical impurities in the standard 1502 (m/z about 359), 1504 (m/z about 361), 1508 (m/z about 377), and 1515 (m/z about 380) were also observed.

Referring to FIGS. 16A and 16B, a mass spectrum of putrescene both unlabeled 1602 and labeled at the primary amines with isobaric tag 1604 was obtained. In this example, the 114 isobaric tag Q114 from the set of iTRAQ brand reagent isobaric tags was used to label the primary amines of putrescene. FIG. 16B depicts an O-MALDI-TOF mass spectrum of labeled putrescene in matrix 4-hydroxycinnamic acid subjected to CID. The main peak observed 1608 corresponded to the reporter ion of the 114 isobaric tag, although peaks corresponding to labeled putrescene 1640 (m/z about 377), to an intact label 1610 (m/z about 145), to structure specific fragments 1615 (m/z about 172), 1620 (m/z about 233), 1630 (m/z about 331), and 1635 (m/z about 359) were also observed.

Referring to FIGS. 17A and 17B, a mass spectrum of cadaverine both unlabeled 1702 and labeled at the primary amines with isobaric tag 1704 was obtained. In this example, the 115 isobaric tag Q115 from the set of iTRAQ™ brand reagents isobaric tags was used to label the primary amines of cadaverine. FIG. 17B depicts an O-MALDI-TOF mass spectrum of cadaverine labeled with isobaric tag Q115 from the set of iTRAQ™ brand reagent isobaric tags in matrix 4-hydroxycinnamic acid. The main peak observed 1708 corresponded to the reporter ion of the 115 isobaric tag, although peaks corresponding to labeled cadaverine 1730 (m/z about 391), to an intact label 1712 (m/z about 145), and to a structure specific fragment 1720 (m/z about 247) were also observed.

Referring to FIGS. 18A and 18B, a mass spectrum of 1,7-diaminoheptane both unlabeled 1802 and labeled at the primary amines with isobaric tag 1804 was obtained. In this example, the 116 isobaric tag Q116 from the set of iTRAQ™ brand reagents isobaric tags was used to label the primary amines of cadaverine. FIG. 18B depicts an O-MALDI-TOF mass spectrum of 1,7-diaminoheptane labeled with isobaric tag Q116 from the set of iTRAQ™ brand reagent isobaric tags in matrix 4-hydroxycinnamic acid. The main peak observed 1815 corresponded to the reporter ion of the 116 isobaric tag, although peaks corresponding to labeled 1,7-diaminoheptane 1845 (m/z about 419), to an iTRAQ™ label fragment 1810 (m/z about 101), and to structure specific fragments 1825 (m/z about 275) and 1835 (m/z about 381) were also observed.

Referring to FIGS. 19A and 19B, a mass spectrum of spermidine both unlabeled 1902 and labeled at the primary amines with isobaric tag 1904 was obtained. In this example, the 114 isobaric tag Q114 from the set of iTRAQ™ brand reagents isobaric tags was used to label the primary amines of spermidine. FIG. 19B depicts an O-MALDI-TOF mass spectrum of spermidine labeled with isobaric tag Q114 from the set of iTRAQ™ brand reagent isobaric tags in matrix 4-hydroxycinnamic acid. The main peak observed 1908 corresponded to the reporter ion of the 114 isobaric tag, although peaks corresponding to labeled spermidine 1965 (m/z about 434), to an intact iTRAQ™ label 1912 (m/z about 145) and to structure specific fragments 1915 (m/z about 156), 1918 (m/z about 175), 1925 (m/z about 184), 1930 (m/z about 202), 1935 (m/z about 220), 1940 (m/z about 273), 1945 (m/z about 290), and 1960 (m/z about 414) were also obtained.

Referring to FIGS. 20A and 20B, a mass spectrum of spermine both unlabeled 2002 and labeled at the primary amines with isobaric tag 2004 was obtained. In this example, the 117 isobaric tag Q117 from the set of iTRAQ™ brand reagents isobaric tags was used to label the primary amines of spermidine. FIG. 20B depicts an O-MALDI-TOF mass spectrum of spermine labeled with isobaric tag Q117 from the set of iTRAQ™ brand reagent isobaric tags in 95% acetonitrile and CHCA. The main peak observed 2015 corresponded to labeled spermine (m/z about 491), although peaks corresponding to structure specific fragments 2008 (m/z about 379) and 2030 (m/z about 535) were also observed.

Referring to FIGS. 21A-C, mass spectra of spermine both unlabeled 2102 and labeled at the primary amines with isobaric tag 2104 were obtained. In this example, the 117 isobaric tag Q117 from the set of iTRAQ™ brand reagent isobaric tags was used to label the primary amines of spermine. FIG. 21B depicts an O-MALDI-TOF mass spectrum of spermine labeled with isobaric tag Q117 from the set of iTRAQ™ brand reagent isobaric tags in 4-hydroxycinnamic acid matrix. The peak observed 2110 corresponded to the reporter ion of the 117 isobaric tag, although peaks corresponding to labeled spermine 2140 (m/z about 491) and to structure specific fragments 2120 (m/z about 202), 2130 (m/z about 275), and 2135 (m/z about 473) were also observed.

FIG. 21C depicts an O-MALDI-TOF mass spectrum of spermine labeled with isobaric tag Q117 from the set of iTRAQ™ brand reagent isobaric tags in 4-hydroxycinnamic acid matrix. The peak observed 2150 corresponded to the reporter ion of the 117 isobaric tag, although peaks corresponding to labeled spermine 2180 (m/z about 491) and to structure specific fragments 2160 (m/z about 202) and 2170 (m/z about 275) were also observed.

Referring to FIGS. 22A and 22B, a mass spectrum of spermine both unlabeled 2202 and labeled at the primary amines with isobaric tag 2204 was obtained. In this example, the 117 isobaric tag Q117 from the set of iTRAQ™ brand reagent isobaric tags was used to label the primary amines of spermine. FIG. 22B depicts an O-MALDI-TOF mass spectrum of spermine labeled with isobaric tag Q117 from the set of iTRAQ™ brand reagent isobaric tags in 4-hydroxycinnamic acid matrix. The main peak observed 2210 corresponded to the reporter ion of the 117 isobaric tag, although peaks corresponding to labeled spermine 2250 (m/z about 491), to structure specific fragments 2220 (m/z about 202), 2230 (m/z about 271) and 2235 (m/z about 273), and to the precursor ion selected for fragmentation 2260 (m/z about 635) were also observed.

FIG. 23 depicts a chromatogram of an MRM analysis of iTRAQ™ 115-labeled amino acid standards, containing amino acids seen in protein hydrolysates for different amino acids: 2310, 2320, 2330, 2340, 2350, and 2360.

Example 5

Bovin Serum Albumin (BSA) Sample

The following example illustrates the determination of the concentration of amino acids of a protein sample subjected to hydrolysis to produce free amino acids. The teachings of this example are not exhaustive, and are not intended to limit the scope of these experiments or the present teachings.

Materials and Methods:

Protein or peptide hydrolysates are prepared by a standard hydrolysis methods. Specifically, a Bovine Serum Sample of comprising 1 ug was hydrolyzed with 6 N HCl at 110° C. for 17 hours. The hydrolyzed sample is then mixed with buffer, isopropanol and an iTRAQ brand reagent and allowed to react at room temperature. The sample is then dried and redissolved or directly diluted to the desired concentration for analysis (typically 0.2 µg of peptide or protein is required for each analysis). Standards (i.e. norleucine, norvaline) can be added to the samples before hydrolysis and/or labeling to follow the recovery of sample through the experimental procedure. Details on sample labeling are also provided in Table 2 in a protocol format.

For multiple samples (up to 4 or up to 3 if including an internal standard), prepare each sample as above and label with different iTRAQ Reagents (114, 115, 116, or 117). After the labeling reaction mix the samples labeled with the different reagents together. The same process is performed for an amine or amino acid standard mix in a separate vial but with a different tagging reagent and an external calibration curve can be generated using the labeled standards. The labeled standards can also be mixed with the sample, providing an internal standard for each amine or amino acid (see FIG. 1). HPLC separation is performed using a C18 column (fully end capped with 15% carbon loading) heated to 50° C. with a flow rate of 1 ml/min with a 200 µL/min split to the detector. The gradient, wash, and equilibration take a total of 20 min.

Quantitation of amino acids concentration is done using HPLC separation followed by ESI MRM analysis on either triple quadrupole or Q TRAP MS/MS system operated in MRM mode. For MRM analysis, MRM transitions are made up of the labeled mass of the amino acid and the reporter ion fragment generated for the particular reagent used in the MS/MS, e.g. for 117 reagent, glycine is monitored using a transition of 220.1>117.1. MRM transitions for all the amino acids that need to be monitored are entered in the method. One of the transitions is normally reserved for internal standards spiked in the sample. Internal standard for every amino acid correct for any variations in the detection response as well as chromatographic separation. Quantitation is performed using Analyst™ software and a tool specifically designed to support amino acid analysis.

TABLE 2

| Step | Process |
|---|---|
| 1. | To each amino acid sample containing a total of 10 nmole of amino acid or about 1 µg of peptide or protein hydrolysate add 5 µL of Dissolution Buffer (1 M borate buffer,pH 8.5). |
| 2. | Add 3 µL of isopropanol to each tube and vortex to mix, then spin. |
| 3. | Allow each vial of iTRAQ ™ Reagent 117 required to reach room temperature (each vial will label 15-20 samples). |
| 4. | Spin to bring the solution to the bottom of the tube. |
| 5. | Add 1 µL of iTRAQ ™ Reagent 117 to each sample tube and vortex to mix, then spin. |
| 6. | Incubate the tubes at room temperature for 1 hour. |
| 7. | Add 1 µL of 6% hydroxylamine to each tube and vortex to mix, then spin. |
| 8. | Dry the samples in a centrifugal vacuum concentrator. |
| 9. | Store the dry samples at −15 to −25° C. if you are not going to analyze them immediately. |

Further details on sample handling and LC/MS/MS settings for generation of the data of this example are as follows. Prior to loading on the LC column, each sample was reconstituted with 25 µL of 3% formic acid containing 6 pmole/µL of amino acid standard labeled with iTRAQ reagent 114. A volume of 5 µL was then injected into an Applied Biosystems/MDS Sciex API 2000 LC/MS/MS instrument using manufacturer recommended procedures. Details on the instruments operating conditions are presented in Tables 3-11. Tables 3 and 4 providing conditions related to the LC portion of the instrument and Tables 5-11 providing conditions related to the MS/MS portion of the instrument.

TABLE 3

LC Conditions

Devices:

| | |
|---|---|
| AutoSampler | Agilent 1100 G1313A |
| Pump | Agilent 1100 G1312A |

Agilent 1100 Autosampler Properties

| | |
|---|---|
| Autosampler Model: | Agilent 1100 Autosampler |
| Syringe Size (μl): | 100 |
| Injection Volume (μl): | 5.00 |
| Draw Speed (μl/min): | 200.0 |
| Eject Speed (μl/min): | 200.0 |

Agilent 1100 LC Pump Method Properties

| | |
|---|---|
| Pump Model: | Agilent 1100 LC Binary Pump |
| Minimum Pressure (psi): | 0.0 |
| Maximum Pressure (psi): | 3000.0 |
| Dead Volume (μl): | 40.0 |
| Maximum Flow Ramp (ml/min$^2$): | 1.0 |
| Maximum Pressure Ramp (psi/sec): | 290.0 |
| Left Compressibility: | 50.0 |
| Right Compressibility: | 115.0 |
| Left Dead Volume (μl): | 40.0 |
| Right Dead Volume (μl): | 40.0 |
| Left Stroke Volume (μl): | −1.0 |
| Right Stroke Volume (μl): | −1.0 |
| Left Solvent: | A2 |
| Right Solvent: | B2 |
| Column: | |

Higgins Analytical, PHALANX C18, 5 um, 150 × 4.6 mm
Column Temperature (° C.): 50.00
Mobile Phases:

Solvent A: 0.1% Formic acid, 0.005% Heptafluorobutyric acid in water
Solvent B: 0.1% Formic acid, 0.005% Heptafluorobutyric acid in acetonitrile
Heptafluorobutyric acid is added as an ion-pairing reagent to increase the resolution of the separation.

TABLE 4

LC GRADIENT

| Step | Total Time (min) | Flow Rate (μL/min) | Solvent A (%) | Solvent B (%) |
|---|---|---|---|---|
| 0 | 0.00 | 1000 | 98.0 | 2.0 |
| 1 | 10.00 | 1000 | 72.0 | 28.0 |
| 2 | 10.10 | 1000 | 0.0 | 100.0 |
| 3 | 16.00 | 1000 | 0.0 | 100.0 |
| 4 | 16.10 | 1000 | 98.0 | 2.0 |
| 5 | 25.00 | 1000 | 98.0 | 2.0 |

In the present example, multiple periods (periods 1-3) are used in the MS/MS data acquisition so that all transitions are not scanned continuously during the run. Only those transitions in a period are scanned during that period. This can allow for more data points per peak which results in better quantitation.

TABLE 5

MS/MS ANALYSIS CONDITIONS

Devices:

| | |
|---|---|
| Mass Spectrometer: | QTrap (API2000) |

Acquisition Info:

| | |
|---|---|
| Sample Acq Duration: | 25 min 7 sec |
| Number of Scans: | 1691 |
| Periods in File: | 3 |
| Software Version: | Analyst 1.4.1 |

Quantitation Info:

| | |
|---|---|
| Dilution Factor: | 1.000000 |

TABLE 6

PERIOD 1: TRANSMITTED MASS PARAMETER TABLE

| Amino Acid | Q1 Mass (amu) | Q3 Mass (amu) |
|---|---|---|
| Cya | 314.10 | 114.00 |
|  | 314.10 | 117.00 |
| Asn | 277.20 | 114.00 |
|  | 277.20 | 117.00 |
| Gln | 291.20 | 114.00 |
|  | 291.20 | 117.00 |
| Ser | 250.20 | 114.00 |
|  | 250.20 | 117.00 |
| Gly | 220.10 | 114.00 |
|  | 220.10 | 117.00 |
| His | 300.20 | 114.00 |
|  | 300.20 | 117.00 |
| Asp | 278.10 | 114.00 |
|  | 278.10 | 117.00 |
| Thr | 264.20 | 114.00 |
|  | 264.20 | 117.00 |
| Ala | 234.20 | 114.00 |
|  | 234.20 | 117.00 |
| Glu | 292.20 | 114.00 |
|  | 292.20 | 117.00 |
| Arg | 319.20 | 114.00 |
|  | 319.20 | 117.00 |
| MetS | 310.20 | 114.00 |
|  | 310.20 | 117.00 |

TABLE 7

PERIOD 1: PARAMETERS

| Parameter | Value |
|---|---|
| Scans in Period: | 285 |
| Relative Start Time: | 0.00 msec |
| Experiments in Period: | 1 |
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thres.: | 0.00 cps |
| Settling Time: | 0.0000 msec |
| MR Pause: | 5.0070 msec |
| MCA: | No |
| Step Size: | 0.00 amu |

TABLE 8

PERIOD 2: TRANSMITTED MASS PARAMETER TABLE

| Amino Acid | Q1 Mass (amu) | Q3 Mass (amu) |
|---|---|---|
| Pro | 260.20 | 114.00 |
|  | 260.20 | 117.00 |
| Cys | 266.10 | 114.00 |
|  | 266.10 | 117.00 |
| Lys | 435.30 | 114.00 |
|  | 435.30 | 117.00 |

TABLE 9

PERIOD 2: PARAMETERS

| Parameter | Value |
|---|---|
| Scans in Period: | 115 |
| Relative Start Time: | 5.75 min |
| Experiments in Period: | 1 |
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thres.: | 0.00 cps |
| Settling Time: | 0.0000 msec |
| MR Pause: | 5.0070 msec |
| MCA: | No |
| Step Size: | 0.00 amu |

TABLE 10

PERIOD 3: TRANSMITTED MASS PARAMETER TABLE

| Amino Acid | Q1 Mass (amu) | Q3 Mass (amu) |
|---|---|---|
| Val, Nva | 262.20 | 114.00 |
|  | 262.20 | 117.00 |
| Met | 294.20 | 114.00 |
|  | 294.20 | 117.00 |
| Tyr | 326.20 | 114.00 |
|  | 326.20 | 117.00 |
| Ile, Leu, Nle | 276.20 | 114.00 |
|  | 276.20 | 117.00 |
| Phe | 310.20 | 114.00 |
|  | 310.20 | 117.00 |
| Trp | 349.20 | 114.00 |
|  | 349.20 | 117.00 |

TABLE 11

PERIOD 3: PARAMETERS

| Parameter | Value |
|---|---|
| Scans in Period: | 1291 |
| Relative Start Time: | 7.36 min |
| Experiments in Period: | 1 |
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thres.: | 0.00 cps |
| Settling Time: | 0.0000 msec |
| MR Pause: | 5.0070 msec |
| MCA: | No |
| Step Size: | 0.00 amu |

Spectra and Results:

In the present example, the concentrations of 20 amino acids were determined. Table 12 summarizes the data obtained for each amino acid (listed in column 2). Column 3 lists the retention time of the amino acid on the LC column, column 4 lists the area of the peak associated with the amino acid of the sample of unkown concentration, column 5 lists the area of the peak associated with the amino acid standard sample, column 6 lists the concentration of the amino acid in the standard sample, and column 7 listed the concentration determined for the amino acid in this example using the present teachings. The concentration of an amino acid in the unknown sample was determined by dividing the area of the peak associated with the amino acid of the unknown sample by the area of the peak associated with the standard sample and multiplying this ration by the concentration of the known sample.

Example spectra are presented in FIGS. 24, and 25A-25U.

FIG. 24 depicts a chromatogram of an MRM analysis of iTRAQ™ 114-labeled amino acid standards, and 117-labeled samples. The amino acids corresponding to the various retention times depicted in FIG. 24 are listed in Table 12. FIGS. 25A-25U schematically depict MRM data for various amino acids measured. The right panel in each of FIGS. 25A-25U depicting the ion signal of the internal standard (IS) 114-labeled amino acid, and the left panel the ion signal of the 117-labeled sample. The peaks from which areas where derived have been shaded. It should be noted that for Cya, no sample signal was detected, hence no shaded peak appears in the left panel of FIG. 25A.

FIGS. 26A-B compare the measured concentrations of the amino acids to standard amino acid analysis methods/instrumentation pre and post column derivitization on Beckman. The results show close agreement with these methods.

FIGS. 26A and 26B compare results for a representative protein hydrolysate sample against theory and a Beckman Gold system. The FIG. 26A compares the theoretical mole percent of each amino acid (far left bar for a given amino acid) with the mole percents determined on a Beckman Gold system (middle bar for a given amino acid) and those measured in this example using LC/MS/MS (far right bar for a given amino acid). FIG. 26B compares the variation from the theory for the protein hydrolysate sample run on the a Beckman Gold system (left bar for a given amino acid) and those measured in this example using LC/MS/MS (right bar for a given amino acid). The tyrosine value from the present example (LC/MS/MS system) is low since the sample was not treated with hydroxylamine (hydroxyamine can remove unwanted second iTRAQ reagent label from tyrosine).

TABLE 12

| # | Amino Acid | RT (min) | Area | IS Area | IS Concentration (pmol) | Calculated. Concentration (pmol) |
|---|---|---|---|---|---|---|
| 1. | Cya | 0.00 | 0.00e+00 | 6.01e+03 | 30.00 | 0.0 |
| 2. | Ser | 2.79 | 1.38e+05 | 5.47e+04 | 30.00 | 71.7 |
| 3. | Gly | 3.08 | 8.06e+04 | 4.42e+04 | 30.00 | 52.0 |
| 4. | His | 3.05 | 3.46e+04 | 2.28e+04 | 30.00 | 43.3 |
| 5. | Asp | 3.36 | 2.38e+05 | 4.65e+04 | 30.00 | 145.6 |
| 6. | MOx | 3.43 | 2.27e+03 | 3.60e+03 | 30.00 | 17.9 |
| 7. | Thr | 3.98 | 1.76e+05 | 5.88e+04 | 30.00 | 85.0 |
| 8. | Ala | 4.51 | 3.01e+05 | 6.58e+04 | 30.00 | 130.4 |
| 9. | Glu | 4.31 | 4.25e+05 | 5.51e+04 | 30.00 | 219.8 |
| 10. | Arg | 4.18 | 9.24e+04 | 3.83e+04 | 30.00 | 68.8 |
| 11. | Pro | 5.67 | 2.67e+05 | 9.17e+04 | 30.00 | 82.8 |
| 12. | Cys | 6.15 | 5.55e+03 | 7.01e+03 | 30.00 | 22.6 |
| 13. | Lys | 6.33 | 8.91e+04 | 1.44e+04 | 30.00 | 167.7 |

TABLE 12-continued

| # Amino Acid | RT (min) | Area | IS Area | IS Concentration (pmol) | Calculated. Concentration (pmol) |
|---|---|---|---|---|---|
| 14. Val | 7.59 | 3.63e+05 | 9.99e+04 | 30.00 | 103.6 |
| 15. Nva | 7.91 | 1.05e+05 | 9.75e+04 | 30.00 | 30.6 |
| 16. Met | 7.68 | 2.79e+04 | 6.69e+04 | 30.00 | 11.9 |
| 17. Tyr | 8.09 | 1.48e+05 | 7.89e+04 | 30.00 | 53.5 |
| 18. Ile | 9.05 | 2.01e+05 | 1.40e+05 | 30.00 | 41.0 |
| 19. Leu | 9.31 | 8.37e+05 | 1.39e+05 | 30.00 | 171.4 |
| 20. Nle | 0.00 | 0.00e+00 | 1.34e+05 | 30.00 | 0.0 |
| 21. Phe | 9.67 | 3.35e+05 | 1.18e+05 | 30.00 | 81.0 |

Example 6

Biological Fluid Sample

The following example illustrates the determination of the concentration of free amino acids in a biological sample. Although the data of this example is on a plasma sample, the teachings of the present example can be applied to other biological fluids, including, but not limited to, urine. The teachings of this example are not exhaustive, and are not intended to limit the scope of these experiments or the present teachings. In the present example, 48 free amino acids in the plasma samples were monitored. The monitored amino acids are listed in Table 13.

TABLE 13

β-alanine
L-alanine
L-α-aminoadipic acid
L-α-amino-n-butyric acid
γ-amino-n-butyric acid
D,L-β-aminoisobutyric acid
L-anserine
L-arginine
L-asparagine
L-aspartic acid
L-carnosine
L-citrulline
creatinine
cystathionine
L-cystine
ethanolamine
L-glutamic acid
L-glutamine
glycine
L-histidine
L-homocystine
δ-hydroxylysine
hydroxy-L-proline
L-isoleucine
L-leucine
L-lysine
L-methionine
L-methionine sulfoxide
1-methyl-L-histidine
3-methyl-L-histidine
L-norleucine
L-norvaline
L-Ornithine
L-phenylalanine
O-phospho-L-serine
O-phosphoethanolamine
L-proline
sarcosine
L-serine
taurine

TABLE 13-continued

L-threonine
L-tryptophan
L-tyrosine
urea
L-valine

The monitoring of one or more free amino acids in blood plasma has several practical applications including, e.g., the detection and/or monitoring of diseases in newborns, detection of biomarkers, etc. For example, certain free amino acids in newborn can be indicative neonatal metabolic diseases, such as, e.g., methylmalonic academia, and propionic academia. Examples of elevated amino acids associated with certain common aminoacidopathies are also listed in Table 14.

TABLE 14

| Aminoacidopathies | Elevated Amino Acid |
|---|---|
| Primary | |
| Arginase deficiency | Arginine, glutamine |
| Arginosuccinase deficiency | Argininosuccinate, glutamine |
| Citrullinemia | Citrulline, glutamine |
| Cystinuria | Cystine, ornithine, lysine, arginine (urine only) |
| Homocystinuria | Homocystine |
| Maple Syrup Urine Disease (MSUD) | Valine, isoleucine, leucine, alloisoleucine |
| Phenylketonuria (PKU) | Phenylalanine |
| Secondary | |
| Hyperammonemia | Glutamine |
| Lactic acidosis | Alanine |
| Organic aciduria | Glycine |
| Transitory neonatal tyrosinemia | Tyrosine |

Although such metabolic disorders are a rare group of genetic disorders, they can have serious consequences for an affected infant. If left untreated, these disorders can cause irreversible mental retardation (ranging from mild to severe), physical disability, neurological damage and even fatality. Early detection (soon after birth) and an accurate diagnosis are very important for achieving a rapid and favorable treatment.

Materials and Methods:

For biological fluids (e.g., plasma, serum, urine), 1 part of the sample is mixed with 4 parts of isopropanol or ethanol to precipitate most of the proteins in the sample. Buffer is added to the supernatant to maintain a basic pH for the labeling reaction. An iTRAQ brand reagent is then added and allowed to react at room temperature. The sample is then dried and redissolved or directly diluted to the desired concentration for analysis (typically 100 nL of biological fluid is required for each analysis). Details on sample labeling are also provided in Table 15 in a protocol format.

TABLE 15

| Step | Process |
|---|---|
| 1. | Transfer 25 µL of plasma and 100 µL of isopropanol to a tube and vortex to mix for 1 min, then spin for 1 min to pellet precipitate. |
| 2. | Remove 10 µL of the supernatant and transfer to a new tube. |
| 3. | Add 5 µL of Dissolution Buffer (1 M borate buffer, pH 8.5) and vortex to mix, then spin. |
| 4. | Allow each vial of iTRAQ ™ Reagent 114 required to reach room temperature (each vial will label 15-20 samples). |

TABLE 15-continued

| Step | Process |
|---|---|
| 5. | Spin to bring the solution to the bottom of the tube. |
| 6. | Add 1 μL of iTRAQ ™ Reagent 114 to each sample tube and vortex to mix, then spin. |
| 7. | Incubate the tubes at room temperature for 1 hour. |
| 8. | Add 1 μL of 6% hydroxylamine to each tube and vortex to mix, then spin. |
| 9. | Dry the samples in a centrifugal vacuum concentrator. |
| 10. | Store the dry samples at −15 to −25° C. if you are not going to analyze them immediately. |

Further details on sample handling and LC/MS/MS settings for generation of the data of this example are as follows. Prior to loading on the LC column, each sample was reconstituted with 40 μL of 3% formic acid containing 10 pmole/μL of amino acid standard labeled with iTRAQ reagent 117. A volume of 2 μL was then injected into an Applied Biosystems/MDS Sciex API 3200 LC/MS/MS instrument using manufacturer recommended procedures. Details on the instruments operating conditions are presented in Tables 16-26. Tables 16 and 17 providing conditions related to the LC portion of the instrument and Tables 18-26 providing conditions related to the MS/MS portion of the instrument.

TABLE 16

LC Conditions

Devices:

| | |
|---|---|
| AutoSampler | Agilent 1100 G1367A |
| Pump | Agilent 1100 G1312A |
| Column Oven | Agilent 1100 G1316A |

Agilent 1100 Autosampler Properties

| | |
|---|---|
| Autosampler Model: | Agilent 1100 Wellplate Autosampler |
| Syringe Size (μl): | 100 |
| Injection Volume (μl): | 2.00 |
| Draw Speed (μl/min): | 200.0 |
| Eject Speed (μl/min): | 200.0 |

Agilent 1100 LC Pump Method Properties

| | |
|---|---|
| Pump Model: | Agilent 1100 LC Binary Pump |
| Minimum Pressure (psi): | 0.0 |
| Maximum Pressure (psi): | 5801.0 |
| Dead Volume (μl): | 40.0 |
| Maximum Flow Ramp (ml/min²): | 100.0 |
| Maximum Pressure Ramp (psi/sec): | 290.0 |
| Left Compressibility: | 50.0 |
| Right Compressibility: | 115.0 |
| Left Dead Volume (μl): | 40.0 |
| Right Dead Volume (μl): | 40.0 |
| Left Stroke Volume (μl): | −1.0 |
| Right Stroke Volume (μl): | −1.0 |
| Left Solvent: | A1 |
| Right Solvent: | B1 |
| Column: | |

Higgins Analytical, PHALANX C18, 5 um, 150 × 4.6 mm
Column Temperature (° C.): 50.00
Mobile Phases:

Solvent A: 0.1% Formic acid, 0.005% Heptafluorobutyric acid in water
Solvent B: 0.1% Formic acid, 0.005% Heptafluorobutyric acid in acetonitrile
Heptafluorobutyric acid is added as an ion-pairing reagent to increase the resolution of the separation.

TABLE 17

LC GRADIENT

| Step | Total Time (min) | Flow Rate (μl/min) | Solvent A (%) | Solvent B (%) |
|---|---|---|---|---|
| 0 | 0.00 | 450 | 98.0 | 2.0 |
| 1 | 10.00 | 450 | 72.0 | 28.0 |
| 2 | 10.10 | 450 | 0.0 | 100.0 |
| 3 | 16.00 | 450 | 0.0 | 100.0 |
| 4 | 16.10 | 450 | 98.0 | 2.0 |
| 5 | 25.00 | 450 | 98.0 | 2.0 |

In the present example, multiple periods (periods 1-4) are used in the MS/MS data acquisition so that all transitions are not scanned continuously during the run. Only those transitions in a period are scanned during that period. This can allow for more data points per peak which results in better quantitation.

TABLE 18

MS/MS ANALYSIS CONDITIONS

Devices:

| | |
|---|---|
| Mass Spectrometer Acquisition Info: | API 3200 |
| Sample Acq Duration: | 25 min 0 sec |
| Number of Scans: | 1251 |
| Periods in File: | 4 |
| Software Version: | Analyst 1.4.1 |
| Quantitation Info: | |
| Dilution Factor: | 1.000000 |

TABLE 19

PERIOD 1: TRANSMITTED MASS PARAMETER TABLE

| Amino Acid | Q1 Mass (amu) | Q3 Mass (amu) |
|---|---|---|
| Taurine | 270.30 | 114.10 |
| | 270.30 | 117.10 |
| O-phosphoethanolamine | 286.30 | 114.10 |
| | 286.30 | 117.10 |
| O-phospho-L-serine | 330.30 | 114.10 |
| | 330.30 | 117.10 |

TABLE 20

PERIOD 1: PARAMETERS

| | |
|---|---|
| Scans in Period: | 267 |
| Relative Start Time: | 0.00 msec |
| Experiments in Period: | 1 |
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thresh.: | 0.00 cps |
| Settling Time: | 0.0000 msec |
| MR Pause: | 5.0070 msec |
| MCA: | No |
| Step Size: | 0.00 amu |

TABLE 21

PERIOD 2: TRANSMITTED MASS PARAMETER TABLE

| Amino Acid | Q1 Mass (amu) | Q3 Mass (amu) |
|---|---|---|
| ethanolamine | 206.20 | 114.10 |
| | 206.20 | 117.10 |
| Gly | 220.20 | 114.10 |
| | 220.20 | 117.10 |
| Ser | 250.20 | 114.10 |
| | 250.20 | 117.10 |
| hydroxy-L-proline | 276.30 | 114.10 |
| | 276.30 | 117.10 |
| Asn | 277.30 | 114.10 |
| | 277.30 | 117.10 |
| Asp | 278.30 | 114.10 |
| | 278.30 | 117.10 |
| Gln | 291.30 | 114.10 |
| | 291.30 | 117.10 |

TABLE 22

PERIOD 2: PARAMETERS

| | |
|---|---|
| Scans in Period: | 82 |
| Relative Start Time: | 2.80 min |
| Experiments in Period: | 1 |
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thresh.: | 0.00 cps |
| Settling Time: | 0.0000 msec |
| MR Pause: | 5.0070 msec |
| MCA: | No |
| Step Size: | 0.00 amu |

TABLE 23

PERIOD 3: TRANSMITTED MASS PARAMETER TABLE

| Amino Acid | Q1 Mass (amu) | Q3 Mass (amu) |
|---|---|---|
| | 218.20 | 114.10 |
| | 218.20 | 117.10 |
| b-alanine, Ala, Sarcosine | 234.20 | 114.10 |
| | 234.20 | 117.10 |
| ABA, BAIBA, GABA | 248.20 | 114.10 |
| | 248.20 | 117.10 |
| Pro | 260.30 | 114.10 |
| | 260.30 | 117.10 |
| Thr | 264.30 | 114.10 |
| | 264.30 | 117.10 |
| Glu | 292.30 | 114.10 |
| | 292.30 | 117.10 |
| His | 300.30 | 114.10 |
| | 300.30 | 117.10 |
| AAA | 306.30 | 114.10 |
| | 306.30 | 117.10 |
| 1-methyl-L-histidine, 3-methyl-L-histidine | 314.30 | 114.10 |
| | 314.30 | 117.10 |
| Arg | 319.30 | 114.10 |
| | 319.30 | 117.10 |
| Cit | 320.30 | 114.10 |
| | 320.30 | 117.10 |
| L-carnosine | 371.40 | 114.10 |
| | 371.40 | 117.10 |
| L-anserine | 385.40 | 114.10 |
| | 385.40 | 117.10 |

TABLE 23-continued

PERIOD 3: TRANSMITTED MASS PARAMETER TABLE

| Amino Acid | Q1 Mass (amu) | Q3 Mass (amu) |
|---|---|---|
| Orn | 421.40 | 114.10 |
| | 421.40 | 117.10 |
| d-hydroxylysine | 451.50 | 114.10 |
| | 451.50 | 117.10 |
| cystathionine | 511.50 | 114.10 |
| | 511.50 | 117.10 |

TABLE 24

PERIOD 3: PARAMETERS

| | |
|---|---|
| Scans in Period: | 150 |
| Relative Start Time: | 4.81 min |
| Experiments in Period: | 1 |
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thres.: | 0.00 cps |
| Settling Time: | 0.0000 msec |
| MR Pause: | 5.0070 msec |
| MCA: | No |
| Step Size: | 0.00 amu |

TABLE 25

PERIOD 4: TRANSMITTED MASS PARAMETER TABLE

| Amino Acid | Q1 Mass (amu) | Q3 Mass (amu) |
|---|---|---|
| Val | 262.30 | 114.10 |
| | 262.30 | 117.10 |
| Ile, Leu, Nle | 276.30 | 114.10 |
| | 276.30 | 117.10 |
| Met | 294.30 | 114.10 |
| | 294.30 | 117.10 |
| Phe | 310.30 | 114.10 |
| | 310.30 | 117.10 |
| Tyr | 326.30 | 114.10 |
| | 326.30 | 117.10 |
| Trp | 349.30 | 114.10 |
| | 349.30 | 117.10 |

TABLE 26

PERIOD 4: PARAMETERS

| | |
|---|---|
| Scans in Period: | 752 |
| Relative Start Time: | 9.21 min |
| Experiments in Period: | 1 |
| Scan Type: | MRM (MRM) |
| Polarity: | Positive |
| Scan Mode: | N/A |
| Ion Source: | Turbo Spray |
| Resolution Q1: | Unit |
| Resolution Q3: | Unit |
| Intensity Thres.: | 0.00 cps |
| Settling Time: | 0.0000 msec |
| MR Pause: | 5.0070 msec |
| MCA: | No |
| Step Size: | 0.00 amu |

Spectra and Results:

In the present example, 48 amino acids were monitored. Table 27 summarizes the data obtained for each detected amino acid. The second column lists the amount of the amino acid in the internal standard, the third column the amount in the external standard spike, column four lists the measured amino acid level in the sample and column five the plasma control range.

TABLE 27

| Amino Acid | μM IS | Ext std spike μM | Sample (μM) | Plasma control range μM |
|---|---|---|---|---|
| VAL | 62.1 | 52.3 | 59.0 | 49-69 |
| TYR | 22.3 | 18.7 | 17.0 | 13-22 |
| TRP | 21.0 | 0.0 | | |
| THR | 48.5 | 41.5 | 42.0 | 38-48 |
| TAU | 19.5 | 9.1 | 14.0 | |
| SER | 31.9 | 30.7 | 26.0 | 23-30 |
| SAR | 0.7 | 0.6 | | |
| PSER | 0.0 | 0.1 | | |
| PRO | 118.9 | 98.4 | 44.0 | 34-52 |
| PHE | 19.3 | 18.1 | 15.0 | 12-25 |
| PETN | 0.5 | 0.6 | | |
| ORN | 33.3 | 17.8 | 27.0 | |
| MET | 7.7 | 7.0 | 6.0 | 4-7 |
| LYS | 262.7 | 56.0 | 46.0 | 39-52 |
| LEU | 46.0 | 35.7 | 30.0 | 26-35 |
| ILE | 21.3 | 19.6 | 14.0 | 13-18 |
| HYP | 2.5 | 2.7 | 1.8 | |
| HYL | 0.8 | 0.6 | | |
| HIS | 22.8 | 18.9 | 16.0 | 0-22 |
| GLY | 83.3 | 70.6 | 67.0 | 59-74 |
| GLU | 25.3 | 23.8 | 20.0 | 17-25 |
| GLN | 150.3 | 254.8 | 155.0 | |
| GABA | 0.6 | 0.6 | | |
| ETN | 6.6 | 6.3 | | |
| CYSTA | 0.5 | 0.4 | | |
| CIT | 9.0 | 7.1 | 5.0 | |
| CAR | 1.2 | 1.0 | | |
| BALA | 11.7 | 15.4 | | |
| BAIBA | 1.9 | 1.7 | | |
| ASP | 1.9 | 2.2 | 2.4 | 2-4 |
| ASN | 24.2 | 0.0 | 13.0 | |
| ARG | 24.0 | 12.4 | 14.0 | 11-17 |
| ANS | 0.8 | 0.6 | | |
| ALA | 137.3 | 136.8 | 115.0 | 98-130 |
| AANB | 4.4 | 4.0 | 3.0 | |
| AAD | 0.5 | 0.4 | | |
| 3-MHS | 2.4 | 2.4 | 1.0 | |
| 1-MHS | 1.8 | 1.4 | 3.0 | |
| (HCY)2 | 0.7 | 0.7 | | |
| (CYS)2 | 13.5 | 6.2 | | |

Example 7

Catecholamines

The present example discusses chromatogram separation of iTRAQ labeled catecholamines (CATs). CATs are often of interest in the clinical analysis of urine, plasma and CSF (cerebro spinal fluids) samples. Routine clinical analysis in plasma and urine is performed, e.g., to diagnose tumors (neuroblastoma, pheacytochroma etc.) and their age and location. CAT's are also often neurotransmitters and are monitored in CSF, e.g., in pharmaceutical industry in drug development of hypretension drugs.

Catecholamines and related compounds are important cardiovascular and metabolic effectors. Determining the concentrations of these compounds in various biological fluids has significance in clinical and pharmaceutical development laboratories. At present, the standard analytical methods are prone to a variety of chemical and chromatographic interferences. Here we present a novel method for the high sensitivity quantitation of catecholamines, related compounds and amino acids in a single analysis using the iTRAQ chemistry, a set of four amine reactive, isobaric, multiplex labeling reagents. The derivatives are analyzed and quantitated using LC-MS/MS in MRM (multiple reaction monitoring) mode providing very high degrees of sensitivity and specificity.

In the present example, the CATs histamine, norepinephrine, epinephrine, metanephrine, dopamine, and serotonin are monitored. In addition, the amino acids glu and tyr are monitored.

Materials & Methods

Standard mixtures of catecholamines, related compounds and several amino acids were prepared and labeled with iTRAQ reagents using the standard protocol. Derivatives were separated on a C18 reversed phase column using a water-acetonitrile gradient containing volatile ion-pairing reagent at a flow rate of 1 mL/minute. A series of dilutions of the derivatized standards were injected to determine LODs (limits of detection) and calibration curves for the various components. Biological fluid samples (urine, CSF, plasma), with and without added standard, were prepared according to published protocols, labeled and analyzed to determine matrix effects on the sensitivity and accuracy of the method. Samples were analyzed with Applied Biosystems/MDS SCIEX API-4000 triple quadrupole mass spectrometer, ESI+, MRM mode.

Results

The results demonstrate the feasibility of labeling and quantifying the following catecholamines, related compounds and amino acids: Dopa (3,4-Dihydroxy-DL-phenylanine), Dopamine, Epinephrine, Norepinephrine, Metanephrine, Normetanephrine, Methyl Dopa, 3-Methoxytyramine, Seratonin, Histamine, ABA (Aminobutyric acid), Tyrosine, and Glutamic acid. LOD at time of abstract submission is 0.004 picomole/uL. Linearity for the various samples ranges from (R=0.9000 to 0.9998). Accuracy and precision are addressed. Baseline separation has been achieved for catecholamine isomers Dopa (342/117) and Metanephrine (342/117) as well as for Epinephrine (328/117) and Normetanephrine (328/117).

Example 8

Dynamic Range

FIGS. 27A and 27B present data on the dynamic range and response of various embodiments of the present teachings for the determination of amino acid concentrations. FIG. 27A presents data on the response for concentrations of norvaline from about 10 to about 990 picomole (pmole). Each of the experiments (data points) uses a 30 pmole internal standard and triplicate injections. Increasing amounts of amino acid were injected on the LC/MS/MS system and plotted against their response. FIG. 27A indicates that the response is linear over about 3 orders of magnitude of concentration.

FIG. 27B presents data on the response for concentrations of leucine from about 10 to about 990 picomole (pmole). Each of the experiments (data points) uses a 30 pmole internal standard and triplicate injections. Increasing amounts of amino acid were injected on the LC/MS/MS system and plotted against their response. FIG. 29B indicates that the response is linear over about 3 orders of magnitude of concentration.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While the teachings have been particularly shown and described with reference to specific illustrative embodiments, it should be understood that various changes in form and detail may be made without departing from the spirit and scope of the teachings. By way of example, any of the disclosed steps can be combined with any of the other disclosed steps to provide a method of analyze amine-containing compounds in accordance with various embodiments of the invention. Therefore, all embodiments that come within the scope and spirit of the teachings, and equivalents thereto, are claimed. The descriptions and diagrams of the methods, systems, and assays of the present teachings should not be read as limited to the described order of elements unless stated to that effect.

What is claimed is:

1. A method for analyzing one or more amine-containing compounds in one or more samples comprising:
   providing a standard compound;
   labeling the standard compound with an isobaric tag from a set of isobaric tags to form an isobarically labeled standard compound;
   labeling the one or more amine-containing compounds in the one or more samples, each sample with a different respective isobaric tag from the set of isobaric tags, to form one or more samples of one or more isobarically labeled amine-containing compounds;
   combining at least a portion of the isobarically labeled standard compound and at least a portion of each sample of the one or more isobarically labeled amine-containing compounds to produce a combined sample;
   loading at least a portion of the combined sample on a chromatographic column;
   eluting components of the combined sample from the chromatographic column;
   subjecting at least a portion of the eluted components to parent-daughter ion transition monitoring, wherein
      a first transmitted parent ion m/z range includes an m/z value of one or more of the isobarically labeled amine containing compounds and a first transmitted daughter ion m/z range includes an m/z value of at least one reporter ion corresponding to at least one of the isobaric tags of the one or more isobarically labeled amine containing compounds; and
      a second transmitted parent ion m/z range includes an m/z value of the isobarically labeled standard compound and a second transmitted daughter ion m/z range includes an m/z value of a reporter ion corresponding to the isobaric tag of the isobarically labeled standard compound;
   measuring the ion signal of one or more of the transmitted reporter ions; and
   determining the concentration of one or more of the isobarically labeled amine-containing compounds based at least on a comparison of the measured ion signal of at least one reporter ion corresponding to at least one of the isobaric tags of the one or more isobarically labeled amine-containing compounds to the measured ion signal of the reporter ion corresponding to the isobaric tag of the isobarically labeled standard compound;
   wherein the one or more amine-containing compounds comprise one or more free amino acids, catecholamines, or nitrofuran metabolites.

2. The method of claim 1, wherein one or more of the samples comprise a physiological fluid.

3. The method of claim 1, wherein one or more of the samples comprise one or more of an agricultural product, animal product, animal feed, a food for human consumption, and a beverage for human consumption.

4. The method of claim 1, wherein the method analyzes substantially the same amine-containing compound from two or more samples.

5. The method of claim 1, wherein the one or more amine-containing compounds comprise one or more free amino acids.

6. The method of claim 5, wherein the one or more amine-containing compounds comprise one or more isomers of the same free amino acid.

7. The method of claim 5, wherein the one or more amine-containing compounds comprise one or more post translational modifications of the same free amino acid.

8. The method of claim 1, wherein the one or more amine-containing compounds comprise one or more amine-containing compounds contained in a protein or polypeptide.

9. The method of claim 1, wherein the one or more amine-containing compounds comprise one or more catecholamines or nitrofuran metabolites.

10. The method of claim 9, wherein the one or more amine-containing compounds comprise one or more of epinephrine, norepinephrine, and L-dopa.

11. The method of claim 9, wherein the one or more amine-containing compounds comprise one or more of 3-amino-2-oxazolidinone, 5-morpholinomethyl-3-amino-oxazolidinone, semicarbazide, and 1-aminohydantoin.

12. The method of claim 1, wherein subjecting at least a portion of the eluted components to parent-daughter ion transition monitoring comprises using one or more of a triple quadrupole, quadrupole/time-of-flight mass spectrometer, linear ion trap mass spectrometer, or a tandem time-of-flight mass spectrometer.

13. The method of claim 1, wherein subjecting at least a portion of the eluted components to parent-daughter ion transition monitoring comprises mixing the combined sample in a matrix and using matrix assisted laser desorption ionization to produce ions for the parent-daughter ion transition monitoring.

14. The method of claim 13, wherein the one or more amine-containing compounds comprise one or more of lysine, an isomer of lysine, and a post translationally modified lysine, and the matrix comprises a cyano-4-hydroxy cinnamic acid (CHCA).

15. The method of claim 13, wherein the one or more amine-containing compounds comprise one or more of arginine, an isomer of arginine, and a post translationally modified arginine, and the matrix comprises a dihydroxybenzoic acid (DHB).

16. The method of claim 1, wherein determining the concentration of one or more of the isobarically labeled amine-containing compounds comprises determining the absolute concentration of one or more of the isobarically labeled amine-containing compounds.

17. A method for analyzing one or more amine-containing compounds in one or more samples comprising:
- labeling each of the one or more amine-containing compounds in the one or more samples, each sample with a different respective isobaric tag from a set of isobaric tags, to form one or more samples of one or more isobarically labeled amine-containing compounds;
- combining at least a portion of each sample of the one or more isobarically labeled amine-containing compounds to produce a combined sample;
- loading at least a portion of the combined sample on a chromatographic column;
- eluting components of the combined sample from the chromatographic column;
- subjecting at least a portion of the eluted components to parent-daughter ion transition monitoring, wherein a transmitted parent ion m/z range includes an m/z value of one or more of the isobarically labeled amine containing compounds and a transmitted daughter ion m/z range includes an m/z value of at least one reporter ion corresponding to at least one of the isobaric tags of the one or more isobarically labeled amine containing compounds;
- measuring the ion signal of one or more of the transmitted reporter ions; and
- determining the concentration of one or more of the isobarically labeled amine-containing compounds based at least on a comparison of the measured ion signal of at least one reporter ion corresponding to at least one of the isobaric tags of the one or more isobarically labeled amine-containing compounds to a concentration curve of a standard compound;
- wherein the one or more amine-containing compounds comprise one or more free amino acids, catecholamines, or nitrofuran metabolites.

18. The method of claim 17, where the concentration curve of the standard compound is generated by:
- (a) providing a standard compound having a first concentration;
- (b) labeling the standard compound with an isobaric tag from a set of isobaric tags to form an isobarically labeled standard compound;
- (c) loading at least a portion of the isobarically labeled standard compound on a chromatographic column and eluting components of the isobarically labeled standard compound from the chromatographic column;
- (d) subjecting at least a portion of the eluted components to parent-daughter ion transition monitoring, wherein a transmitted parent ion m/z range includes an m/z value of the isobarically labeled standard compound and a transmitted daughter ion m/z range includes an m/z value of a reporter ion corresponding to the isobaric tag of the isobarically labeled standard compound;
- (e) measuring the ion signal of the transmitted reporter ions;
- (f) repeating steps (a)-(e) for one or more different standard compound concentrations; and
- (g) generating a concentration curve for the standard compound based at least on the measured ion signal of the transmitted reporter ions at two or more standard compound concentrations.

19. The method of claim 17, wherein determining the concentration of one or more of the isobarically labeled amine-containing compounds comprises determining the absolute concentration of one or more of the isobarically labeled amine-containing compounds.

20. A method for analyzing one or more amine-containing compounds in one or more samples comprising
- labeling the one or more amine-containing compounds in the one or more samples, each sample with a different respective isobaric tag from a set of isobaric tags, to form one or more samples of one or more isobarically labeled amine-containing compounds;
- combining at least a portion of each sample of the one or more isobarically labeled amine-containing compounds to produce a combined sample;
- subjecting at least a portion of the combined sample to parent-daughter ion transition monitoring using matrix assisted laser desorption ionization, wherein a first transmitted parent ion m/z range includes an m/z value of one or more of the isobarically labeled amine containing compounds and a first transmitted daughter ion m/z range includes an m/z value of at least one reporter ion corresponding to at least one of the isobaric tags of the one or more isobarically labeled amine containing compounds;
- measuring the ion signal of one or more of the transmitted reporter ions; and
- determining the concentration of one or more of the isobarically labeled amine-containing compounds based at least on a comparison of the measured ion signal of at least one reporter ion corresponding to at least one of the isobaric tags of the one or more isobarically labeled amine-containing compounds to the measured ion signal corresponding to a standard compound;
- wherein the one or more amine-containing compounds comprise one or more free amino acids, catecholamines, or nitrofuran metabolites.

21. The method of claim 20, wherein the one or more amine-containing compounds comprise one or more of lysine, an isomer of lysine, and a post translationally modified lysine, and the matrix comprises a cyano-4-hydroxy cinnamic acid (CHCA).

22. The method of claim 20, wherein the one or more amine-containing compounds comprise one or more of arginine, an isomer of arginine, and a post translationally modified arginine, and the matrix comprises a dihydroxybenzoic acid (DHB).

23. The method of claim 20, wherein determining the concentration of one or more of the isobarically labeled amine-containing compounds comprises determining the absolute concentration of one or more of the isobarically labeled amine-containing compounds.

24. The method of claim 1, wherein the standard compound is labeled with an isobaric tag that is different from the isobaric tags used to label the one or more amine-containing compounds in the one or more samples.

25. The method of claim 1, comprising analyzing one or more amine-containing compounds in a plurality of samples.

26. The method of claim 17, comprising analyzing one or more amine-containing compounds in a plurality of samples.

27. The method of claim 20, comprising analyzing one or more amine-containing compounds in a plurality of samples.

28. The method of claim 20, wherein the measured ion signal corresponding to the standard compound corresponds to the measured ion signal of a reporter ion from a labeled standard compound.

29. The method of claim 28, wherein the labeled standard compound is labeled with a tag that is isobaric with respect to the isobaric tags used to label the one or more amine-containing compounds in the one or more samples.

30. The method of claim 29, wherein the labeled standard compound is one of the one or more isobarically labeled-amine-containing compounds.

* * * * *